US012694635B2

(12) United States Patent
Chaoui et al.

(10) Patent No.: US 12,694,635 B2
(45) Date of Patent: Jul. 28, 2026

(54) PRE-OPERATIVE PLANNING OF SURGICAL REVISION PROCEDURES FOR ORTHOPEDIC JOINTS

(71) Applicant: Howmedica Osteonics Corp., Mahwah, NJ (US)

(72) Inventors: Jean Chaoui, Lyons (FR); Maximilien Mayya, Antibes (FR)

(73) Assignee: Howmedica Osteonics Corp., Mahwah, NJ (US)

( * ) Notice: Subject to any disclaimer, the term of this patent is extended or adjusted under 35 U.S.C. 154(b) by 83 days.

(21) Appl. No.: 18/680,480

(22) Filed: May 31, 2024

(65) Prior Publication Data

US 2024/0320942 A1     Sep. 26, 2024

Related U.S. Application Data

(63) Continuation of application No. 17/635,177, filed as application No. PCT/US2020/046484 on Aug. 14, 2020, now Pat. No. 12,045,943.

(60) Provisional application No. 62/887,838, filed on Aug. 16, 2019.

(51) Int. Cl.
| | |
|---|---|
| *G06T 19/20* | (2011.01) |
| *A61B 6/03* | (2006.01) |
| *A61B 34/10* | (2016.01) |

(52) U.S. Cl.
CPC .............. *G06T 19/20* (2013.01); *A61B 6/032* (2013.01); *A61B 34/10* (2016.02); *A61B 2034/102* (2016.02); *A61B 2034/105* (2016.02); *G06T 2210/41* (2013.01); *G06T 2219/2004* (2013.01); *G06T 2219/2016* (2013.01)

(58) Field of Classification Search
CPC ... A61B 34/10; A61B 6/032; A61B 2034/105; A61B 2034/102; G06T 2219/2021; G06T 2219/2016; G06T 2219/2012; G06T 2219/2004; G06T 19/20; G06T 2210/41
USPC ........................................................ 345/418
See application file for complete search history.

(56) References Cited

U.S. PATENT DOCUMENTS

| | | | |
|---|---|---|---|
| 7,715,602 | B2 | 5/2010 | Richard |
| 7,857,821 | B2 | 12/2010 | Couture et al. |
| 7,974,677 | B2 | 7/2011 | Mire et al. |
| 8,147,496 | B2 | 4/2012 | Couture et al. |
| 8,506,645 | B2 | 8/2013 | Blaylock et al. |

(Continued)

FOREIGN PATENT DOCUMENTS

| | | |
|---|---|---|
| FR | 3108419 A1 | 9/2021 |
| KR | 20180044421 A | 5/2018 |

(Continued)

OTHER PUBLICATIONS

Mahfouz MR, Hoff WA, Komistek RD, Dennis DA. Effect of segmentation errors on 3D-to-2D registration of implant models in X-ray images. Journal of biomechanics. Feb. 1, 2005;38(2):229-39.*

(Continued)

*Primary Examiner* — Phu K Nguyen
(74) *Attorney, Agent, or Firm* — Shumaker & Sieffert, P.A.

(57)     ABSTRACT

A system is configured to obtain image data of a joint of a patient; determine that the joint includes an existing implant; and one or both of generate an identification of a type for the existing implant and generate a pre-implant, morbid approximation of the joint.

20 Claims, 35 Drawing Sheets

(56) References Cited

U.S. PATENT DOCUMENTS

| | | | |
|---|---|---|---|
| 8,842,893 B2 | 9/2014 | Teichman et al. | |
| 8,891,847 B2 | 11/2014 | Helm | |
| 8,971,606 B2 | 3/2015 | Chaoui et al. | |
| 9,317,661 B2 | 4/2016 | Helm | |
| 9,675,273 B2 | 6/2017 | Gluncic | |
| 9,808,261 B2 | 11/2017 | Gelaude et al. | |
| 10,172,715 B2 | 1/2019 | De Wilde et al. | |
| 10,194,991 B2 | 2/2019 | Bonny et al. | |
| 10,350,010 B2 | 7/2019 | Kao et al. | |
| 10,426,549 B2 | 10/2019 | Kehres et al. | |
| 10,489,907 B2 | 11/2019 | Rowley Grant et al. | |
| 10,881,462 B2 | 1/2021 | Heavener et al. | |
| 11,090,019 B2 | 8/2021 | Siemionow et al. | |
| 11,576,725 B2 | 2/2023 | Chav et al. | |
| 2010/0191071 A1* | 7/2010 | Anderson | G16H 50/50 |
| | | | 703/11 |
| 2012/0192401 A1 | 8/2012 | Pavlovskaia et al. | |
| 2012/0289965 A1 | 11/2012 | Gelaude et al. | |
| 2013/0188848 A1* | 7/2013 | Helm | G16H 50/50 |
| | | | 382/131 |
| 2014/0336660 A1* | 11/2014 | Gibson | A61F 2/4609 |
| | | | 606/91 |
| 2017/0215967 A1 | 8/2017 | Spath | |
| 2017/0360509 A1* | 12/2017 | Bonny | A61B 34/10 |
| 2018/0014891 A1* | 1/2018 | Krebs | A61B 90/361 |
| 2018/0217734 A1 | 8/2018 | Koenig et al. | |
| 2018/0233222 A1 | 8/2018 | Daley et al. | |
| 2019/0146458 A1* | 5/2019 | Roh | G05B 19/4099 |
| | | | 700/98 |
| 2019/0175277 A1 | 6/2019 | Chav et al. | |
| 2020/0297424 A1* | 9/2020 | Helm | A61B 34/10 |
| 2021/0015560 A1* | 1/2021 | Boddington | G06V 10/426 |
| 2021/0038315 A1* | 2/2021 | Bonny | A61F 2/389 |
| 2021/0153946 A1 | 5/2021 | Bonny et al. | |
| 2021/0361357 A1 | 11/2021 | Crawford | |
| 2022/0110683 A1* | 4/2022 | Farley | A61B 34/20 |
| 2023/0056596 A1 | 2/2023 | Farley et al. | |

FOREIGN PATENT DOCUMENTS

| | | | |
|---|---|---|---|
| WO | 2009106816 A1 | 9/2009 | |
| WO | 2017041080 A1 | 3/2017 | |
| WO | 2019046579 A1 | 3/2019 | |
| WO | 2020123701 A1 | 6/2020 | |
| WO | 2020205245 A1 | 10/2020 | |
| WO | WO-2021034706 A1 * | 2/2021 | G06T 19/20 |
| WO | 2021185940 A1 | 9/2021 | |
| WO | 2022046966 A1 | 3/2022 | |

OTHER PUBLICATIONS

Xie K, Gao L, Zhang Y, Zhang H, Sun J, Lin T, Sui J, Ni X. Metal implant segmentation in CT images based on diffusion model. BMC Medical Imaging. Aug. 6, 2024;24(1):204.*

Communication pursuant to Article 94(3) EPC from counterpart European Application No. 20761723.4 dated May 26, 2025, p. 3.

Response to Office Action dated Jan. 14, 2025, from counterpart Japanese Application No. 2023-135414 filed Apr. 21, 2025, 9 pp. Translation Attached.

"Blueprint 3d Planning Software + PSI," Wright Medical Group, retrieved from https://www.wright.com/blueprint-3d-planning-psi-system on Oct. 15, 2020, 9 pp.

"Chapter 4—Statistical Shape Models," dated Aug. 22, 2006, 17 pp, retrieved from http://www.cmlab.csie.ntu.edu.tw/~cyy/learning/papers/PCA_ASM.pdf.

"HoloLens 2," Microsoft HoloLens, retrieved from https://www.microsoft.com/en-us/hololens, on Oct. 15, 2020, 5 pp.

Abler et al., "A statistical shape model to predict the premorbid glenoid cavity," Journal of Shoulder and Elbow Surgery, vol. 27, No. 10, Jun. 2018, 9 pp.

Boissonnat, J.D., "Shape Reconstruction from Planar Cross Sections," Computer Vision, Graphics, and Image Processing, vol. 44, No. 1, Oct. 1988, 29 pp.

Horn, B. K. P., "Closed-form solution of absolute orientation using unit quaternions," Journal of the Optical Society of America A, vol. 4, No. 4, Apr. 1987, 14 pp.

International Preliminary Report on Patentability from International Application No. PCT/US2020/046484, dated Mar. 3, 2022, 7 pp.

International Search Report and Written Opinion of International Application No. PCT/US2020/046484, dated Dec. 21, 2020, 9 pp.

Marker et al., "Contour-Based Surface Reconstruction using Implicit Curve Fitting, and Distance Field Filtering and Interpolation," Volume Graphics, Jan. 2006, 9 pp.

Nguyen et al., "A new segmentation method for MRI images of the shoulder joint," Fourth Canadian Conference on Computer and Robot Vision (CRV'07), May 2007, 8 pp.

Notice of Allowance from U.S. Appl. No. 17/635,177 dated Feb. 27, 2024, 7 pp.

Notice of Intent to Grant from counterpart Australian Application No. 2020331936 dated Oct. 12, 2023, 3 pp.

Notice of Intent to Grant from counterpart Japanese Application No. 2022-509002 dated Jul. 14, 2023, 5 pp.

Office Action from counterpart Australian Application No. 2020331936 dated May 22, 2023, 2 pp.

Office Action from counterpart Japanese Application No. 2022-509002 dated Apr. 4, 2023, 3 pp.

Office Action from U.S. Appl. No. 17/635,177 dated Sep. 28, 2023, 12 pp.

Response to Communication Pursuant to Rules 161(1) and 162 EPC dated Mar. 23, 2022, from counterpart European Application No. 20761723.4, filed Sep. 13, 2022, 34 pp.

Response to Office Action dated Apr. 4, 2023, from counterpart Japanese Application No. 2022-509002 filed Jun. 20, 2023, 6 pp.

Response to Office Action dated May 22, 2023, from counterpart Australian Application No. 2020331936 filed Sep. 29, 2023, 133 pp.

Response to Office Action dated Sep. 28, 2023 from U.S. Appl. No. 17/635,177, filed Dec. 21, 2023, 12 pp.

Wright Medical, "BluePrint Video-Wright Medical Announces the Acquisition of IMASCAP SAS", accessed from www.imascap.com/wp-content/uploads/2017/12/blueprintvid.mp4, Dec. 14, 2017, 9 pp.

Wright, "BluePrint, 3d Planning + PSI," User Manual V2.1, Tornier, CAW-8754, Nov. 2017, 18 pp.

First Examination Report from counterpart Australian Application No. 2024200427 dated Dec. 11, 2024, 2 pp.

Response to Office Action, and translation thereof, dated Jul. 9, 2024, from counterpart Japanese Application No. 2023-135414 filed Oct. 22, 2024, 13 pp.

Notice of Intent to Grant from counterpart Japanese Application No. 2023-135414 dated Jul. 8, 2025, 5 pp. Translation Attached.

Notice of Intent to Grant from counterpart Australian Application No. 2024200427 dated Sep. 4, 2025, 3 pp.

Response to Communication pursuant to Article 94(3) EPC dated May 26, 2025, from counterpart European Application No. 20761723.4 filed Sep. 24, 2025, 11 pp.

Response to Office Action dated Dec. 11, 2024, from counterpart Australian Application No. 2024200427 filed Aug. 29, 2025, 67 pp.

Notice of Intent to Grant and Text Intended to Grant from counterpart European Application No. 20761723.4 dated Jan. 7, 2025, 210 pp.

Office Action, and translation thereof, from counterpart Japanese Application No. 2023-135414 dated Jan. 14, 2025, 6 pp.

Office Action, and translation thereof, from counterpart Japanese Application No. 2023-135414 dated Jul. 9, 2024, 11 pp.

Notice of Intent to Grant and Text Intended to Grant from counterpart European Application No. 20761723.4 dated Dec. 8, 2025, 108 pp.

* cited by examiner

133B

133B

138

106

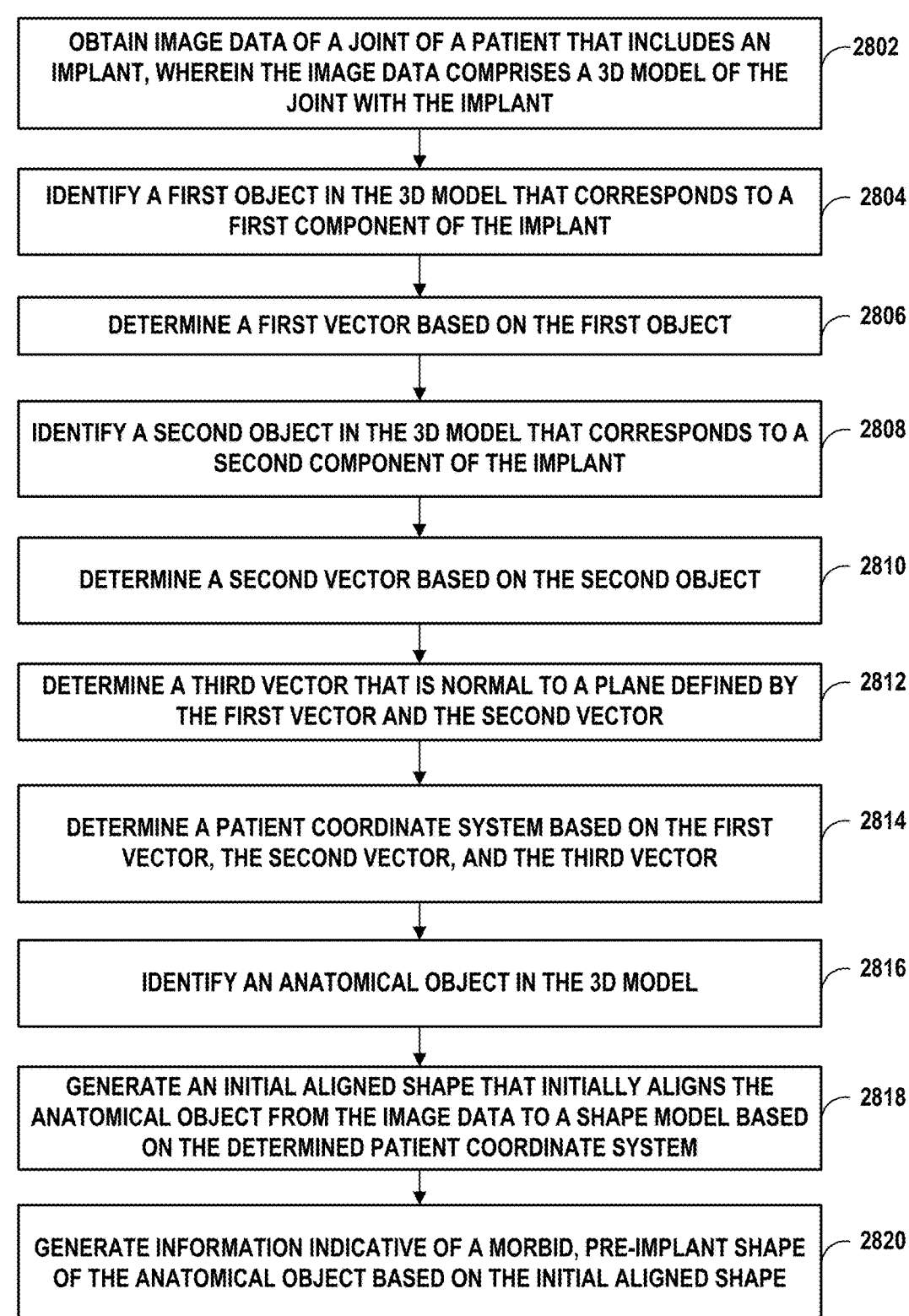

OBTAIN IMAGE DATA OF A JOINT OF A PATIENT THAT INCLUDES AN IMPLANT, WHEREIN THE IMAGE DATA COMPRISES A 3D MODEL OF THE JOINT WITH THE IMPLANT — 2802

IDENTIFY A FIRST OBJECT IN THE 3D MODEL THAT CORRESPONDS TO A FIRST COMPONENT OF THE IMPLANT — 2804

DETERMINE A FIRST VECTOR BASED ON THE FIRST OBJECT — 2806

IDENTIFY A SECOND OBJECT IN THE 3D MODEL THAT CORRESPONDS TO A SECOND COMPONENT OF THE IMPLANT — 2808

DETERMINE A SECOND VECTOR BASED ON THE SECOND OBJECT — 2810

DETERMINE A THIRD VECTOR THAT IS NORMAL TO A PLANE DEFINED BY THE FIRST VECTOR AND THE SECOND VECTOR — 2812

DETERMINE A PATIENT COORDINATE SYSTEM BASED ON THE FIRST VECTOR, THE SECOND VECTOR, AND THE THIRD VECTOR — 2814

IDENTIFY AN ANATOMICAL OBJECT IN THE 3D MODEL — 2816

GENERATE AN INITIAL ALIGNED SHAPE THAT INITIALLY ALIGNS THE ANATOMICAL OBJECT FROM THE IMAGE DATA TO A SHAPE MODEL BASED ON THE DETERMINED PATIENT COORDINATE SYSTEM — 2818

GENERATE INFORMATION INDICATIVE OF A MORBID, PRE-IMPLANT SHAPE OF THE ANATOMICAL OBJECT BASED ON THE INITIAL ALIGNED SHAPE — 2820

FIG. 28

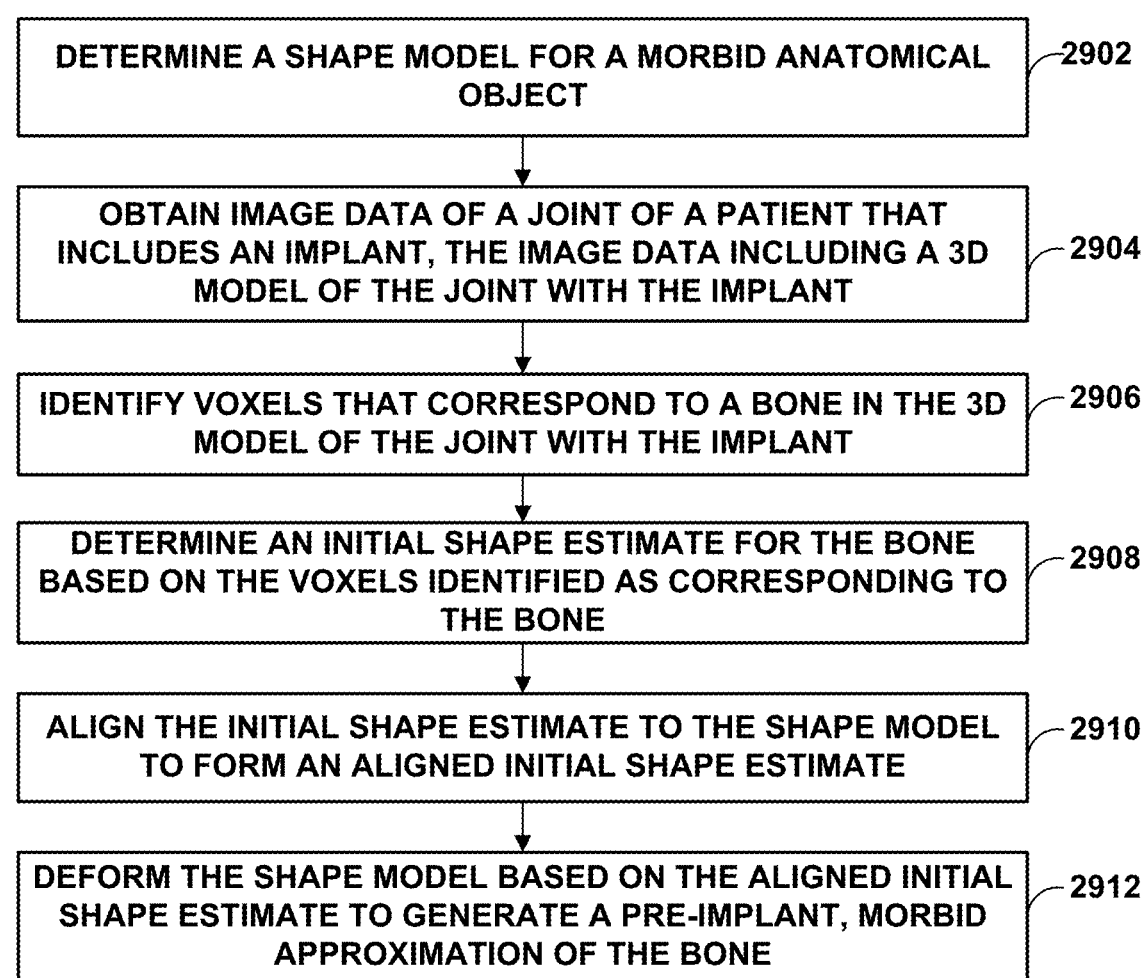

DETERMINE A SHAPE MODEL FOR A MORBID ANATOMICAL OBJECT — 2902

OBTAIN IMAGE DATA OF A JOINT OF A PATIENT THAT INCLUDES AN IMPLANT, THE IMAGE DATA INCLUDING A 3D MODEL OF THE JOINT WITH THE IMPLANT — 2904

IDENTIFY VOXELS THAT CORRESPOND TO A BONE IN THE 3D MODEL OF THE JOINT WITH THE IMPLANT — 2906

DETERMINE AN INITIAL SHAPE ESTIMATE FOR THE BONE BASED ON THE VOXELS IDENTIFIED AS CORRESPONDING TO THE BONE — 2908

ALIGN THE INITIAL SHAPE ESTIMATE TO THE SHAPE MODEL TO FORM AN ALIGNED INITIAL SHAPE ESTIMATE — 2910

DEFORM THE SHAPE MODEL BASED ON THE ALIGNED INITIAL SHAPE ESTIMATE TO GENERATE A PRE-IMPLANT, MORBID APPROXIMATION OF THE BONE — 2912

FIG. 29

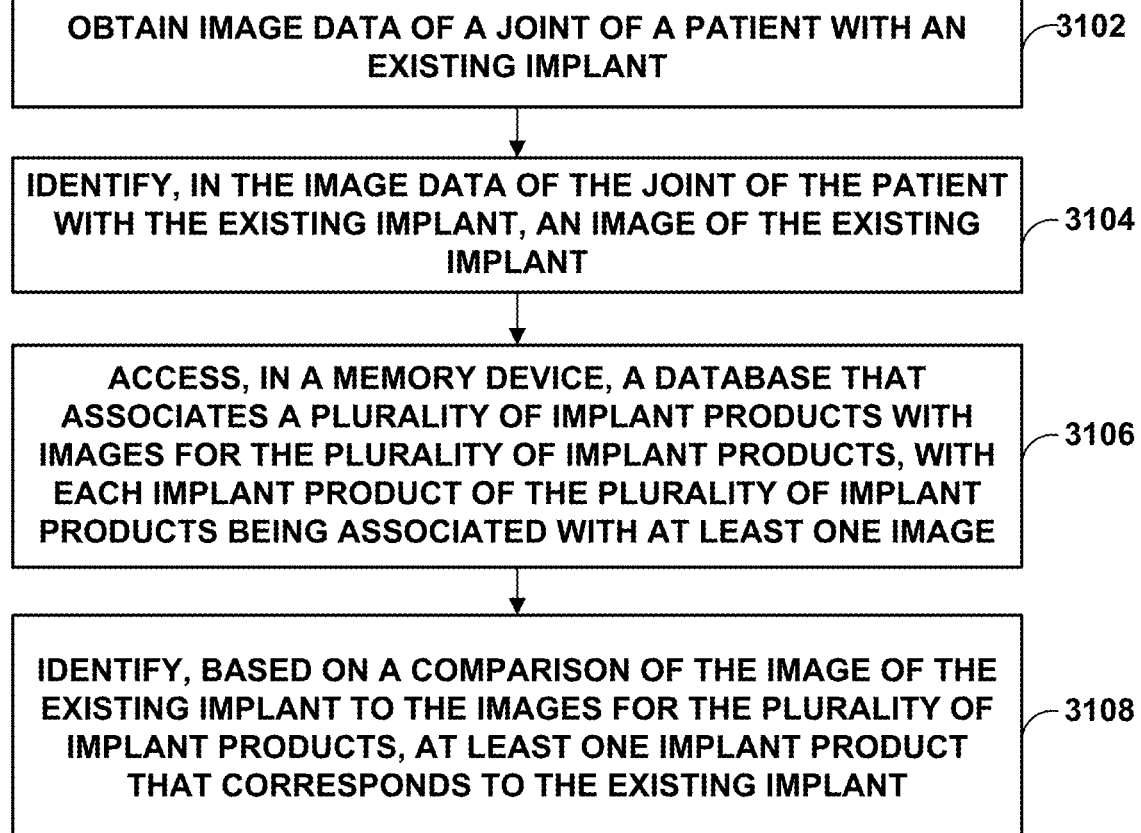

OBTAIN IMAGE DATA OF A JOINT OF A PATIENT WITH AN EXISTING IMPLANT ⟋3102

IDENTIFY, IN THE IMAGE DATA OF THE JOINT OF THE PATIENT WITH THE EXISTING IMPLANT, AN IMAGE OF THE EXISTING IMPLANT ⟋3104

ACCESS, IN A MEMORY DEVICE, A DATABASE THAT ASSOCIATES A PLURALITY OF IMPLANT PRODUCTS WITH IMAGES FOR THE PLURALITY OF IMPLANT PRODUCTS, WITH EACH IMPLANT PRODUCT OF THE PLURALITY OF IMPLANT PRODUCTS BEING ASSOCIATED WITH AT LEAST ONE IMAGE ⟋3106

IDENTIFY, BASED ON A COMPARISON OF THE IMAGE OF THE EXISTING IMPLANT TO THE IMAGES FOR THE PLURALITY OF IMPLANT PRODUCTS, AT LEAST ONE IMPLANT PRODUCT THAT CORRESPONDS TO THE EXISTING IMPLANT ⟋3108

FIG. 31

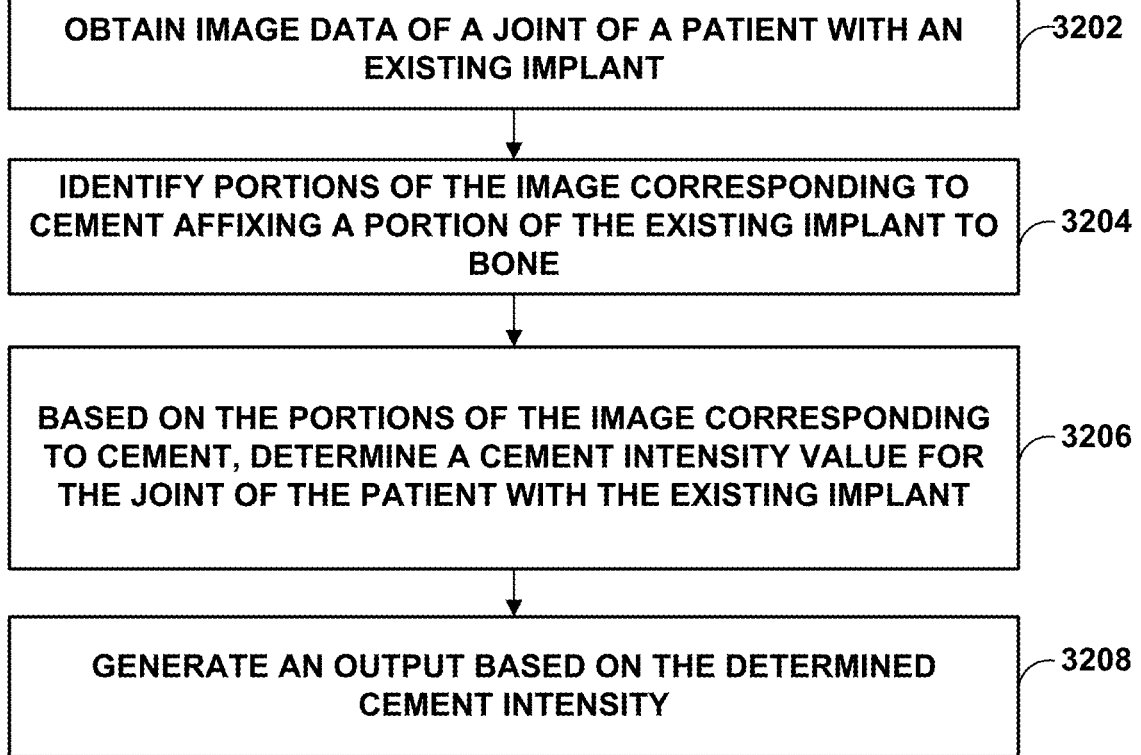

OBTAIN IMAGE DATA OF A JOINT OF A PATIENT WITH AN EXISTING IMPLANT ⟋‑3202

IDENTIFY PORTIONS OF THE IMAGE CORRESPONDING TO CEMENT AFFIXING A PORTION OF THE EXISTING IMPLANT TO BONE ⟋‑3204

BASED ON THE PORTIONS OF THE IMAGE CORRESPONDING TO CEMENT, DETERMINE A CEMENT INTENSITY VALUE FOR THE JOINT OF THE PATIENT WITH THE EXISTING IMPLANT ⟋‑3206

GENERATE AN OUTPUT BASED ON THE DETERMINED CEMENT INTENSITY ⟋‑3208

FIG. 32

PRE-OPERATIVE PLANNING OF SURGICAL REVISION PROCEDURES FOR ORTHOPEDIC JOINTS

This application is a continuation of U.S. patent application Ser. No. 17/635,177, filed 14 Feb. 2022, which is a national stage entry of PCT Application No. PCT/US2020/046484, filed 14 Aug. 2020, which claims the benefit of U.S. Provisional Patent Application 62/887,838, filed 16 Aug. 2019, the entire content of each being hereby incorporated by reference.

BACKGROUND

Surgical joint repair procedures involve repair and/or replacement of a damaged or diseased joint. A surgical joint repair procedure, such as joint arthroplasty as an example, may involve replacing the damaged joint or a damaged implant with a prosthetic that is implanted into the patient's bone. Proper selection or design of a prosthetic that is appropriately sized and shaped and proper positioning of that prosthetic are important to ensure an optimal surgical outcome. A surgeon may analyze damaged bone to assist with prosthetic selection, design and/or positioning, as well as surgical steps to prepare bone or tissue to receive or interact with a prosthetic.

SUMMARY

This disclosure describes techniques for determining a pre-implant, morbid approximation of a bone of an orthopedic joint in which one or more implant components have been placed. This disclosure also describes techniques determining a type of implant implanted into the orthopedic joint.

According to one example, a method includes determining a shape model for a morbid anatomical object; obtaining, by a computing system, image data of a joint of a patient that includes an implant, wherein the image data comprises a 3D model of the joint with the implant; in the 3D model of the joint with the implant, identifying voxels that correspond to a bone; based on the voxels identified as corresponding to the bone, determining an initial shape estimate for the bone; aligning the initial shape estimate to the shape model to form an aligned initial shape estimate; and deforming the shape model based on the aligned initial shape estimate to generate a pre-implant, morbid approximation of the bone.

According to another example, a method includes obtaining, by a computing system, image data of a joint of a patient that includes an implant, wherein the image data comprises a 3D model of the joint with the implant; identifying a first object in the 3D model, wherein the first object corresponds to a first component of the implant; determining a first vector based on the first object; identifying a second object in the 3D model, wherein the second object corresponds to a second component of the implant; determining a second vector based on the second object; determining a third vector that is normal to a plane defined by the first vector and the second vector; determining a patient coordinate system based on the first vector, the second vector, and the third vector; identifying an anatomical object in the 3D model; generating an initial aligned shape that initially aligns the anatomical object from the image data to a shape model based on the determined patient coordinate system; and generating information indicative of a morbid, pre-implant shape of the anatomical object based on the initial aligned shape.

According to another example, a method includes obtaining, by a computing system, image data of a joint of a patient; determining, by the computing system, that the joint includes an existing implant; segmenting the image data of the joint; and generating an identification of a type for the existing implant.

According to another example, a method includes obtaining, by a computing system, image data of a joint of a patient with an existing implant; identifying, by the computing system in the image data of the joint of the patient with the existing implant, an image of the existing implant; accessing, in a memory device, a database that associates a plurality of implant products with images for the plurality of implant products, each implant product of the plurality of implant products being associated with at least one image; and identifying, based on a comparison of the image of the existing implant to the images for the plurality of implant products, at least one implant product that corresponds to the existing implant.

According to another example, a method includes obtaining, by a computing system, image data of a joint of a patient with an existing implant; identifying, by the computing system, portions of the image corresponding to cement affixing a portion of the existing implant to bone; based on the portions of the image corresponding to cement, determining a cement intensity for the joint of the patient with the existing implant; and generating an output based on the determined cement intensity.

According to another example, a device includes a memory and one or more processors implemented in circuitry and configured to determine a shape model for a morbid anatomical object; obtain image data of a joint of a patient that includes an implant, wherein the image data comprises a 3D model of the joint with the implant; in the 3D model of the joint with the implant, identify voxels that correspond to a bone; based on the voxels identified as corresponding to the bone, determine an initial shape estimate for the bone; align the initial shape estimate to the shape model to form an aligned initial shape estimate; and deform the shape model based on the aligned initial shape estimate to generate a pre-implant, morbid approximation of the bone.

According to another example, a device includes a memory and one or more processors implemented in circuitry and configured to obtain image data of a joint of a patient that includes an implant, wherein the image data comprises a 3D model of the joint with the implant; identify a first object in the 3D model, wherein the first object corresponds to a first component of the implant; determine a first vector based on the first object; identify a second object in the 3D model, wherein the second object corresponds to a second component of the implant; determine a second vector based on the second object; determine a third vector that is normal to a plane defined by the first vector and the second vector; determine a patient coordinate system based on the first vector, the second vector, and the third vector; identify an anatomical object in the 3D model; generate an initial aligned shape that initially aligns the anatomical object from the image data to a shape model based on the determined patient coordinate system; and generate information indicative of a morbid, pre-implant shape of the anatomical object based on the initial aligned shape.

According to another example, a device includes a memory and one or more processors implemented in circuitry and configured to obtain image data of a joint of a patient; determine that the joint includes an existing implant;

segment the image data of the joint; and generate an identification of a type for the existing implant.

According to another example, a device includes a memory and one or more processors implemented in circuitry and configured to obtain image data of a joint of a patient with an existing implant; identify in the image data of the joint of the patient with the existing implant, an image of the existing implant; access a database that associates a plurality of implant products with images for the plurality of implant products, each implant product of the plurality of implant products being associated with at least one image; and identify, based on a comparison of the image of the existing implant to the images for the plurality of implant products, at least one implant product that corresponds to the existing implant.

According to another example, a device includes a memory and one or more processors implemented in circuitry and configured to obtain image data of a joint of a patient with an existing implant; identify portions of the image corresponding to cement affixing a portion of the existing implant to bone; based on the portions of the image corresponding to cement, determine a cement intensity for the joint of the patient with the existing implant; and generate an output based on the determined cement intensity.

According to another example, a system includes means for determining a shape model for a morbid anatomical object; means for obtaining, by a computing system, image data of a joint of a patient that includes an implant, wherein the image data comprises a 3D model of the joint with the implant; means for identifying voxels that correspond to a bone in the 3D model of the joint with the implant; means for determining an initial shape estimate for the bone based on the voxels identified as corresponding to the bone; means for aligning the initial shape estimate to the shape model to form an aligned initial shape estimate; means for deforming the shape model based on the aligned initial shape estimate to generate a pre-implant, morbid approximation of the bone.

According to another example, a system includes means for obtaining, by a computing system, image data of a joint of a patient that includes an implant, wherein the image data comprises a 3D model of the joint with the implant; means for identifying a first object in the 3D model, wherein the first object corresponds to a first component of the implant; means for determining a first vector based on the first object; means for identifying a second object in the 3D model, wherein the second object corresponds to a second component of the implant; means for determining a second vector based on the second object; means for determining a third vector that is normal to a plane defined by the first vector and the second vector; means for determining a patient coordinate system based on the first vector, the second vector, and the third vector; means for identifying an anatomical object in the 3D model; means for generating an initial aligned shape that initially aligns the anatomical object from the image data to a shape model based on the determined patient coordinate system; and means for generating information indicative of a morbid, pre-implant shape of the anatomical object based on the initial aligned shape.

According to another example, a system includes means for obtaining, by a computing system, image data of a joint of a patient; means for determining, by the computing system, that the joint includes an existing implant; means for segmenting the image data of the joint; and means for generating an identification of a type for the existing implant.

According to another example, a system includes means for obtaining, by a computing system, image data of a joint of a patient with an existing implant; means for identifying, by the computing system in the image data of the joint of the patient with the existing implant, an image of the existing implant; means for accessing, in a memory device, a database that associates a plurality of implant products with images for the plurality of implant products, each implant product of the plurality of implant products being associated with at least one image; and means for identifying, based on a comparison of the image of the existing implant to the images for the plurality of implant products, at least one implant product that corresponds to the existing implant.

According to another example, a system includes means for obtaining, by a computing system, image data of a joint of a patient with an existing implant; means for identifying, by the computing system, portions of the image corresponding to cement affixing a portion of the existing implant to bone; means for determining a cement intensity for the joint of the patient with the existing implant based on the portions of the image corresponding to cement; and means for generating an output based on the determined cement intensity.

According to another example, a computer-readable storage medium stores instructions that when executed by one or more processors cause the one or more processor to determine a shape model for a morbid anatomical object; obtain image data of a joint of a patient that includes an implant, wherein the image data comprises a 3D model of the joint with the implant; in the 3D model of the joint with the implant, identify voxels that correspond to a bone; based on the voxels identified as corresponding to the bone, determine an initial shape estimate for the bone; align the initial shape estimate to the shape model to form an aligned initial shape estimate; and deform the shape model based on the aligned initial shape estimate to generate a pre-implant, morbid approximation of the bone.

According to another example, a computer-readable storage medium stores instructions that when executed by one or more processors cause the one or more processor to obtain image data of a joint of a patient that includes an implant, wherein the image data comprises a 3D model of the joint with the implant; identify a first object in the 3D model, wherein the first object corresponds to a first component of the implant; determine a first vector based on the first object; identify a second object in the 3D model, wherein the second object corresponds to a second component of the implant; determine a second vector based on the second object; determine a third vector that is normal to a plane defined by the first vector and the second vector; determine a patient coordinate system based on the first vector, the second vector, and the third vector; identify an anatomical object in the 3D model; generate an initial aligned shape that initially aligns the anatomical object from the image data to a shape model based on the determined patient coordinate system; and generate information indicative of a morbid, pre-implant shape of the anatomical object based on the initial aligned shape.

According to another example, a computer-readable storage medium stores instructions that when executed by one or more processors cause the one or more processor to obtain image data of a joint of a patient; determine that the joint includes an existing implant; segment the image data of the joint; and generate an identification of a type for the existing implant.

According to another example, a computer-readable storage medium stores instructions that when executed by one or more processors cause the one or more processor to obtain image data of a joint of a patient with an existing implant; identify in the image data of the joint of the patient with the existing implant, an image of the existing implant; access a database that associates a plurality of implant products with images for the plurality of implant products, each implant product of the plurality of implant products being associated with at least one image; and identify, based on a comparison of the image of the existing implant to the images for the plurality of implant products, at least one implant product that corresponds to the existing implant.

According to another example, a computer-readable storage medium stores instructions that when executed by one or more processors cause the one or more processor to obtain image data of a joint of a patient with an existing implant; identify portions of the image corresponding to cement affixing a portion of the existing implant to bone; based on the portions of the image corresponding to cement, determine a cement intensity for the joint of the patient with the existing implant; and generate an output based on the determined cement intensity.

The details of various examples of the disclosure are set forth in the accompanying drawings and the description below. Various features, objects, and advantages will be apparent from the description, drawings, and claims.

BRIEF DESCRIPTION OF DRAWINGS

FIG. 28 is a flowchart illustrating an example method of operation of a computing device in accordance with one or more example techniques described in this disclosure.

FIG. 29 is a flowchart illustrating an example method of operation of a computing device in accordance with one or more example techniques described in this disclosure.

FIG. 31 is a flowchart illustrating an example method of operation of a computing device in accordance with one or more example techniques described in this disclosure.

FIG. 32 is a flowchart illustrating an example method of operation of a computing device in accordance with one or more example techniques described in this disclosure.

DETAILED DESCRIPTION

Figure 1:
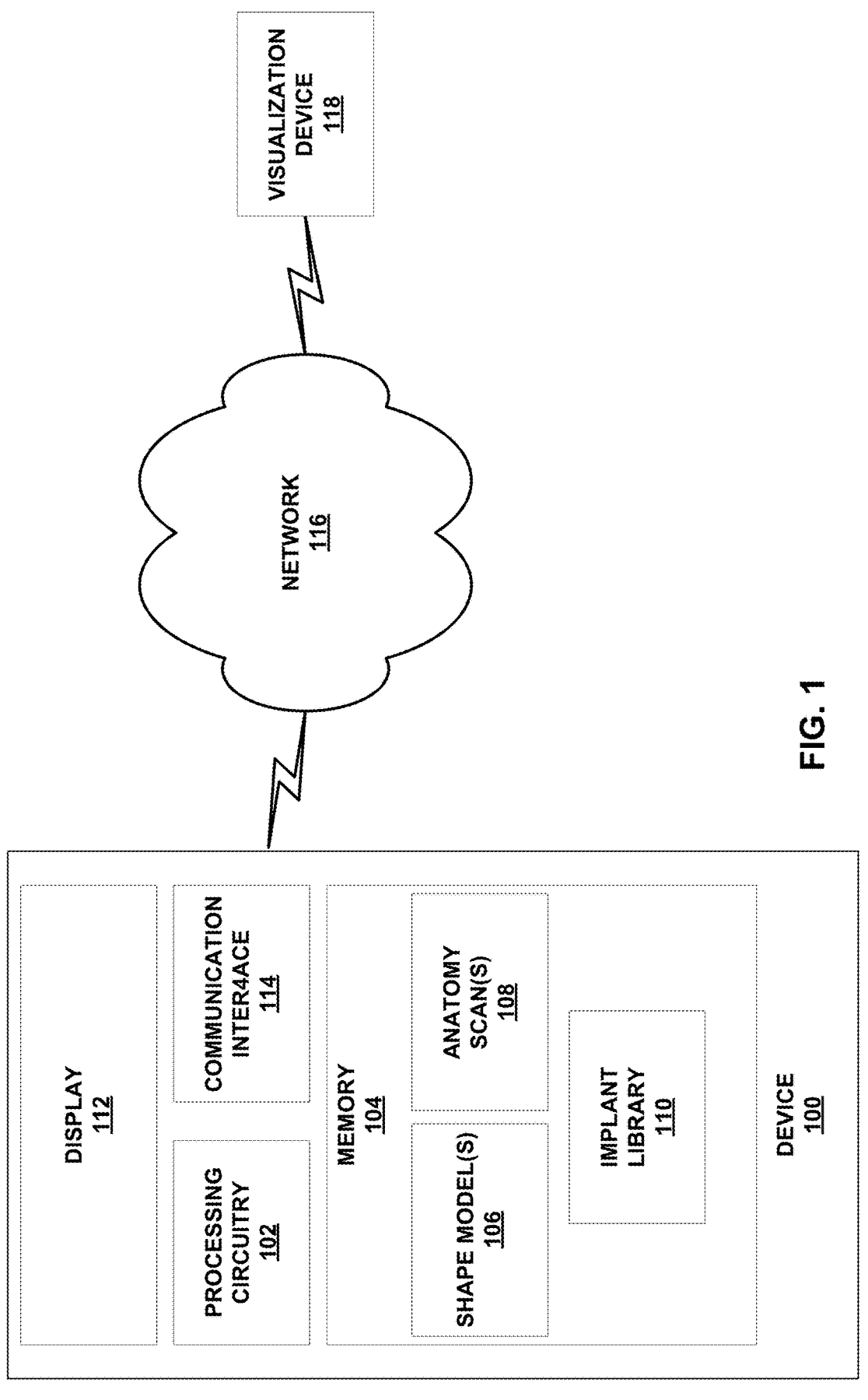
FIG. 1 is a block diagram illustrating an example computing device that may be used to implement the techniques of this disclosure.

A patient may suffer from an injury or disease (e.g., aliment) that causes damage to the patient anatomy. For shoulders, as an example of patient anatomy, a patient may suffer from primary glenoid humeral osteoarthritis (PG-HOA), rotator cuff tear arthropathy (RCTA), instability, massive rotator cuff tear (MRCT), rheumatoid arthritis (RA), post-traumatic arthritis (PTA), osteoarthritis (OA), or acute fracture, as a few examples.

To address the disease or injury, a surgeon may perform a surgical procedure such as Reversed Arthroplasty (RA), Augmented Reverse Arthroplasty (RA), Standard Total Shoulder Arthroplasty (TA), Augmented Total Shoulder Arthroplasty (TA), or Hemispherical shoulder surgery, as a few examples. There may be benefits for the surgeon to determine, prior to the surgery, characteristics (e.g., size, shape, and/or location) of the patient anatomy. For instance, determining the characteristics of the patient anatomy may aid in prosthetic selection, design and/or positioning, as well as planning of surgical steps to prepare a surface of the damaged bone to receive or interact with a prosthetic. With advance planning, the surgeon can determine, prior to surgery, rather than during surgery, steps to prepare bone or tissue, tools that will be needed during the surgery, sizes and shapes of the tools, the sizes and shapes or other characteristics of one or more protheses that will be implanted, and the like.

Placing an additional or replacement implant component into a joint that is already fitted with an existing implant component may be referred to as a revision surgery or a surgical revision procedure. Surgical revision procedures for orthopedic joints are fairly common. For instance, approximately 30% of shoulder arthroplasties are surgical revision procedures. Surgical revision procedures may be needed when a prior surgical procedure or component fails. Examples of how a procedure or component may fail include a patient with one or more implant components experiencing a trauma or other complication such as infection, a disease state progressing further to a point that an implant operation fails, or an existing implant component otherwise failing or stopping working properly. The presence of an existing implant component may correlate with a patient also having bone fractures or fragments or an otherwise deteriorated bone condition. Obtaining good imaging, segmentation, and modeling of a joint can be of particular importance in pre-operative and intra-operative planning for surgical revision procedures.

A computing device may segment image data (e.g., CT image data) of a joint to separate out individual anatomical objects so that shape and size can be visualized. The computing device may present to a doctor or other user a 3D image of the patient anatomy, including specific anatomy such as the scapula, the clavicle, the glenoid, the humerus, and the like. When obtaining image data and segmenting the image data, the presence of an existing implant, particularly a metallic implant, can potentially cause complications with the segmentation process. The implant may, for example, create noise or artifacts in the CT images that make performing segmentation difficult or make the resulting segmentation unreliable.

This disclosure describes techniques for segmenting image data representative of an orthopedic joint in which one or more implant components have been placed (e.g., for performing revision procedures). The techniques of this disclosure may help to overcome or avoid the complications created by the noise and artifacts caused by implants and enable a computing device to produce a useful segmentation of a joint, even when the joint includes an implant component. Furthermore, this disclosure describes techniques that may enable a device to obtain, from acquired image data, information regarding the one or more existing implant components and the joint. The device may alternatively or additionally prepare a surgical revision procedure plan for revision to replace the existing implant components with one or more new implant components.

In some examples, the techniques may enable a computing device to provide intra-operative surgical guidance to a surgeon or surgical team to perform a surgical revision procedure based on the information. Thus, the techniques of this disclosure may improve existing computing devices by enabling computing devices to support better pre-operative and/or intra-operative surgical planning and guidance for surgical revision procedures. This better surgical planning and/or guidance may take the form of improved segmentation of a joint with an existing implant but may also take the form of more reliable surgical classifications and/or recommendations, such as automated classifications of existing implant components and automated recommendations to a surgeon related to procedure types and implant types for surgical revision to replace such existing implant components.

The techniques of this disclosure may provide better pre-operative and intra-operative surgical guidance for revision surgeries by enabling a computing device to present to a doctor, nurse, patient, or other user, via a display, various types of 2D and/or 3D images that can aid in pre-operative planning as well as intra-operative decision making. In some examples, a computing device may be configured to generate images that either show multiple parts of a joint and/or images that separate out the various parts of the joint. Despite the presence of an existing implant, the computing device may be configured to generate an image that shows the joint (either in its post-morbid state or a pre-morbid approximation) as if the implant is not present. In other examples, the computing device may be configured to generate images that either show the existing implant or otherwise annotate an image to signify the existence of the implant.

Pre-morbid anatomy, also called native anatomy, refers to the anatomy prior to the onset of a disease or the occurrence of an injury. Even after disease or injury, there may be portions of the anatomy that are healthy and portions of the anatomy that are not healthy (e.g., diseased or damaged). The diseased or damaged portions of the anatomy are referred to as pathological anatomy, and the healthy portions of the anatomy are referred to as non-pathological anatomy.

As used in this disclosure, a pre-morbid characterization refers to characterizing the patient anatomy as it existed prior to the patient suffering disease or injury and hence, also prior to implantation of an implant. A pre-morbid characterization of the anatomy is often not available because the patient typically does not consult with a doctor or surgeon until after that anatomy is already diseased or injured. As used in this disclosure, a morbid, pre-implant characterization refers to characterizing the patient anatomy as it existed prior to the patient having the implant implanted but after suffering disease or injury. As used in this disclosure, a post-implant characterization refers to characterizing the patient anatomy as it exists after having the implant implanted.

FIG. 1 is a block diagram illustrating an example computing device that may be used to implement the techniques of this disclosure. FIG. 1 illustrates device 100, which is an example of a computing device configured to perform one or more example techniques described in this disclosure.

Device 100 may include various types of computing devices, such as server computers, personal computers, smartphones, laptop computers, and other types of computing devices. Device 100 includes processing circuitry 102, memory 104, and display 112. Display 112 is optional, such as in examples where device 100 is a server computer.

Examples of processing circuitry 102 include one or more microprocessors, digital signal processors (DSPs), application specific integrated circuits (ASICs), field programmable gate arrays (FPGAs), discrete logic, software, hardware, firmware or any combinations thereof. In general, processing circuitry 102 may be implemented as fixed-function circuits, programmable circuits, or a combination thereof. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits.

Processing circuitry 102 may include arithmetic logic units (ALUs), elementary function units (EFUs), digital circuits, analog circuits, and/or programmable cores, formed from programmable circuits. In examples where the operations of processing circuitry 102 are performed using software executed by the programmable circuits, memory 104 may store the object code of the software that processing circuitry 102 receives and executes, or another memory within processing circuitry 102 (not shown) may store such instructions. Examples of the software include software designed for surgical planning.

Memory 104 may be formed by any of a variety of memory devices, such as dynamic random access memory (DRAM), including synchronous DRAM (SDRAM), magnetoresistive RAM (MRAM), resistive RAM (RRAM), or other types of memory devices. Examples of display 112 include a liquid crystal display (LCD), a plasma display, an organic light emitting diode (OLED) display, or another type of display device.

Device 100 may include communication interface 114 that allows device 100 to output data and instructions to and receive data and instructions from visualization device 118 via network 116. For example, after determining a premorbid characteristic of the anatomical object, using techniques described in this disclosure, communication interface 114 may output information of the pre-morbid characteristic to visualization device 118 via network 116. A surgeon may then view a graphical representation of an anatomical object with visualization device 118. The viewed anatomical object may be any of a pre-morbid anatomical object, a pre-implant morbid anatomical objects, or a post-implant anatomical object. In some examples, visualization device 118 may present, for example, the pre-implant morbid anatomical object or post-implant anatomical object overlaid on top of image of the injured or diseased anatomical object. By overlaying images from different times, a doctor or surgeon may be able to more easily observe the deterioration of the anatomical object.

Communication interface 114 may be hardware circuitry that enables device 100 to communicate (e.g., wirelessly or using wires) to other computing systems and devices, such as visualization device 118. Network 116 may include various types of communication networks including one or more wide-area networks, such as the Internet, local area networks, and so on. In some examples, network 116 may include wired and/or wireless communication links.

Visualization device 118 may utilize various visualization techniques to display image content to a surgeon. Visualization device 118 may be a mixed reality (MR) visualization device, virtual reality (VR) visualization device, holographic projector, or other device for presenting extended reality (XR) visualizations. In some examples, visualization device 118 may be a Microsoft HOLOLENS™ headset, available from Microsoft Corporation, of Redmond, Washington, USA, or a similar device, such as, for example, a similar MR visualization device that includes waveguides. The HOLOLENS™ device can be used to present 3D virtual objects via holographic lenses, or waveguides, while permitting a user to view actual objects in a real-world scene, i.e., in a real-world environment, through the holographic lenses.

Visualization device 118 may utilize visualization tools that are available to utilize patient image data to generate three-dimensional models of bone contours to facilitate preoperative planning for joint repairs and replacements. These tools allow surgeons to design and/or select surgical guides and implant components that closely match the patient's anatomy. These tools can improve surgical outcomes by customizing a surgical plan for each patient. An example of such a visualization tool for shoulder repairs is the BLUEPRINT™ system available from Wright Medical Technology, Inc. The BLUEPRINT™ system provides the surgeon with two-dimensional planar views of the bone repair region as well as a three-dimensional virtual model of the repair region. The surgeon can use the BLUEPRINT™ system to select, design or modify appropriate implant components, determine how best to position and orient the implant components and how to shape the surface of the bone to receive the components, and design, select or modify surgical guide tool(s) or instruments to carry out the surgical plan. The information generated by the BLUEPRINT™ system is compiled in a preoperative surgical plan for the patient that is stored in a database at an appropriate location (e.g., on a server in a wide area network, a local area network, or a global network) where it can be accessed by the surgeon or other care provider, including before and during the actual surgery.

As illustrated, memory 104 stores data representative of shape models 106, data representative of anatomy scans 108, and implant library 110. Although shape models 106, data representative of anatomy scans 108, and implant library 110 are shown in the example of FIG. 1 as being stored locally on device 100, in other examples, the content of shape models 106, data representative of anatomy scans 108, and implant library 110 may be stored remotely and accessed, for example, via network 116.

Anatomy scans 108 are examples of computed tomography (CT) scans of a patient, e.g., as represented by CT scan image data. Anatomy scans 108 may be sufficient to construct a three-dimensional (3D) representation of the anatomy of the patient, such as the scapula and glenoid, by either automated or manual segmentation of the CT image data to yield segmented anatomical objects. One example implementation of automated segmentation is described in U.S. Pat. No. 8,971,606. There may be various other ways in which to perform automated segmentation, and the techniques are not limited to automated segmentation using techniques described in U.S. Pat. No. 8,971,606. As one example, segmentation of the CT image data to yield segmented objects includes comparisons of voxel intensity in the image data to determine bony anatomy and comparisons to estimated sizes of bony anatomy to determine a segmented object. Moreover, the example techniques may be performed with non-automated segmentation techniques, where a medical professional evaluates the CT image data to segment anatomical objects, or some combination of automation and user input for segmenting anatomical objects. U.S. Provisional Patent Application 62/826,119, filed 29

Mar. 2019, and U.S. Provisional Patent Application 62/826,190, filed 29 Mar. 2019, describe aspects of segmentation and are both hereby incorporated by reference in their entirety.

In one or more examples, anatomy scans 108 may be scans of anatomy that include implants, and hence, are pathological due to injury or disease. The patient may have an injured shoulder requiring a revision procedure, and for the procedure or possibly as part of the diagnosis, the surgeon may have requested anatomy scans 108 to plan the surgery. A computing device (like device 100 or some other device) may generate segmentations of the patient anatomy so that the surgeon can view anatomical objects and the size, shape, and interconnection of the objects with other anatomy of the patient anatomy needing surgery.

As will be explained in more detail below, processing circuitry 102 may utilize image data of scans 108 to compare (e.g., size, shape, orientation, etc.) against a statistical shape model (SSM) as a way to determine characteristics of the patient anatomy prior to the patient suffering the injury or disease or after suffering the injury or disease but before having an implant installed. In other words, for revision, the patient may have an injured or diseased bone for which an implant was implanted, and then for the revision procedure, processing circuitry 102 determines the characteristics of the bone having the injury or disease at the time the implant was implanted. The characteristics of the injured or diseased bone, prior to implant, may assist the surgeon in performing the revision procedure. The SSM may represent either models of pre-morbid anatomy or models of diseased, but pre-implant, anatomy. In some examples, processing circuitry 102 may compare 3D point data of non-pathological points of anatomical objects of patient anatomy in the image data of scans 108 to points in the SSM.

For instance, scans 108 provide the surgeon with a view of the current characteristics of the damaged or diseased anatomy, including the implant if an implant is installed. To reconstruct the anatomy (i.e., to represent a pre-morbid state or morbid, pre-implant state), the surgeon may find it beneficial to have a model indicating the characteristics of the anatomy prior to the injury or disease and/or prior to the implant. For instance, the model may be a predictor of the anatomy of the patient prior to damage or disease and/or prior to implantation of the implant. As it may be likely the patient did not consult with the surgeon until after the injury occurred or disease progressed, a model of the patient anatomy prior to the injury or disease (e.g., pre-morbid or native anatomy) may not be available. Similarly, even if a patient did consult with the surgeon prior to having an implant installed, a model of the patient anatomy prior to the installation of the implant may not be available due to the procedure being performed a long time ago, the procedure being performed by a different surgeon or health care service, or for numerous other reasons. Using the SSM as a way to model the pre-morbid and/or morbid, pre-implant anatomy allows the surgeon to determine characteristics of the patient anatomy that can no longer be determined simply by viewing anatomy scans alone. As will be explained in greater detail below, using SSM in conjunction with revision procedures presents unique challenges, and this disclosure describes techniques that may improve the ability of the devices to provide image data to a surgeon and to provide surgical guidance.

Implant library 110 represents a database of known implants. For each known implant, implant library 110 may store an indication of a manufacturer for the implant, a model for the implant, surgical techniques needed to install or remove the implant, countries in which the implant was publicly available and date ranges for when the implant was publicly available in those countries, and other such information for the known implants. For each known implant, implant library 110 may also store information about the implant such as a type for the implant (e.g., anatomic, reverse, etc.), affixing methods for the implant (e.g., cemented, screwed, etc.), available sizes for the implant, and so on. For each implant, implant library 110 may also store removal information, such as an indication of tools needed to remove the implant and instructions for removing the implant. Implant library 110 may also store associated 2D and/or 3D images for each known implant.

As will be explained in more detail below, as part of planning an implant removal operation, processing circuitry 102 may determine, by using known information about a patient implant and image data of the patient implant, which implant from implant library 110 corresponds to the patient's implant. Thus, processing circuitry 102 may output information such as removal information for the implant being removed from the patient as part of the surgery. Based on the determined removal information, a surgeon may be able to do better pre-operative planning for implant removal by, for example, knowing in advance of an operation what tools are needed to remove a particular implant and how long a removal may be expected to take.

When encountering a revision case, processing circuitry 102 may implement different processing techniques than for non-revision cases. Processing circuitry 102 may, for example, determine if a particular case is a revision case based on a user input from a member of a surgical team or other user or based on stored information in a patient profile. In some instances, however, such as cases where a patient has experienced a trauma and is non-responsive, a user of device 100 may not know if the patient already has an implant installed, in which case processing circuitry 102 may determine that a case is a revision case based on anatomy scans 108.

For a revision case where a patient has an existing implant installed in or proximal to a joint, processing circuitry 102 of device 100 may be configured to obtain, from memory 104, anatomy scans 108. Processing circuitry 102 may be configured to determine that the joint includes the implant based on anatomy scans 108 or based on a user input. Processing circuitry 102 may, for example, present to a user of device 100 an inquiry asking the user whether the joint of the patient includes an implant, and the user of device 100 may be able to respond to the inquiry with an answer of yes, no, or unknown. In other examples, processing circuitry 102 may be configured to determine that the joint includes the implant by extracting such information from medical records stored in memory 104 or from medical records that are stored remotely from device 100, but which are otherwise accessible to device 100, via a network connection, for example.

Alternatively or additionally, processing circuitry 102 may be configured to determine the presence of an implant based on the image data by performing image analysis of the image data for anatomy scans 108. It should be understood that image data, in this context, includes both display images and raw image data associated with anatomy scans 108. In this context, raw image data refers to image data that is used to determine display images. Raw image data may have a different resolution, bit-depth, or dynamic range than a display image and may additionally be in a different color space or color model. In general, raw image data includes data that is captured as part of the imaging, including data used by display 112 or visualization device 118 to display the images and in some examples, even data that is not directly used by display 112 or visualization device 118 to display images. For example, raw image data, in the context of this disclosure, may include data not traditionally even thought of as being image data. As one example, in CT image data, pixels are associated with a relative radiodensity value corresponding to a mean attenuation, as measured in Hounsfield units (HUs) using the Hounsfield scale. These HU values are an example of raw image data. A display device converts the HU values into gray scale for display. Unless otherwise stated, it should be assumed that techniques of this disclosure that are described as being performed on image data can be performed using either display images or raw images.

Additionally, it should be understood that image data in this disclosure refers to both 2D and 3D image data. For simplicity, certain techniques will be described as being performed on pixels, which represent a location within a 2D model, but unless stated otherwise, it should be assumed those techniques can also be performed on voxels, which represent a location within a 3D model. Similarly, unless stated otherwise, it should be assumed that techniques described as being performed on voxels may also be performed on pixels.

Processing circuitry 102 may determine the presence of the implant using intensity thresholding on raw image date of anatomy scans 108. When imaged using a CT scan, different materials produce pixels of different intensity. As measured in HUs, for instance, water has a value of approximately 0; air has a value of approximately −1000; cortical bone ranges from 200 to 500; and metallic implants usually have an intensity over 1000. In some instances, implants may be cemented in place using a bone cement that affixes the implant to the bone. The bone cement may also produce pixels of a unique intensity. For example, in a CT scan, polymethylmethacrylate (PMMA) bone cement generally produces voxels that have an expected intensity of 1423±70, although other types of cements may have different intensities. Pixels with similar intensities generally belong to the same object (e.g., soft tissue, bone, implant, cement).

By determining the pixel intensities, processing circuitry 102 can categorize objects in an image as belonging to either bone, soft tissue, implant component, cement, or some other category. As will be explained in more detail below, some pixels may also be categorized as either being noise or otherwise indeterminable. By performing pattern matching and shape analysis on the objects, using techniques described in this disclosure, processing circuitry 102 may further categorize the objects, for example, as belonging to a specific bone or specific component of an implant. For example, for an object in an image that corresponds to bone, processing circuitry 102 may analyze the shape of the object to determine if the bone is a humerus, a glenoid, or some other bone. Similarly, for an object in an image that corresponds to an implant component, processing circuitry 102 may analyze the shape of the object to determine if the implant component is a stem, a glenoid prosthesis, a humeral prosthesis, or some other component of an implant.

Figure 2:
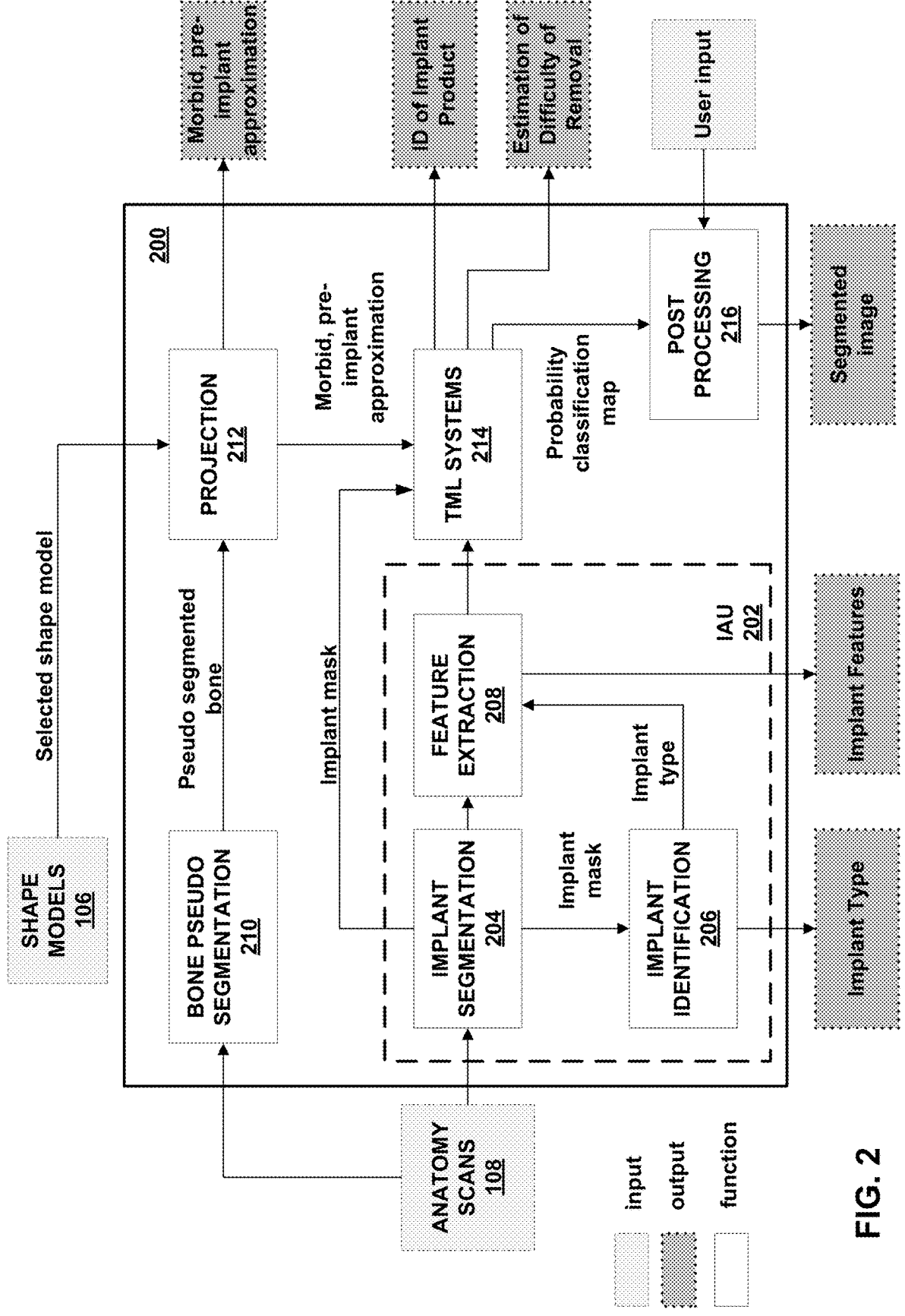
FIG. 2 shows an example implementation of a revision unit.

FIG. 2 shows revision unit 200. Revision unit 200 of FIG. 2 may, for example, be a component of device 100 of FIG. 1 that is included within processing circuitry 102. Revision unit 200 includes implant analysis unit (IAU) 202, which includes implant segmentation unit 204, implant identification unit 206, and feature extrication unit 208. Revision unit 200 also includes bone pseudo segmentation unit 210, projection unit 212, trained machine learning (TML) system 214, and post processing unit 216.

Implant segmentation unit 204 receives anatomy scans 108, which include CT scans of a joint with an implant. The CT scans may collectively form a 3D model of the joint with the implant. Implant segmentation unit 204 segments the 3D model to isolate the implant by identifying voxels of the 3D model that have HU values indicative of corresponding to implant. As HU values for metallic implants are usually over 1000 and HU values for cortical bone, connective tissue, and other parts of a joint are substantially lower, implant segmentation unit 204 may, for example, classify voxels with HU values over 1000, or some other threshold level, as corresponding to implant components and voxels with HU values under 1000 as corresponding to non-implant components.

The CT scans includes voxels that correspond to the implant. In some cases, the implants create noise at locations outside of where the implant is located and that overlap with the patient anatomy in the CT scans. The noise in CT scans produced by metallic implants tends to have HU values substantially below that of the voxels that correspond to the metallic implant.

As the voxels that correspond to the implant have a high HU, processing circuitry 102 may be configured to accurately identify the implant based on the HU thresholding. However, because the voxels resulting from the noise generated by the implant, where such voxels from the noise are intermingled with voxels of the patient anatomy, have a much lower HU values, processing circuitry 102 may not easily classify a voxel as belonging to patient anatomy or belonging to the noise generated in the image due to the implant. Therefore, noise does not typically complicate the process of segmenting the 3D model to isolate the implant in the same way noise complicates segmenting the 3D model to isolate bone. The isolated voxels corresponding to implant determined by implant segmentation unit 204 may be referred to as an implant mask. The implant mask represents a 3D model where all voxels not corresponding to implant are set to a common value distinct from the values of those voxels that correspond to non-implant. Thus, the implant mask isolates, in the 3D model, the implant from everything else that is not implant.

Figure 3A:
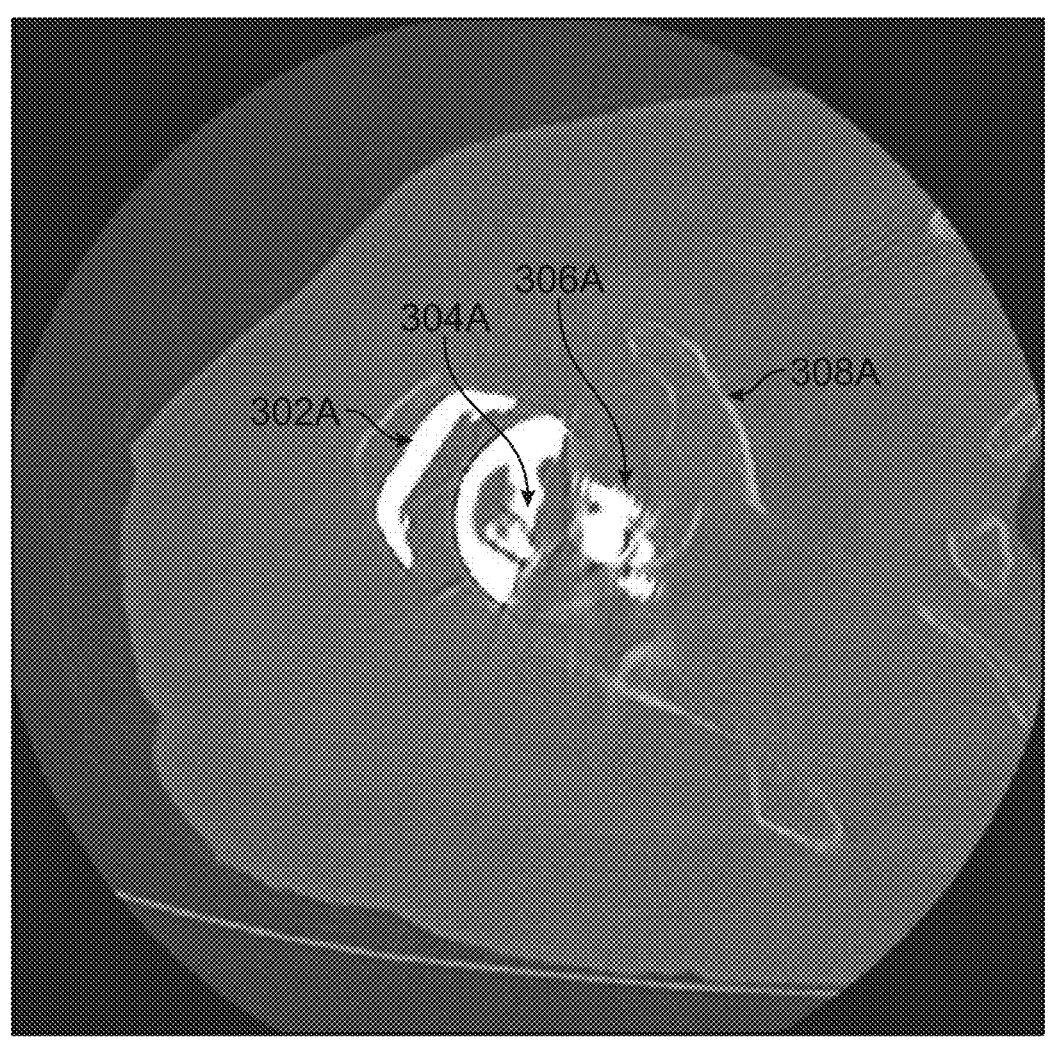
FIG. 3A shows an axial slice of a computerized tomography (CT) scan for a shoulder joint that includes a reverse implant.

FIG. 3A shows an axial slice of a CT scan for a shoulder joint that includes a reverse implant. Thus, FIG. 3A represents a 2D slice of the 3D model of the joint that may, for example, be included within anatomy scans 108. The axial scan of FIG. 3A shows a humeral cap component (302A), a glenoid sphere component (304A), and screws (306A) that attach the glenoid sphere component to the scapula. FIG. 3A also shows bone (e.g., 308A and elsewhere) and other aspects of the joint.

Figure 3B:
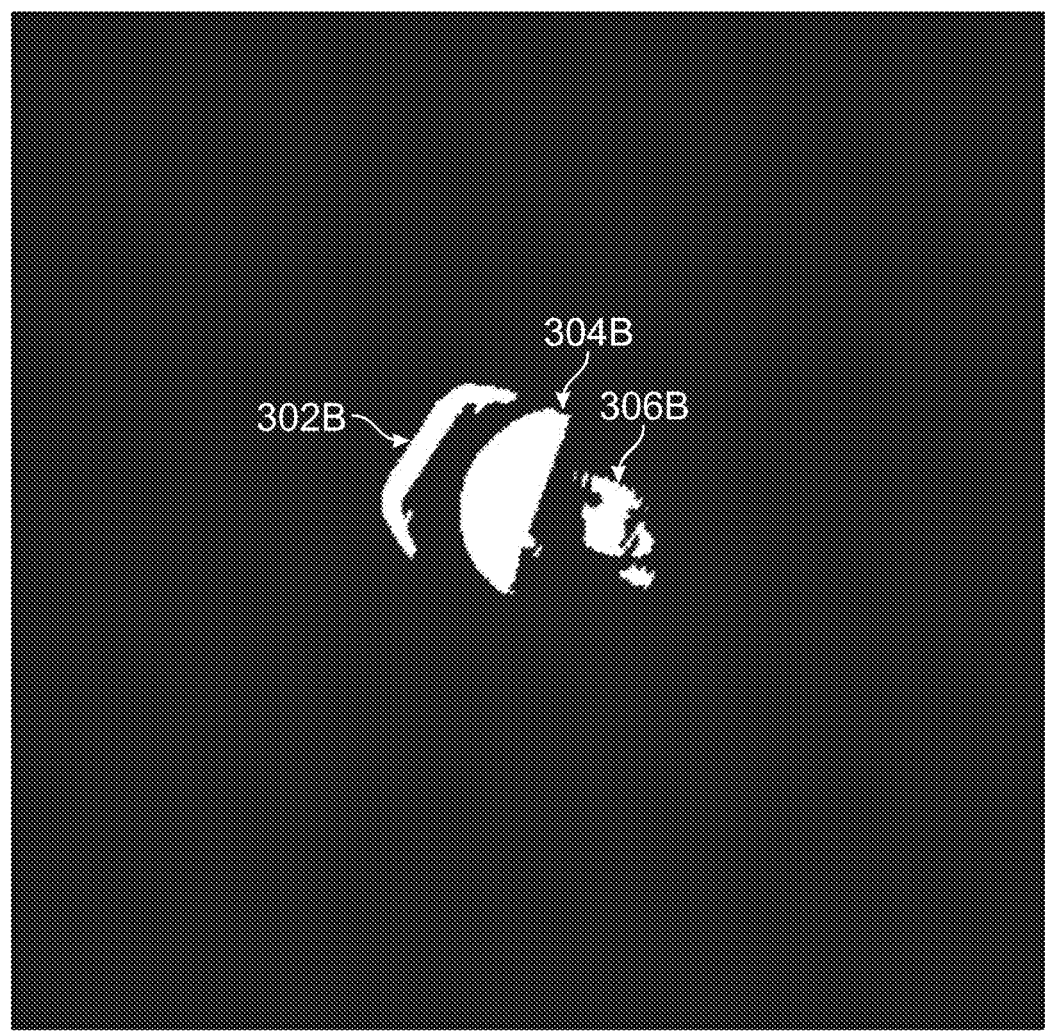
FIG. 3B shows the implant of FIG. 3A after segmentation to isolate the implant components.

FIG. 3B shows the implant of FIG. 3A after segmentation to isolate the implant. Thus, FIG. 3B shows an axial scan of the implant mask and shows the humeral cap component (302B), the glenoid sphere component (304B), and the screws (306B) that attach glenoid sphere component 304B to the scapula. All the other non-implant pixels of FIG. 3A, however, are set to a constant value in FIG. 3B that highly contrasts with the implant components. FIG. 3B represents a 2D example of an implant mask generated by implant segmentation unit 204.

Implant identification unit 206 determines a type for the implant based on the implant mask determined by implant segmentation unit 204 and outputs the type for the implant to a user. In this context, a type for the implant refers to, for example, a hemisphere implant type, a reverse implant type, or an anatomic implant type. As will be explained in more detail with respect to FIG. 4, implant identification unit 206 may determine the type of the implant based on a number of unconnected objects in the implant mask determined by implant segmentation unit 204.

As will be explained in more detail with respect to FIG. 4, feature extraction unit 208 analyzes the segmented image of the implant, i.e., the implant mask, to determine features of the implant, such as the geometric center of the implant sphere, which may serve as an approximation for a center of the glenoid.

Figure 4:
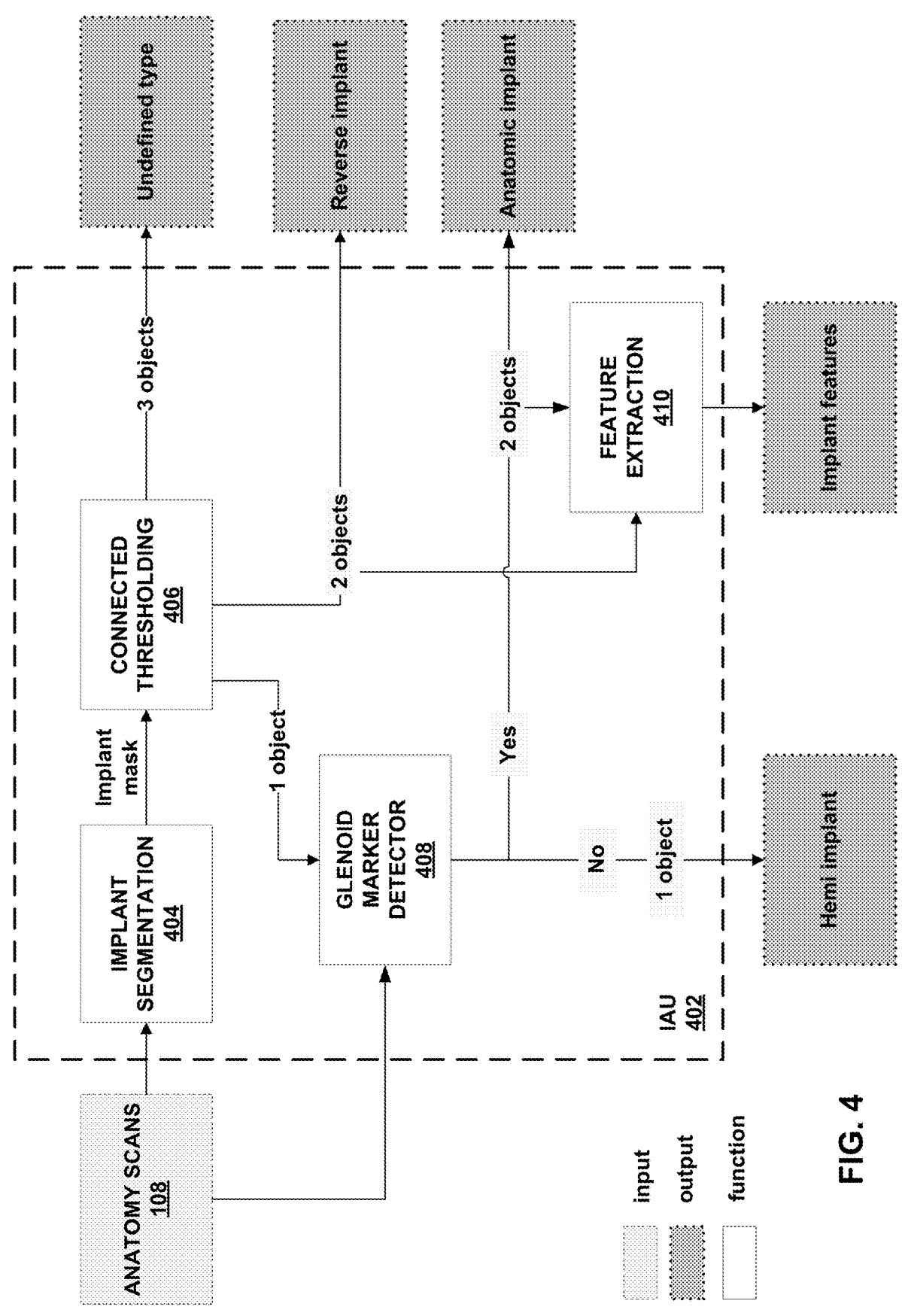
FIG. 4 shows an example of an implant analysis unit.

FIG. 4 shows IAU 402, which represents one example implementation of IAU 202 in FIG. 2. IAU 402 includes implant segmentation unit 404, connected thresholding unit 406, glenoid marker detection unit 408, and feature extraction unit 410. Implant segmentation unit 404 generally operates in the same manner as described for implant segmentation unit 204 of FIG. 2 and determines an implant mask.

Based on the determined implant mask, connected thresholding unit 406 determines a number of unconnected objects within the implant mask. Connected thresholding unit 406 identifies, for example, groups of adjacent voxels that have HU values corresponding to implant. A group of adjacent voxels corresponding to implant completely surrounded by voxels corresponding to non-implant is being referred to herein as an object. A first group of voxels corresponding to implant that are completely surrounded by voxels corresponding to non-implant and a second group of voxels corresponding to implant completely surrounded by voxels corresponding to non implant constitute first and second objects respectively. If none of the first group of voxels corresponding to implant are adjacent to any of the second group of voxels corresponding to implant, then the first and second objects are considered to be unconnected objects. That is, there is patient anatomy between the first and second objects, and therefore unconnected. In order to not identify extraneous voxels or groups of voxels as being unconnected objects, connected thresholding unit 406 may only identify as objects those groups of voxels that have a certain shape or minimum size.

If connected thresholding unit 406 determines that the implant mask includes three unconnected objects, then connected thresholding unit 406 determines that a type for the existing implant comprises an undefined type, meaning the type is unknown. If connected thresholding unit 406 determines that the implant mask includes two unconnected objects, then connected thresholding unit 406 determines that a type for the existing implant comprises a reverse type implant. As the glenoid implant component for an anatomic implant is typically not predominantly metallic, connected thresholding unit 406 may not detect an object for a glenoid implant as being present in the implant mask. By contrast, for a reverse implant, both humeral implant component and the glenoid implant component are predominantly metallic. FIG. 3B, for example, shows two unconnected objects, the first object being humeral cap component (302B) and the second object being glenoid sphere component (304B) and screws (306B). Although glenoid sphere component 304B and screws 306B appear to be separate objects in the axial scan of FIG. 3B, in the actual 3D model those two components would be a common object.

Figure 5:
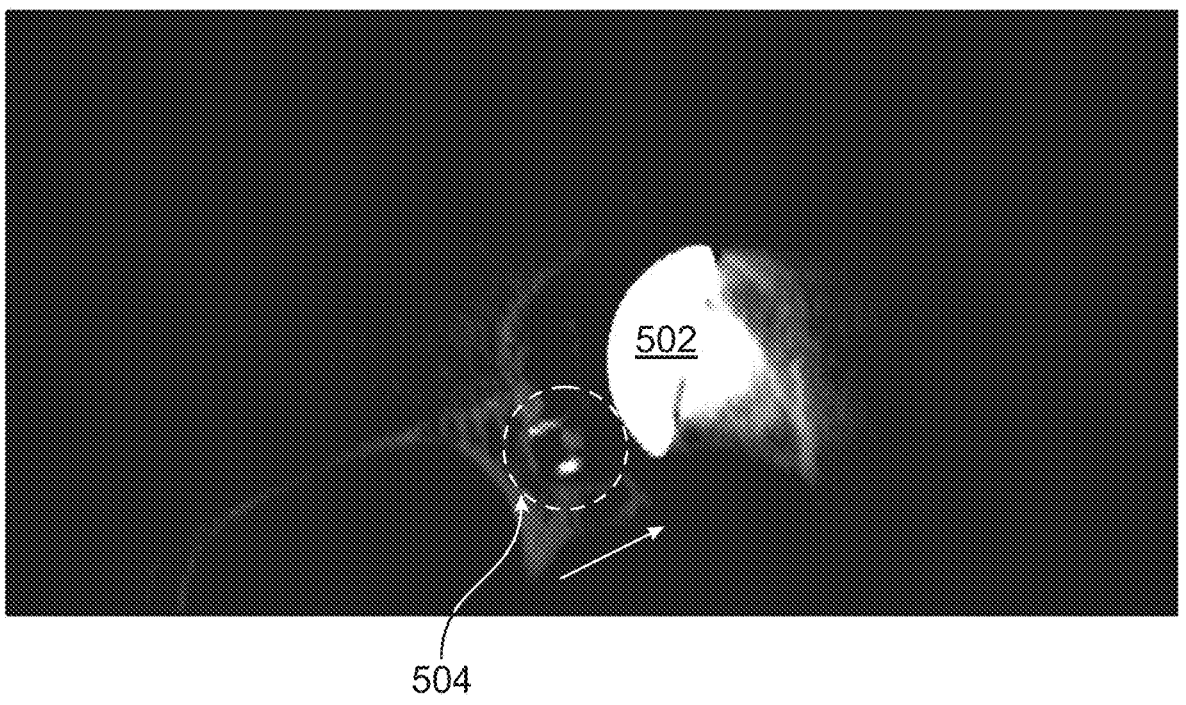
FIG. 5 shows an axial slice of a CT scan for a shoulder joint that includes an anatomic implant.

FIG. 5 shows an axial slice of a CT scan for a shoulder joint that includes an anatomic implant. FIG. 5 shows spherical humeral implant component 502 and shows glenoid markers 504. Glenoid markers 504 are small components within a larger glenoid implant component. As most of the larger glenoid implant component is non-metallic, the larger glenoid implant component is not easily discernible in the CT scan.

If connected thresholding unit 406 detects one object, then glenoid marker detector 408 may search a second search location for the presence of glenoid markers. The second search location may, for example, be a reduced region, within the unsegmented 3D model, identified based on proximity to the one detected object. For example, glenoid marker detector 408 may be configured to only search radially outward from the spherical surface of humeral implant 502, which generally corresponds to the area to the left of humeral implant 502 in FIG. 5. Glenoid marker detector 408 may not need to search the region radially inward from humeral implant component 502, which generally corresponds to the region to the right of humeral implant 502 in FIG. 5. For a hemisphere implant, a patient also has a humerus-side, spherically-shaped implant component, but unlike an anatomical implant, the hemi implant does not include a scapula-side implant component, instead using the patient's natural bone to receive the humerus-side implant component.

Despite being predominantly non-metallic, glenoid implant components include metallic markers, such as markers 504 in FIG. 5. The metallic markers are, for example, strips of metal that may show up as approximately straight lines or thin rectangles on an axial scan of a CT image. The straight lines are typically used by a surgeon to determine or monitor the orientation of the glenoid component and to determine if the orientation changes over time.

If glenoid marker detection unit 408 determines that the second search location includes voxels that correspond to metal, and thus are indicative of glenoid markers, then glenoid marker detector unit 408 may determine that an implant type for the implant is an anatomic implant type. If glenoid marker detection unit 408 determines that the second search location does not include voxels that correspond to metal, and thus are indicative of glenoid markers, then glenoid marker detector unit 408 may determine that an implant type for the implant is a hemi implant type. The absence of glenoid markers means the patient does not have a scapula-side implant component, which corresponds to a hemi implants which do not require alterations to a patient's scapula.

As glenoid markers tend to be relatively small, and thus include less metal, glenoid markers typically do not cause the same intensity within a CT scan and do not produce objects that are particularly large. Accordingly, when identifying glenoid markers, glenoid marker detection unit 408 may utilize different intensity thresholds and size thresholds than those used by connected thresholding unit 406 when determining the number of unconnected objects.

Feature extraction unit 410 may be configured to determine features of the implant based on the implant type and the implant mask. As will be explained in more detail below, feature extraction unit 410 may be configured to determine a patient coordinate system that can be used for determining a morbid, pre-implant approximation of a bone using SSM.

Figure 6:
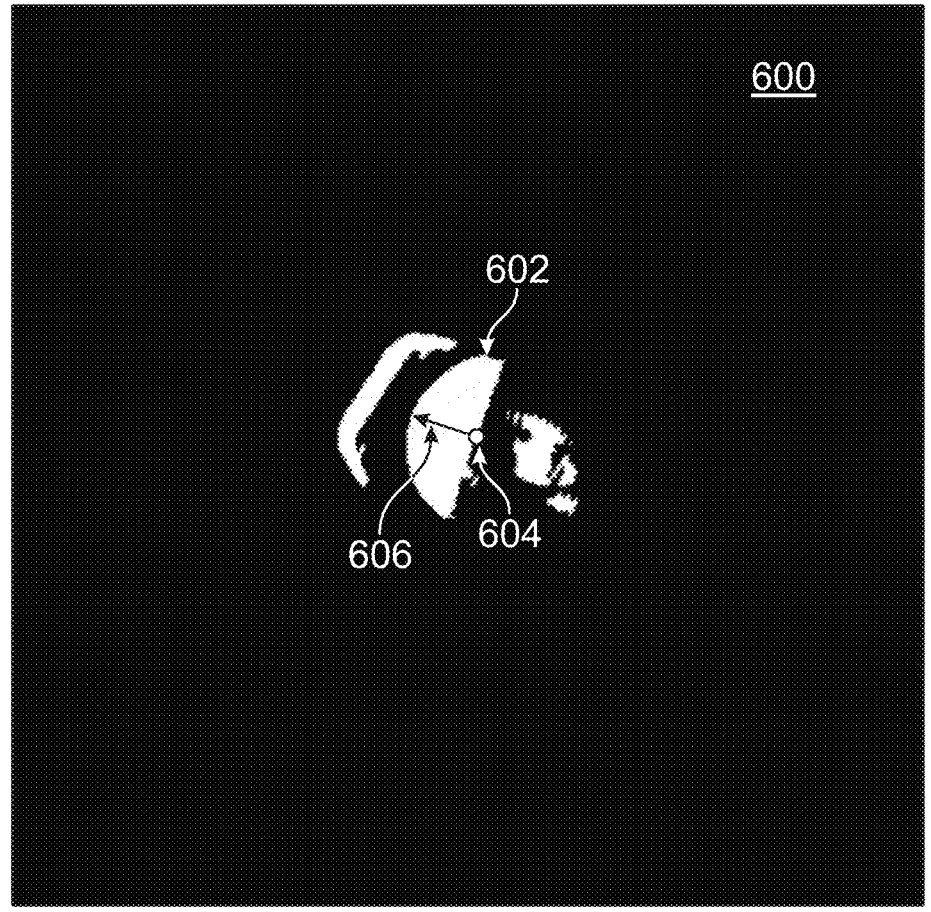
FIG. 6 is a diagram illustrating how feature extraction may be performed on the segmented image of FIG. 3B.

FIG. 6 is a diagram illustrating how feature extraction may be performed on a segmented image isolating the implant components for a reverse implant. FIG. 6 shows axial slice 600 of a segmented image. Axial slice 600 may, for example, be a slice of the 3D implant mask determined by implant segmentation unit 204 or implant segmentation unit 404. Axial slice 600 shows glenoid sphere 602, coordinate system center 604, and vector 606. For reverse implants, feature extraction unit 410 may be configured to locate a partially spherical object, i.e., a group of voxels in the implant mask, corresponding to a glenoid sphere using pattern matching. The partially spherical object may have, for example, a spherical surface and a flat circular surface. Feature extraction unit 410 may identify a central location on the flat circular surface as a coordinate system center (604 in FIG. 6). Feature extraction unit 410 may identify a vector (606 in FIG. 6) that is orthogonal to the flat circular surface.

Figure 7A:
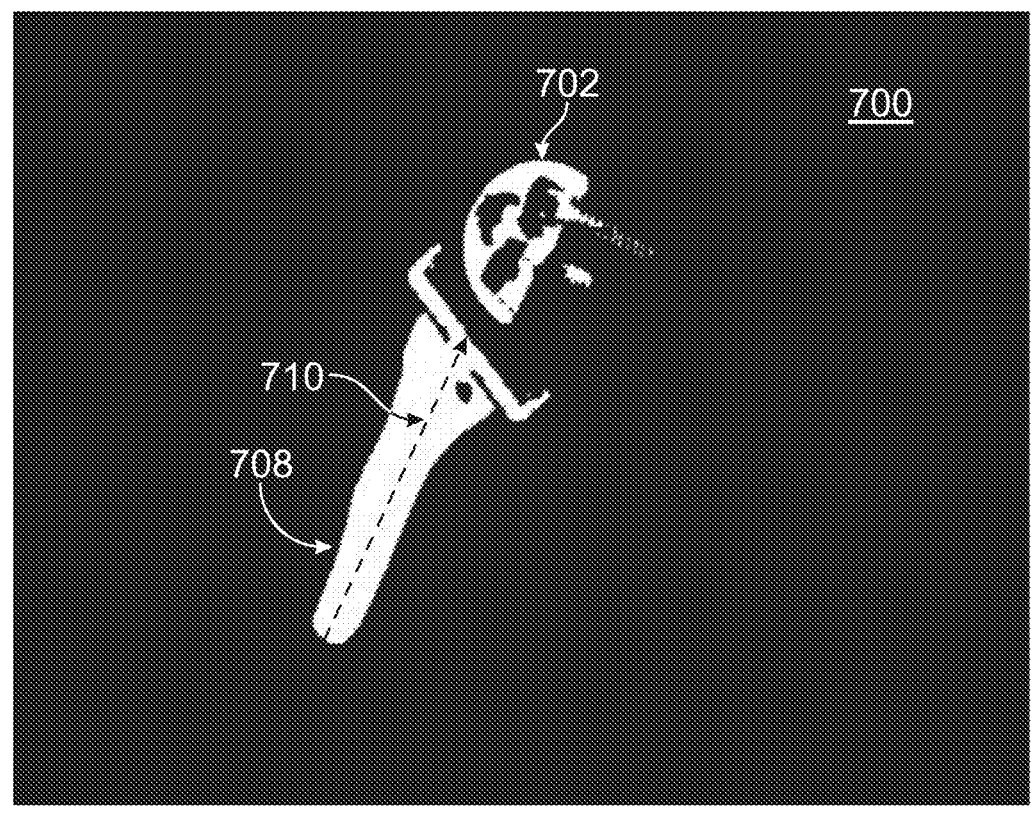
FIGS. 7A and 7B are diagrams illustrating how feature extraction may be performed on a segmented image isolating the implant components for an anatomical implant.
Figure 7B:
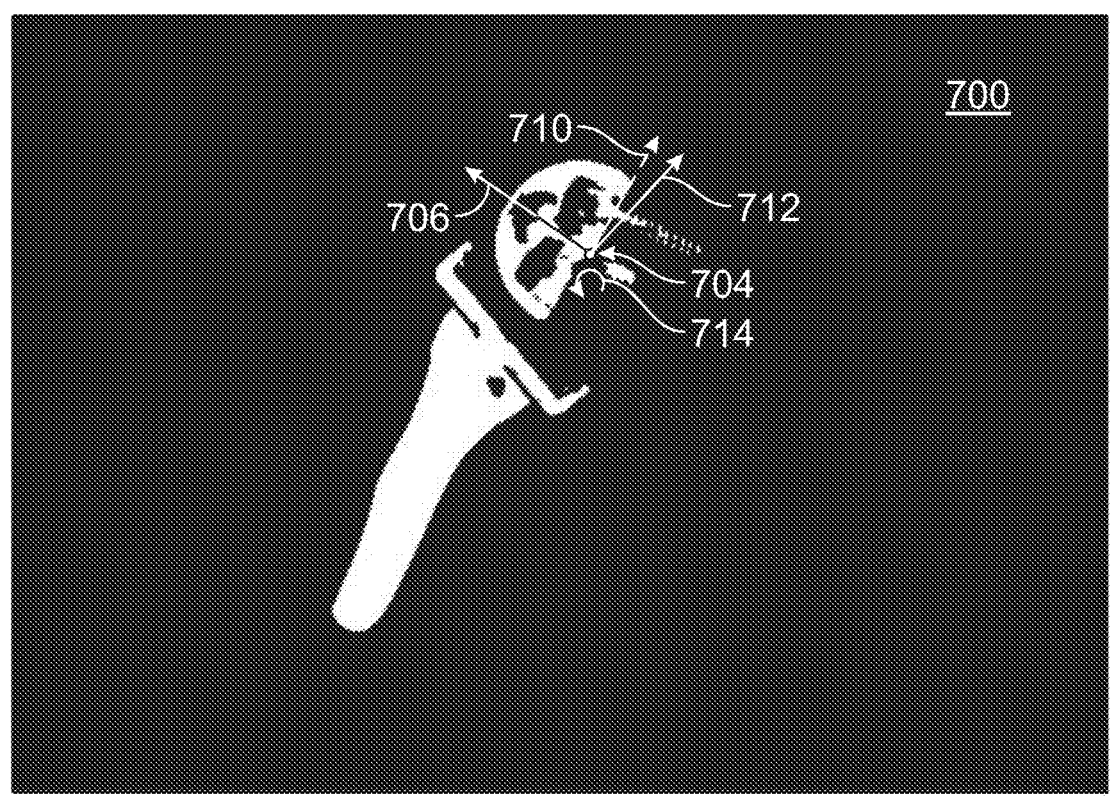

FIGS. 7A and 7B are additional diagrams illustrating how feature extraction may be performed on a segmented image isolating the implant components for an a reverse implant. FIG. 7A shows axial slice 700 of a segmented image. Axial slice 700 may, for example, be a slice of the 3D implant mask determined by implant segmentation unit 204 or implant segmentation unit 404. Axial slice 700 shows glenoid sphere 702 and humeral stem 708. For reverse implants, feature extraction unit 410 may be configured to locate a group of voxels in the implant mask corresponding to a humeral stem (708 in FIG. 7A). Feature extraction unit 410 may identify the humeral stem by searching the implant mask for an elongated object using pattern matching. In this context, an elongated objected generally refers to an object where one dimension, such as length, is significantly larger than the other dimensions, such as width or depth. For the elongated object, feature extraction unit 410 may be configured to determine a vector (710 in FIG. 7A) that points from a distal end of humeral stem 708 to a proximal end of humeral stem 708.

FIG. 7B shows another diagram for axial slice 700B. FIG. 7B coordinate system center 704, which may correspond to coordinate system center 604 described above, and shows vector 706, which may correspond to vector 606 described above. FIG. 7B also shows vector 710 determined from humeral stem 708 (e.g., vector 710 in FIG. 7B illustrates vector 710 of FIG. 7A extended beyond the distal end of humeral stem 708 and through center 604). As can be seen in FIG. 7B, vector 706 and vector 710 are not quite orthogonal. Accordingly, feature extraction unit 410 may determine a plane defined by vectors 706 and 710 and, on that plane, rotate vector 710 to be orthogonal with vector 706. This rotated vector is shown as vector 712 in FIG. 7B. Thus, in FIG. 7B, vector 706 and vector 712 are orthogonal. Feature extraction unit may additionally determine a third vector, centered at coordinate system center 704, that is orthogonal, or normal, to the plane formed by vector 706 and rotated vector 712. This orthogonal vector would be perpendicular to the 2D image of FIG. 7B (e.g., coming out of or going into the 2D image of FIG. 7B) and is shown in FIG. 7B as vector 714.

Vectors 706, 712, and 714 thus form a patient coordinate system centered at coordinate system center 704. Vector 706 approximates a medio-lateral axis for a glenoid, and vector 712 approximates an infero-superior axis for the glenoid. In anatomy, positions closer to a patient's head are generally referred to as being superior while positions closer to a patient's feet are generally referred to as being inferior. A median plane refers to an imaginary plane running through the center of a patient's body, e.g., through the nose and pelvis. Positions closer to the medial plane are generally referred to as being medial, while positions further from the medial plane are generally referred to as being lateral.

For an anatomic implant, feature extraction unit 410 determines a first vector based on a spherical implant component and a second vector based on a humeral stem component in the same manner described above for a reverse implant. In some implementations, however, the first vector may alternatively be determined based on the glenoid markers. For an anatomic implant, however, the spherical implant component is a humeral-side implant component instead of a glenoid-side implant component. As with a reverse implant, feature extraction unit 410 may also rotate the second vector determined from the humeral stem to determine an orthogonal second vector and determine a third vector that is orthogonal, or normal, to the plane formed by the first vector and the rotated second vector. Unlike a reverse implant, however, for an anatomic implant, feature extraction unit 410 determines the coordinate system center based on the location of glenoid markers in a scapula-side implant component. The first vector, rotated second vector, and third vector form a coordinate system centered at the coordinate system center.

Referring back to FIG. 2, bone pseudo segmentation unit 210 performs a pseudo segmentation of the bone of the joint. Bone pseudo segmentation unit 210 may, for example, identify voxels of the 3D model that have HU values indicative of bone. The segmentation performed by bone pseudo segmentation unit 210 may be referred to as "pseudo" segmentation because bone pseudo segmentation unit 210 is configured to only classify as bone those voxels with HU values that are within a narrow range of HU values associated with bone. Bone pseudo segmentation unit 210 classifies any voxels outside of that narrow range as not being bone, even though those voxels may in fact correspond to bone. As discussed earlier, the metal of an implant creates noise that may make the classification of some voxels uncertain based on CT scans alone. Some voxels of the 3D model that actually correspond to bone may, for example, not have HU values within the narrow range due to the presence of noise. For purposes of determining the pseudo segmented bone, bone pseudo segmentation unit 210 may be configured to classify any such uncertain voxels as being not bone and not attempt to further classify such voxels.

Figure 8:
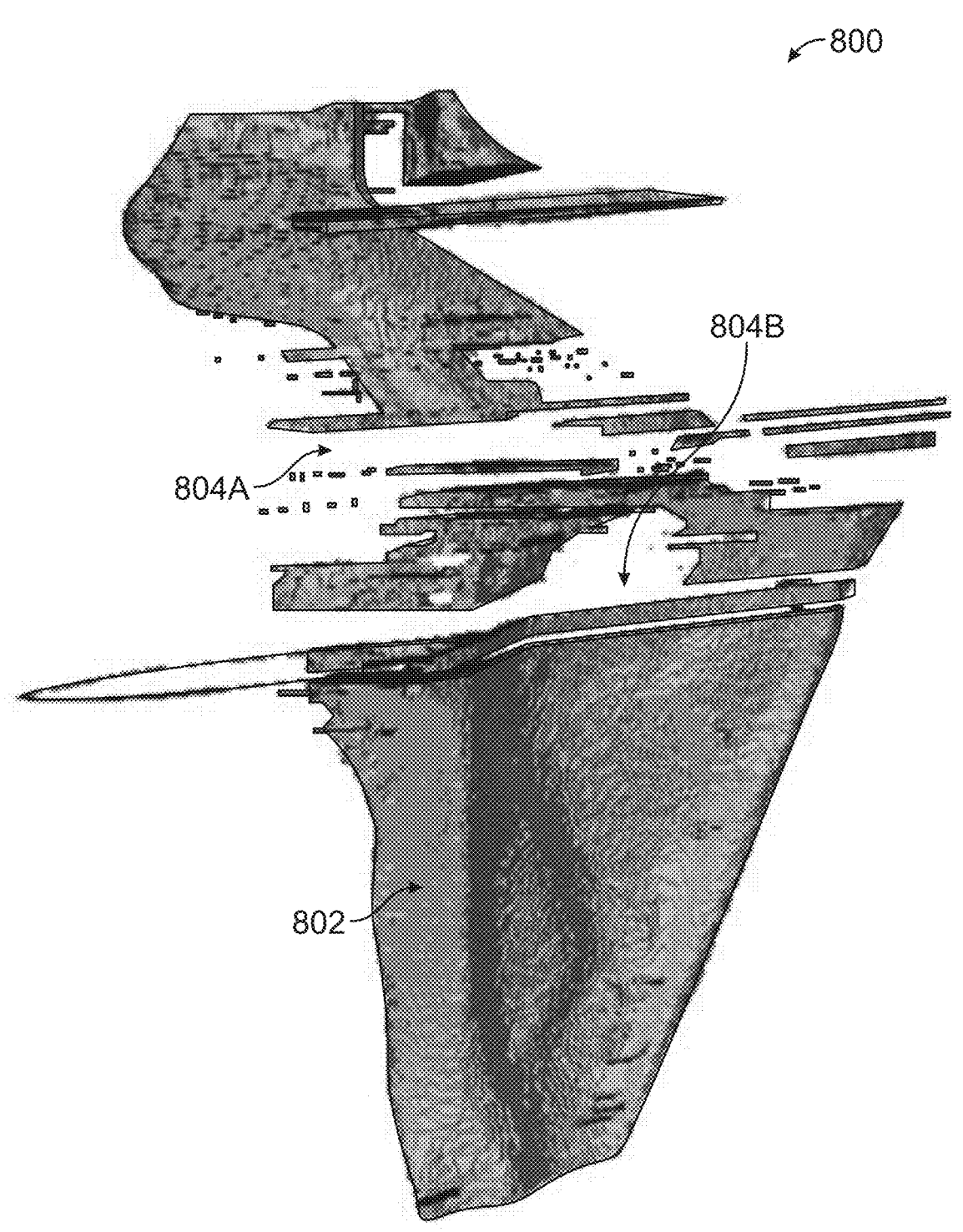
FIG. 8 shows an example of bone pseudo segmentation.

FIG. 8 shows an example of image 800 of pseudo segmented bone that may be generated by bone pseudo segmentation unit 210. In the example of FIG. 8, area 802 is an example area within image 800 that bone pseudo segmentation unit 210 determined to be bone based on the HU values of voxels for that portion of the 3D model. Areas 804A and 804B represent example areas within image 800 that bone pseudo segmentation unit 210 determined to not definitively be bone based on the HU values of voxels for that portion of the 3D model. Such areas may, for example, correspond to bone but be obscured by noise or may correspond to non-bone such as tissue or implant.

Projection unit 212 generates an estimation of a morbid, pre-implant anatomical object, such as a scapula, based on a shape model of shape models 106, the pseudo segmented bone determined by bone pseudo segmentation unit 210, and implant features determined by feature extraction unit 206. The particular shape model of shape models 106 that is used by projection unit 212 may be, for example, selected by a member of the surgical team based on a known classification of the joint prior to the implant being installed. The known classification may, for example, be a Walch classification of a glenoid, which is discussed in more detail below.

As will be explained in more detail below, projection unit 212 may use the pseudo segmented bone (e.g., image 800 of FIG. 8) as an initial shape estimate for the bone. Projection unit 212 may align the initial shape estimate to the shape model to form an initially aligned shape estimate. Projection unit 212 may, for example, align the initial shape estimate to the shape model using a determined patient coordinate system, as discussed elsewhere in this disclosure. The patient coordinate system may be determined based on the features determined by feature extraction unit 208 or based on other techniques described below for determining a patient coordinate system.

Figure 9A:
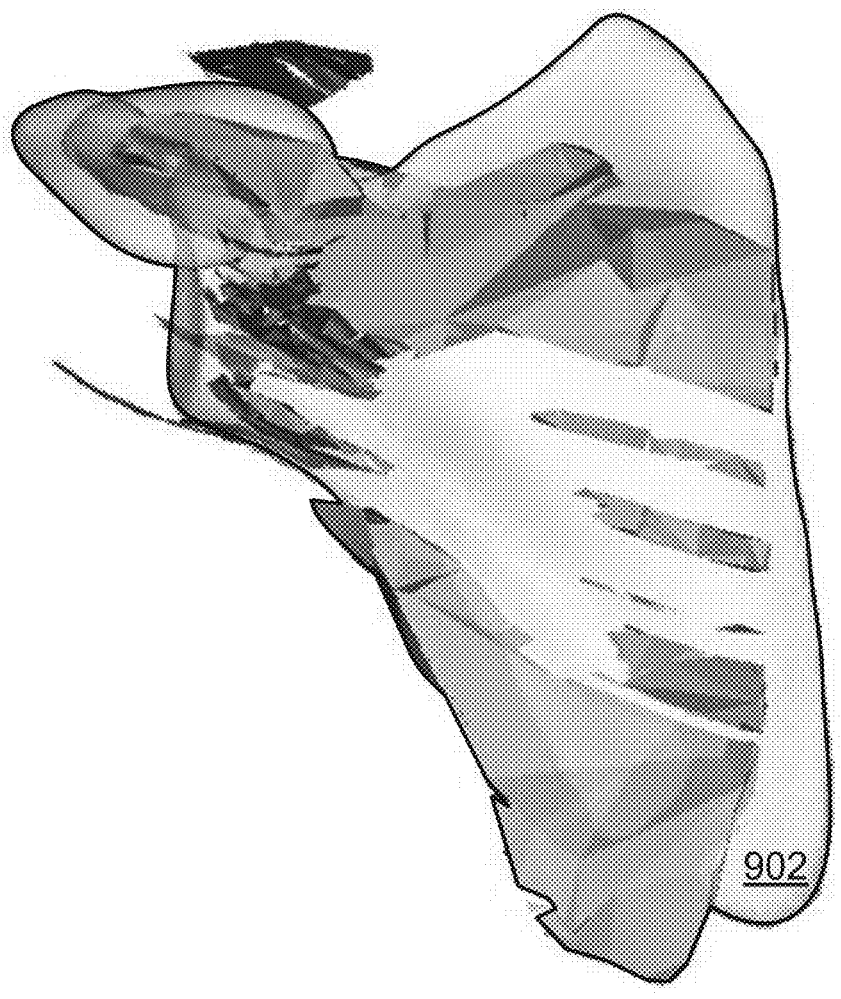
FIG. 9A shows an example of patient anatomy initially aligned to a statistical shape model (SSM) to using implant features.
Figure 9B:
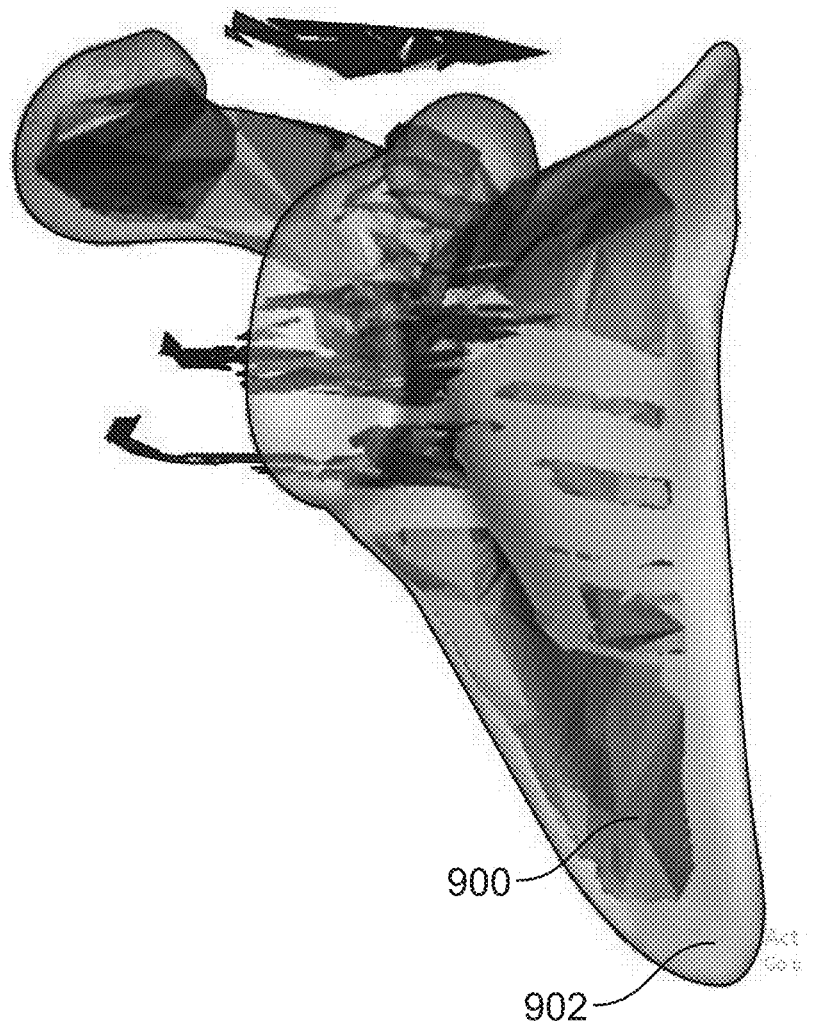
FIG. 9B shows an example of SSM registered to patient anatomy using iterative closest point (ICP) registration.

FIG. 9A shows an initial alignment of initial shape estimate 900 to shape model 902. The initial alignment is determined based on the determined patient coordinate system. FIG. 9B shows the alignment of initial shape estimate 900 to shape model 902 after rotation. Techniques for determining an initial alignment and for performing rotation are described in more detail below.

Figure 10:
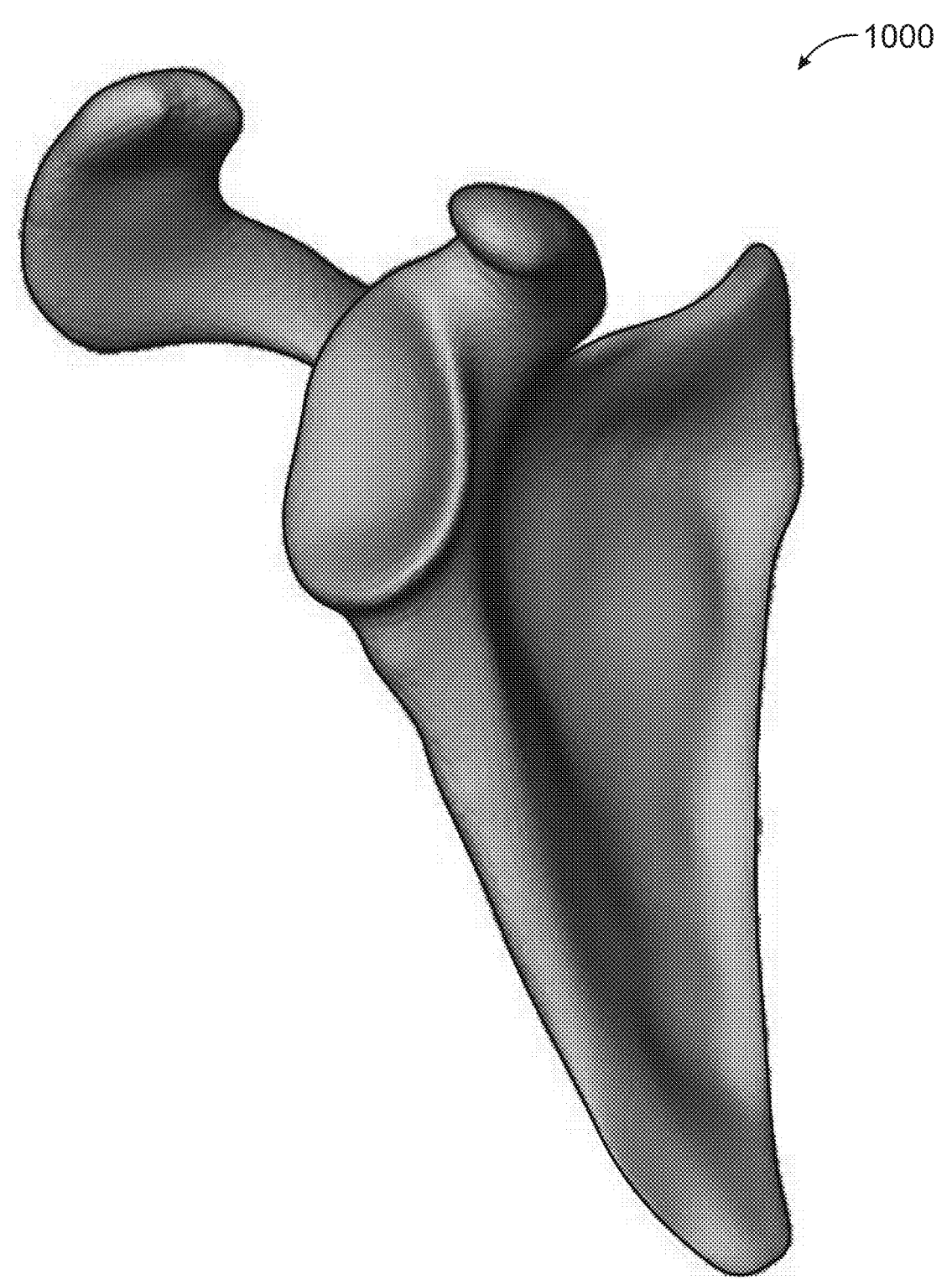
FIG. 10 shows an example of SSM to patient projection to generate a morbid, pre-implant approximation of patient anatomy.

After alignment, projection unit 212 may then deform the shape model based on the aligned shape estimate to generate a morbid, pre-implant approximation of the bone. Projection unit 212 may, for example, perform the deforming using iterative closest point (ICP) and/or elastic registration. A more detailed explanation regarding the functionality of projection unit 212 is provided below. FIG. 10 shows morbid, pre-implant approximation 1000, which represents an example output of projection unit 212.

Revision unit 200 may, for example, output the morbid, pre-implant approximation of the bone, via a display device, to a member of the surgical team for use in pre-operative planning or for other purposes. Revision unit 200 may also use the pre-implant approximation of the bone for performing segmentation on the 3D model of the patient anatomy.

Projection unit 212 may also output the morbid, pre-implant approximation of the bone to TML system 214. Based on the implant mask from implant segmentation unit 204, the morbid, pre-implant approximation from projection unit 212, and the determined implant features from feature extraction unit 208 (e.g., information indicating the coordinate system), TML system 214 segments the 3D model (e.g., anatomy scan 106 to isolate specific portions of patient anatomy, such as the scapula, the clavicle, the glenoid, the humerus, and the like. TML system 214 may be configured to perform the segmentation based on machine learning, as described in more detail below. TML system 214 generates a probability classification map, which may associate each voxel or groups of voxels with a probability of corresponding to a specific piece of anatomy.

As indicated above, bone pseudo segmentation unit 210 can segment the implant from non implant within the 3D model with relatively little ambiguity. Identifying the boundary between the scapula and an adjacent bone, as one example, requires more complex decision making. Accordingly, TML system 214 may be configured to remove the implant from the 3D model. In this context, remove may mean to set voxels corresponding to implant to a constant distinct color, such as black. TML system 214 may then compare the morbid, pre-implant approximation to the remaining non-implant voxels, and based on the comparison, determine a probability that a particular voxel or group of voxels corresponds to scapula, corresponds to humerus, etc.

Figure 11:
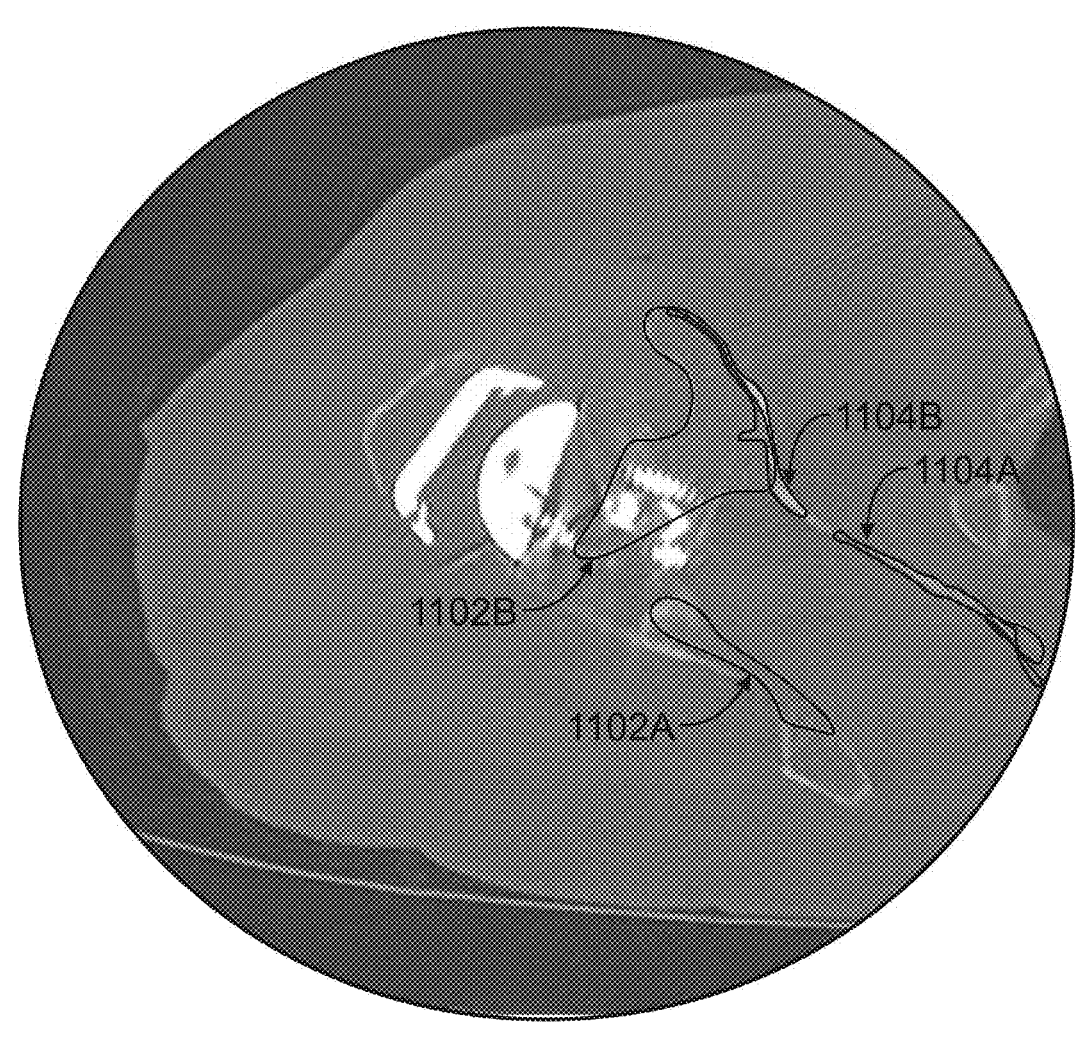
FIG. 11 shows an example of a CT-scan with an overlaid scapula pseudo segmentation and scapula SSM prediction.

Post processing unit 216 may, for example, process the segmented image and the probability classification map to determine and output a final segmented image. In one example, the final segmented image may include annotations showing the boundaries that correspond to the pseudo segmentation determined by pseudo segmentation unit 210, the boundaries that correspond to the morbid, pre-implant approximation, or other such boundaries. In FIG. 11, for instance, boundaries 1102A and 1102B may be presented in a first style, e.g., color or line type, to indicate that those boundaries correspond the pseudo segmented image, while boundaries 1104A and 1104B may be presented in a different style to indicate those boundaries correspond to the morbid, pre-implant approximation.

Figure 12:
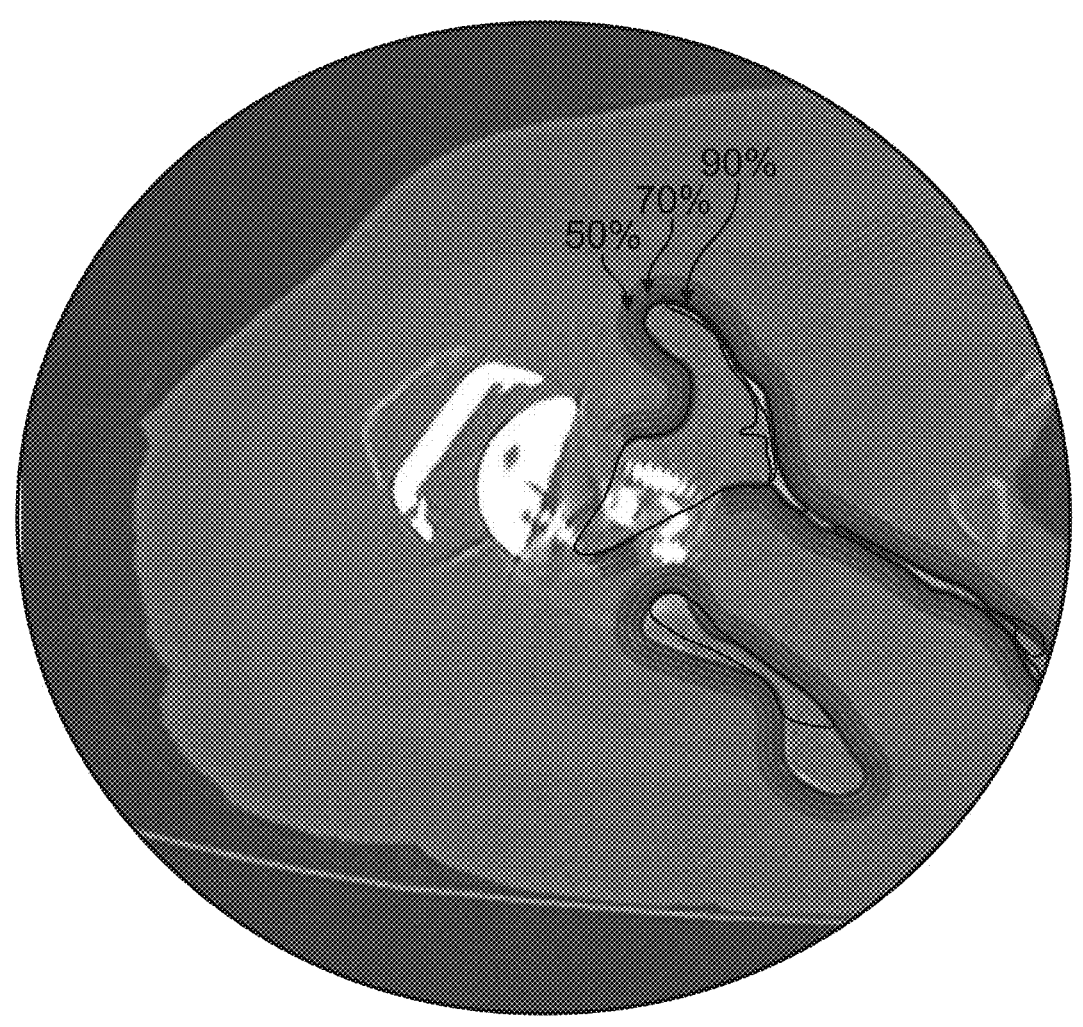
FIG. 12 shows an example CT-scan with an overlaid scapula pseudo segmentation, scapula SSM prediction, and ML probability map.

The probability classification map represents a per voxel or per group of voxels confidence level. The probability map may be used by post processing unit 216 to generate probabilities for multiple segmentations. FIG. 12 shows an example of an output image with three proposed segmentations, each segmentation having an associated probability. The 90% probability may, for example, mean that the area within that line has been determined to have a 90% probability of belonging to the scapula. The lines further away have lower probabilities, meaning it is more likely that those segmentations include bone not belonging to the scapula.

Post processing unit 216 may be configured to receive user input. The user input may, for example, be a selection of one of the proposed segmentations or may be a manual segmentation that is guided by the probability classification map.

Figure 13:
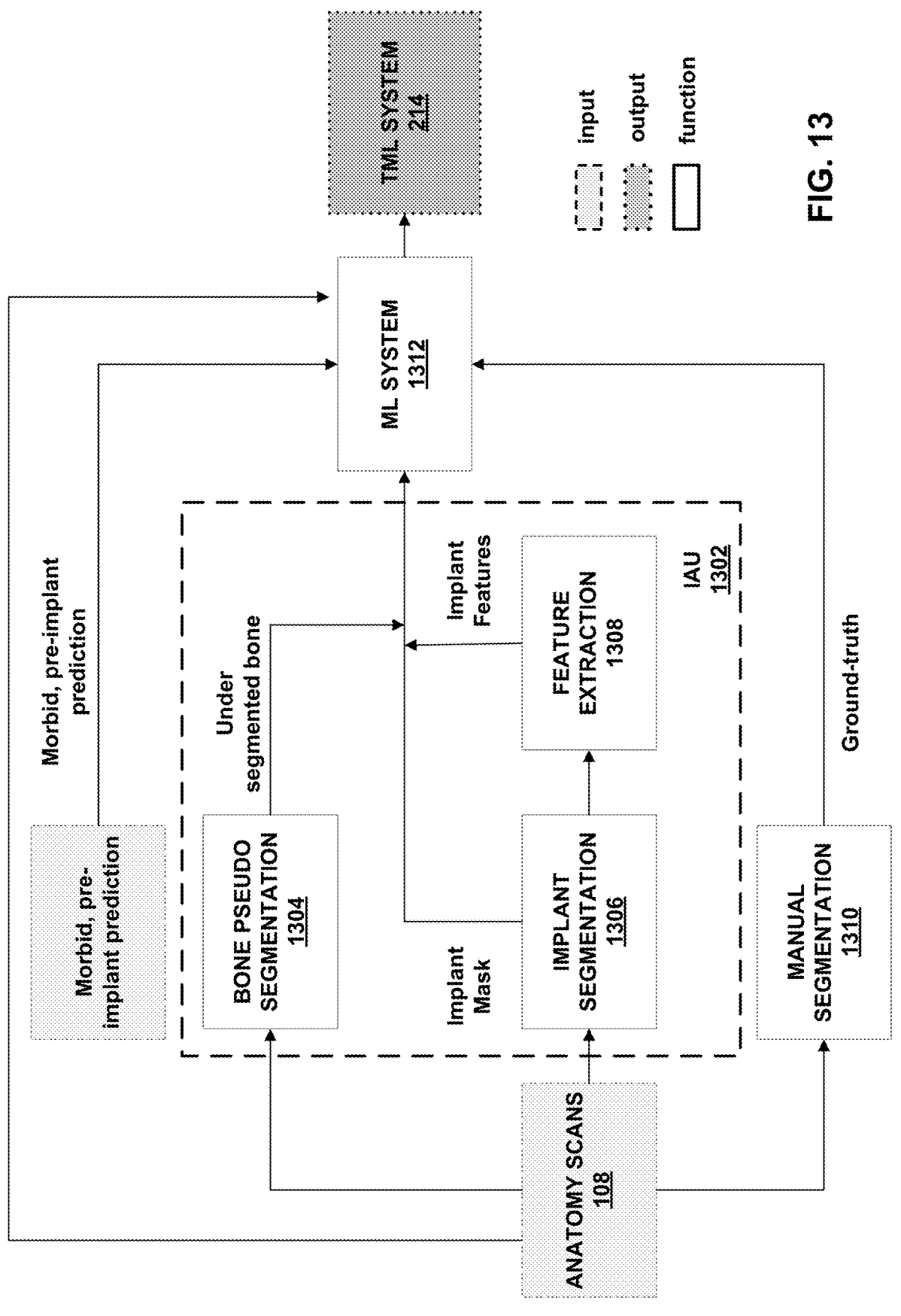
FIG. 13 shows an example of a machine learning unit.

FIG. 13 shows an example training system for TML system 214. The training system of FIG. 13 includes IAU 1302, which includes bone pseudo segmentation unit 1304, implant segmentation unit 1306, and feature extraction unit 1308. The training system of FIG. 13 also includes manual segmentation unit 1310 and ML system 1312. IAU 1302, bone pseudo segmentation unit 1304, implant segmentation unit 1306, and feature extraction unit 1308 generally functions in the same manner as IAU 202, bone pseudo segmentation unit 204, implant segmentation unit 206, and feature extraction unit 208 described above to generate an implant mask and determine implant features.

For a particular anatomy scan from anatomy scans 108, IAU 1302 generates an implant mask and a pseudo segmentation and determines implant features. For the same particular anatomy scan, manual segmentation unit 1310 produces one or more manual segmentations of the anatomy scan. The manual segmentations may, for example, be generated based on input from surgeons or other experts. The manual segmentations may serve as a ground truth for which ML system 1312. ML system 1312 determines how to segment the anatomy scan, based on the pseudo segmented image, the implant mask, and the determined features, in a manner results in the same segmentation as the manual segmentations, e.g., a mean or a mode of the manual segmentations. ML system 1312 may use machine learning to learn these segmentations using a large number of training samples. The machine learning techniques may then be implemented by TML system 214.

Aspects of shape modeling will now be described in more detail. Processing circuitry 102 and projection unit 212 may, for example, be configured to determine pre-morbid approximations or morbid, pre-implant approximations of a patient anatomy. SSMs are a compact tool to represent shape variations among a population of samples (database). For example, a clinician or researcher may generate a database of image scans, such as CT image data, of different people representative of the population as a whole who do not suffer from damaged or diseased glenoid, humerus, or neighboring bones. Additionally or alternatively, a clinician or researcher may generate a database of image scans of different people representative of the population as a whole who do suffer from specific types of damaged or diseased glenoid, humerus, or neighboring bones.

As one example, morphologic features of the glenoid are traditionally classified using a system referred to as Walch classification. The Walch classification for a diseased glenoid is determined based on axial cuts of two-dimensional CT scans, and morphologic features of the glenoid are divided into three main groups with subtypes. Type A is centered or symmetric arthritis without posterior subluxation of the humeral head. Type A1 has minor central wear or erosion, and Type A2 has severe or major central wear or erosion. Type B is characterized by asymmetric arthritis with posterior subluxation of the humeral head. Type B1 has no obvious glenoid erosion with posterior joint space narrowing, subchondral sclerosis, and osteophytes. Type B2 has apparent or obvious erosion of the posterior glenoid forming a biconcave appearance of the glenoid. Type C shows glenoid retroversion greater than 25° (dysplastic in origin) regardless of glenoid erosion or the location of the humeral head with regard to the glenoid.

The clinician or researcher may determine mean shapes for patient anatomy from the shapes in the database. The clinician or researcher may determine mean shapes for the patient anatomy for the people who do not suffer from damaged joints as well as determine mean shapes for each of the various type of diseased joints. The clinician or researcher may, for example, determine a mean shape for a type A glenoid, a type A1 glenoid, a type B glenoid, etc. The various techniques below will be described with respect to shape model 106, which may represent either a pre-morbid model or a morbid model. As will be described in more detail below, the mean shapes for the various types of diseased joints may be used to determine a morbid, pre-implant characterization of an anatomical object for a patient with an implant.

Referring back to FIG. 1, memory 104 stores information indicative of shape model 106. As one example, shape model 106 represent a mean shape for the anatomical object (e.g., glenoid, humeral head, etc.) of patient anatomy from the shapes in the database. Other examples of shape model 106 are possible, such as a mode or median of the shapes in the database. A weighted average is another possible example of shape model 106. Shape model 106 may be a surface or volume of points (e.g., a graphical surface or a volume of points that define a 3D model), and the information indicative of mean shape may be coordinate values for vertices of primitives that interconnect to form the surface. Techniques to generate an SSM like shape model 106 and values associated with generating shape model 106 can be found in various literature such as from: http://www.cm-lab.csie.ntu.edu.tw/~cyy/learning/papers/PCA_ASM.pdf dated Aug. 22, 2006. Other ways in which to generate shape model 106 are possible.

With shape model 106, processing circuitry 102 may represent anatomy shape variations by adding points or values of shape model 106 to a covariance matrix. For example, the SSM can be interpreted as a linear equation:

$$s_i = s' + \sum_i b_i \sqrt{\lambda_i} \times v_i.$$

In the above equation, s' is shape model 106 (e.g., point cloud of mean shape as one example, where point cloud defines coordinates of points within shape model 106, such as vertices of primitives that form shape model 106). In the equation, $\lambda_i$ is the eigenvalues and $v_i$ is the eigenvectors of the covariance matrix respectively (also called modes of variations). The covariance matrix represents the variance in a dataset. The element in the i, j position is the co-variance between the i-th and j-th elements of a dataset array.

SSM stands for constructing the covariance matrix of the database then performing "singular value decomposition"

which extracts a matrix of principal vectors (also called eigenvectors) and another diagonal matrix of positive values (called eigenvalues). Eigenvectors ($v_i$ in the equation) are new coordinate system bases of the database. Eigenvalues ($\lambda_i$ in the equation) represent the variance around the eigenvectors ($v_i$). Together eigenvectors and eigenvalues may reflect the amount of variation around the corresponding axis.

This mathematical equation allows processing circuitry 102 to create an infinite number of instances of $s_j$ (e.g., different variations of the shape model) by simply changing the weights $b_i$ of the covariance matrix. For instance, to generate a new shape model, processing circuitry may determine a value of $b_i$, and determine a new value of $s_i$. In the above example, $\lambda_i$ and $v_i$ and s' are all known based on the manner in which s' was generated (e.g., based on the manner in which shape model 106 was generated). By selecting different values of $b_i$, processing circuitry 102 may determine different instances of a shape model (e.g., different $s_i$ which are different variations of the shape model 106).

The shape model(s) may represent what an anatomical object should look like for a patient. As described in more detail, processing circuitry 102 may compare points (e.g., in the 3D cloud of points) of the shape model of the anatomical object with anatomical points represented in the image data of scans 108, as anatomical points of the anatomical object that are not impacted or minimally impacted by the injury or disease (e.g., non-pathological points). Based on the comparison, processing circuitry 102 may determine a pre-morbid or morbid, pre-implant characterization of the anatomical object.

As an example, assume that the surgeon would like to determine the pre-morbid characteristics of the glenoid cavity for a shoulder surgery or determine the morbid, pre-implant characteristics of the glenoid for a revision surgery. There is a correlation between the shape of the glenoid cavity and the bony zone around it, such as the medical glenoid vault, the acromion, and the coracoid. Shape model 106 may be the mean shape of the scapula that includes the glenoid cavity. Assume that in the patient the glenoid cavity is pathological (e.g., diseased or damaged).

In accordance with example techniques described in this disclosure, processing circuitry 102 may determine the instance of "s" (e.g., shape model of scapula with glenoid cavity) that best matches the non-pathological anatomy of the anatomical object of the patient (e.g., non-pathological portions of the scapula in scans 108). The glenoid cavity, in the instance of "s," that best matches the non-pathological anatomy (referred to as s* and represented by a point cloud similar to the shape model) may be indicative of the pre-morbid or morbid, pre-implant characterization of the pathological glenoid cavity.

Processing circuitry 102 or projection unit 212 may determine the instance of s* (e.g., shape model of scapula with glenoid cavity that best matches the non-pathological portions of the patient's scapula). The non-pathological portions may be portions of the anatomical object with minimal to no impact from the disease or injury, where the anatomical object and its surrounding anatomy are taken from the segmentation performed by scans 108 to segment out the anatomical object.

In some examples, to determine a pre-morbid or morbid, pre-implant characterization of a particular anatomical object, anatomy beyond the anatomical object may be needed to align the shape model. For instance, to determine a pre-morbid or morbid, pre-implant characterization of the glenoid, anatomy of the scapula may be needed to align the shape model. Then, the glenoid of the shape model represents the pre-morbid or morbid, pre-implant characterization of the patient's glenoid. Hence, the shape model may not be limited to modeling just the anatomical object of interest (e.g., glenoid) but may include additional anatomical objects.

Processing circuitry 102 or projection unit 212 may perform the following example operations: (1) initially align the segmented anatomical object from image data of scans 108 to a coordinate system of shape model 106 to generate an initial aligned shape; (2) compensate for errors in the initial alignment due to under and over segmentation, where under- and over-segmentation are due to imperfections in generating scans 108, to generate an aligned shape (also called intermediate aligned shape); and (3) perform iterative operations that includes iterative closest point (ICP) operations and elastic registration to determine the instance of s* (i.e., the instance of s' that most closely matches the patient anatomy as identified by the segmentation object). With respect to operation (1), this disclosure will describe different techniques for determining a patient coordinate system, depending on whether a patient has an anatomical or reverse implant or if the patient does not yet have an implant installed or has a hemi implant installed. Example techniques to perform operations (1)-(3) are described in more detail below.

There may be a few technical problems with generating the pre-morbid or morbid, pre-implant characterization of the patient anatomy. One issue may be that due to under- or over-segmentation the image data needed from scans 108 is not available or distorted creating a challenge to align the segmented object to shape model 106. Another issue may be that once there is alignment to shape model 106, registration of shape model 106 to the segmented object may be poor, resulting in poor pre-morbid or morbid, pre-implant characterization.

This disclosure describes example techniques that allow alignment of the segmented object to shape model 106 even in situations where there is under- or over-segmentation and in situations where a patient already has an implant. This disclosure also describes example techniques to register shape model 106 to the segmented object (e.g., in multiple level iterative processes that uses ICP and elastic registration). The example techniques described in this disclosure may be use separately or together. For instance, in one example, processing circuitry 102 may be configured to perform alignment of the segmented object to shape model 106 utilizing example techniques described in disclosure but perform registration of shape model 106 to the segmented object using some other techniques. In one example, processing circuitry 102 may utilize some other technique to perform alignment of the segmented object to shape model 106 but perform registration of shape model 106 to the segmented object using one or more example techniques described in this disclosure. In some examples, processing circuitry 102 may perform the example alignment and registration techniques described in this disclosure.

As described above, processing circuitry 102 may align the segmented object (e.g., as segmented using example techniques such as voxel intensity comparisons) to shape model 106. In this disclosure, the alignment refers to changes to the coordinate system of the segmented object so that the segmented object is in same coordinate system as shape model 106. As also described above, one example of shape model 106 is a shape model of the anatomy of the scapula with glenoid cavity, where the glenoid cavity is the injured or diseased anatomical object. For instance, shape model 106 is defined in its own coordinate system and may be different than the patient coordinate system (e.g., coordinate system to define the point cloud of 3D points in scans 108). The patient coordinate system is the coordinate system used to define points within the anatomy of the patient in scans 108 that includes non-pathological points and pathological points. The non-pathological points refer to the points in scans 108 for non-pathological anatomy, and the pathological points refer to points in scans 108 for pathological anatomy.

There may be various ways in which to determine pathological and non-pathological points. As one example, the surgeon may review the image data of scans 108 to identify pathological and non-pathological points. As another example, the surgeon may review a graphical representation of the segmented object to identify pathological and non-pathological points. As another example, there may be an assumption that certain anatomical points are rarely injured or diseased and are present in image data of scans 108. For instance, the medical glenoid vault, the acromion, and the coracoid, are a few examples. Additional examples include trigonum scapulae and angulus inferior. However, one or more both trigonum scapulae and angulus inferior may not be present or distorted in the image data of scans 108 due to the over- and under-segmentation.

In one or more examples, processing circuitry 102 may determine a patient coordinate system, which is the coordinate system recorded for the CT scan data of scans 108. Shape model 106 may be defined in its own coordinate system. Processing circuitry 102 may determine the coordinate system of shape model 106 based on the metadata stored with shape model 106, where the metadata was generated as part of determining the mean of the shapes in the database. Processing circuitry 102 may determine a transformation matrix based on the patient coordinate system and the coordinate system of shape model 106. The transformation matrix is a way by which processing circuitry 102 transforms the segmented object (e.g., points in the 3D volume of points) into the coordinate system of shape model 106. For example, points in the 3D volume of points of the segmented object may be defined with (x, y, z) coordinate values. The result of the transformation may be coordinates (x', y', z') coordinate values that are aligned to the coordinate system of shape model 106. Processing circuitry 102 calculates the transformation matrix through a close-form equation.

There are multiple ways to determine the transformation matrix. As one example, the coordinate system may be c=(x,y,z,o), where x, y and z are the orthogonal basis 3D vectors and o is the origin (c is a 4×4 homogeneous matrix with the last raw is (0,0,0,1)). The new coordinate system to which the segmented object is to be transformed is C=(X, Y,Z,O). In this example, the transformation matrix is then: T=c^−1×C. Accordingly, processing circuitry 102 may determine the patient coordinate system.

FIGS. 14 to 20 describe example ways in which processing circuitry 102 determines the patient coordinate system. As described in more detail, even after determining the patient coordinate system, further adjustment to shape model 106 may be needed to properly align the segmented object (e.g., patient anatomy) to shape model 106. For instance, because of over- or under-segmentation, missing or distorted image data cannot be used to determine the patient coordinate system. Therefore, processing circuitry 102 utilizes image data that is available to perform an initial alignment, but then may perform further operations to fully align the segmented object to shape model 106.

Figure 14:
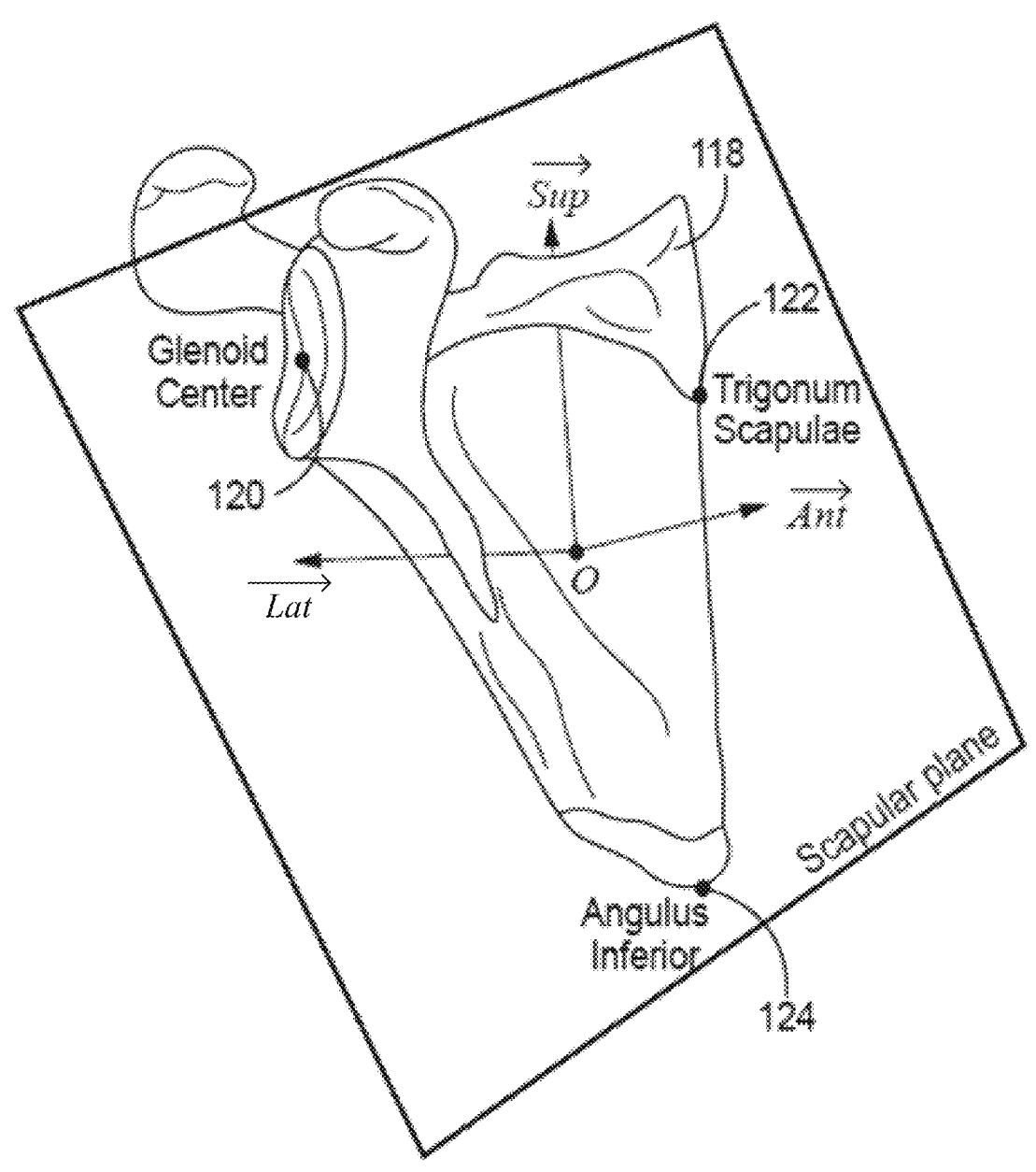
FIG. 14 is an illustration of a scapula having points of interest used to determine a coordinate system of a patient.

FIG. 14 is an illustration of a scapula having points of interest used to determine coordinate system of a patient. For instance, FIG. 14 illustrates scapula 118 having glenoid center 120, trigonum scapulae 122, and angulus inferior 124. Some techniques utilize glenoid center 120, trigonum scapulae 122, and angulus inferior 124 to determine the patient coordinate system. For instance, glenoid center 120, trigonum scapulae 122, and angulus inferior 126 may be considered as forming a triangle, and processing circuitry 102 may determine a center point (e.g., in 3D) of the triangle as the origin of the patient coordinate system.

However, such techniques may not be available in cases of over- and under-segmentation. As one example, in under-segmentation, scans 108 may be inferiorly and/or superiorly and/or medially truncated and trigonum scapulae 122 and angulus inferior 124 may not be present in the segmented objects extracted from the image data of scans 108. Therefore, processing circuitry 102 may not be able to utilize all three of glenoid center 120, trigonum scapulae 122, and angulus inferior 124 for purposes of determining patient coordinate system.

In one or more examples, where specific landmarks (e.g., glenoid center 120, trigonum scapulae 122, and angulus inferior 124) are not available as segmented anatomical objects in the image data of scans 108, processing circuitry 102 may define the patient coordinate system based on the scapula normal (e.g., a vector normal to scapula 118) and a transverse axis based on the 3D information of image data of scans 108. As described in more detail, processing circuitry 102 may determine the scapula normal based on the normal of the best fit plane to the body of scapula 118. Processing circuitry 102 may determine the transverse axis by fitting a line through the spongious region that lies between the supraspinatus fossa, the spine, and the scapula body. Using the spongious region, processing circuitry 102 may define a Cartesian (e.g., x, y, z) coordinate system (although other coordinate systems are possible). The origin of the coordinate system may be glenoid center 120; although other origins are possible.

In this manner, processing circuitry 102 may determine a coordinate system for the patient based on anatomical objects that are present in the image data of scans 108, even where there is over- or under-segmentation. Based on the coordinate system, processing circuitry 102 may align the segmentation objects to the coordinate system of shape model 106 (e.g., initial SSM) and iteratively deform shape model 106 to register a shape model (e.g., a deformed version of shape model 106) to the patient segmentation object to determine a pre-morbid or morbid, pre-implant characterization.

Figure 15A:
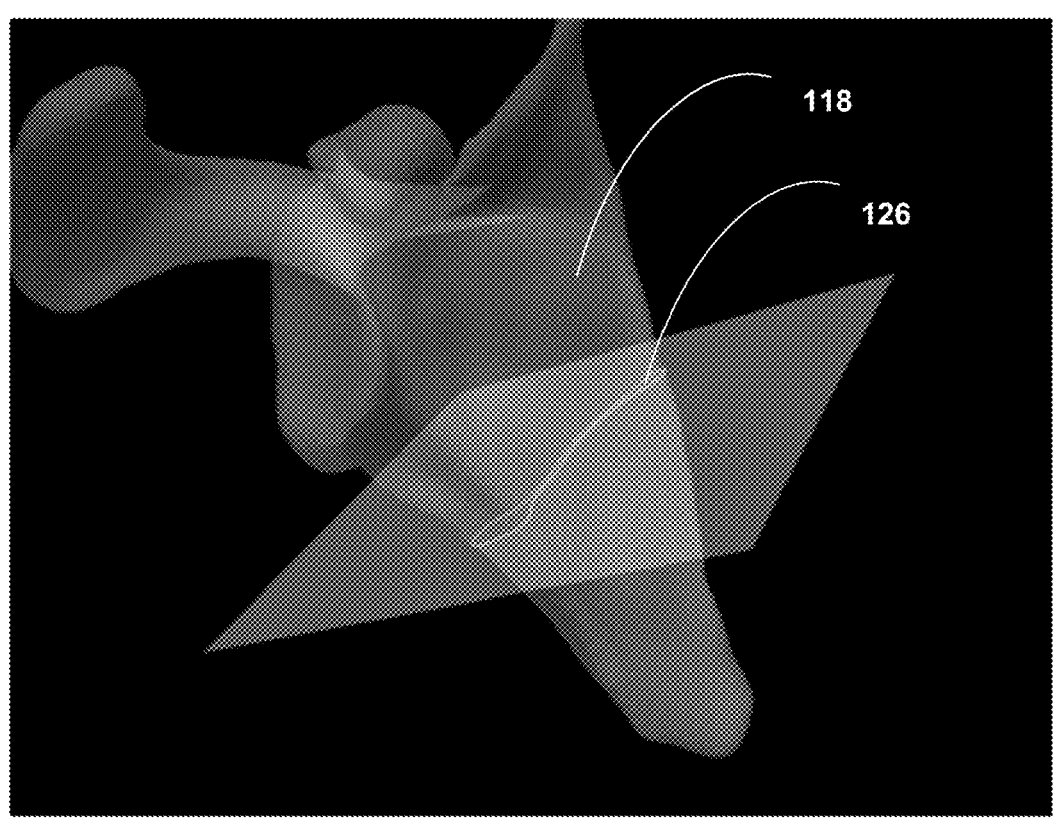
FIGS. 15A and 15B are illustrations of a planar cut through a scapula for determining a coordinate system of a patient.
Figure 15B:
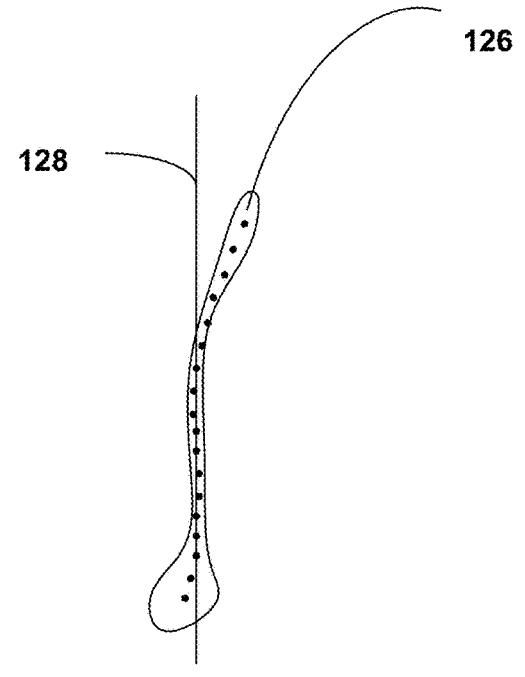

FIGS. 15A and 15B are illustrations of a planar cut through a scapula for determining a patient coordinate system that may not rely upon anatomical objects whose image data is unavailable due to over- or under-segmentation. For instance, unlike example of FIG. 14 that relied upon glenoid center 120, trigonum scapulae 122, and angulus inferior 124, which may not be available due to under- or over-segmentation, the example techniques illustrated with respect to FIGS. 15A and 15B may not rely on anatomical objects that are unavailable due to under- or over-segmentation.

As illustrated in FIG. 15A, one of scans 108 may be a scan of an axial cut through scapula 118, which shows scapula portion 126. FIG. 15B is a top view of scapula portion 126 of FIG. 15A through scapula 118.

FIG. 15B illustrates a plurality of dots, representing an intersecting plane through portion 136, that go through scapula portion 126. In one or more examples, processing circuitry 102 may determine a plane that intersects through scapula portion 126. The intersection of the plane through portion 126 is shown with the dots. For example, FIG. 15B illustrates line 128. Line 128 intersects a majority of the dots in scapula portion 126.

The dots in scapula portion 126 may be the "skeleton" of the surrounding contour. The skeleton is dots through the contour that are each the same distance to their respective nearest boundary. Although the skeleton is described, in some examples, the dots in scapula portion 126 may be center points, as another example.

Processing circuitry 102 may determine the image data that forms portion 126. Processing circuitry 102 may determine dots of portion 126 (e.g., skeleton dots or center dots as two non-limiting examples), as illustrated. Processing circuitry 102 may determine a plane that extends up from line 128 toward the glenoid and extends downward from line 128 toward the angulus inferior.

For example, although FIG. 15A illustrates one example axial cut, processing circuitry 102 may determine a plurality of axial cuts, and determine the points through the axial cuts, similar to FIG. 15B. The result may be a 2D points for each axial cut, and processing circuitry 102 may determine a line, similar to like 128, through each of the axial cuts. Processing circuitry 102 may determine a plane that extends through the lines for each axial cut through scapula 118. This plane is through scapula 118 and is illustrated in FIG. 16.

Figure 16:
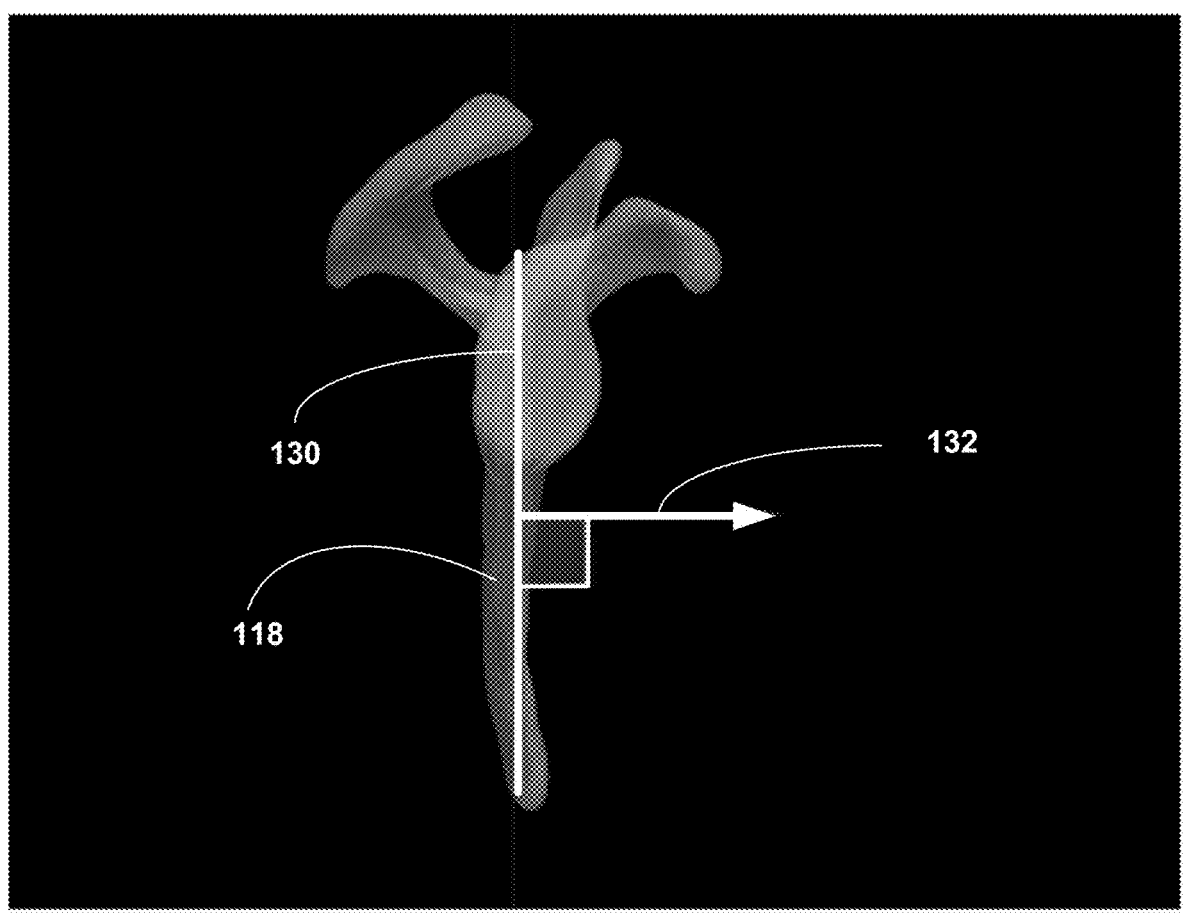
FIG. 16 is a conceptual diagram of a perspective view of a normal line to a plane through a scapula for determining a coordinate system of a patient.

FIG. 16 is a conceptual diagram of a perspective view of a normal line to a plane, as determined with the example illustrated in FIGS. 15A and 15B, through a scapula for determining a coordinate system of a patient. For instance, FIG. 16 illustrates plane 130. Plane 130 intersects line 128 illustrated in FIG. 15B. Plane 130 may be considered as the best fit plane to the body of scapula 118. Processing circuitry 102 may determine vector 132 that is normal to plane 130. In one or more examples, vector 132 may form one axis (e.g., x-axis) of the patient coordinate system. Techniques to determine the other axes is described in more detail below.

Figure 17:
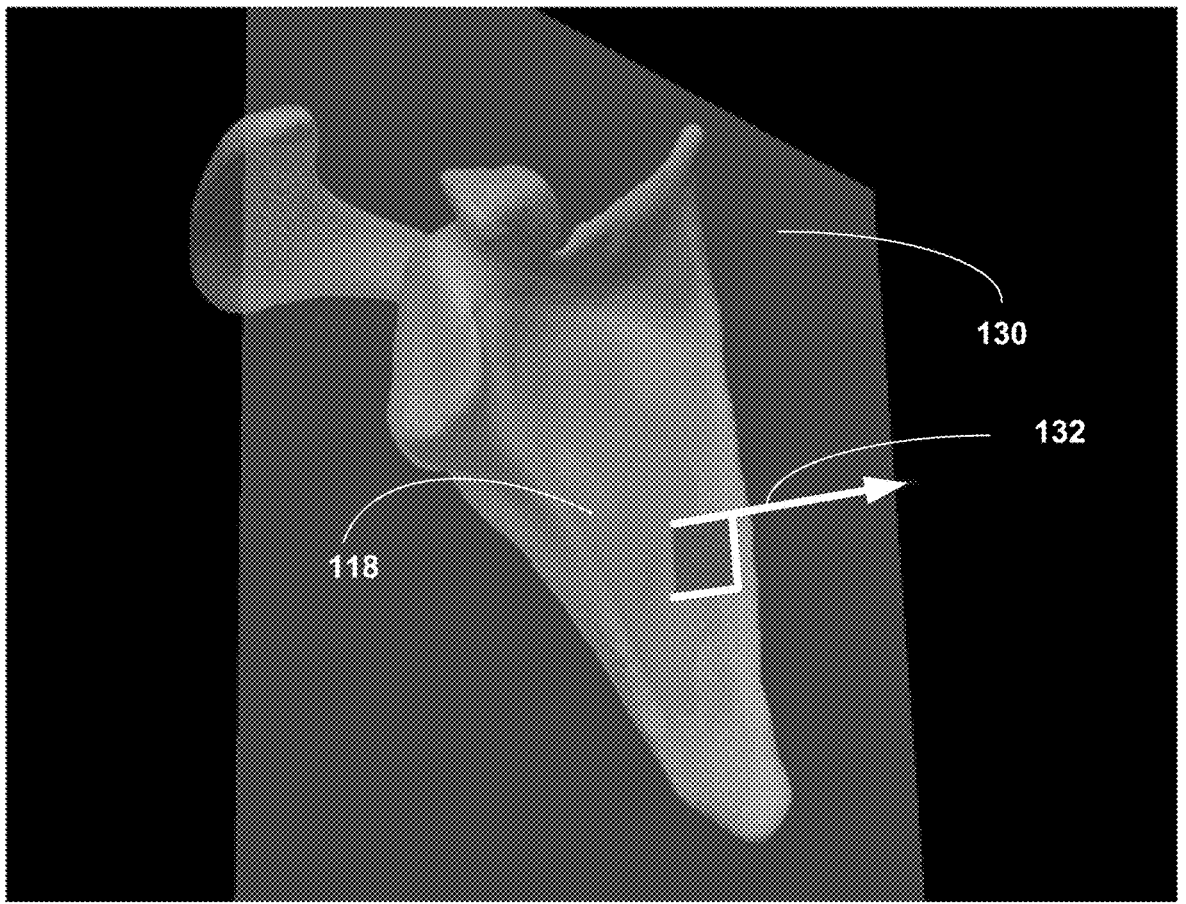
FIG. 17 is a conceptual diagram of another perspective view of a normal line to a plane through a scapula for determining a coordinate system of a patient.

FIG. 17 is a conceptual diagram of another perspective view of the example of FIG. 16 such as another perspective view of a normal line to a plane through a scapula for determining a coordinate system of a patient. FIG. 17 is similar to FIG. 16 but from a front perspective rather than the side perspective of FIG. 16. For example, FIG. 17 illustrates scapula 118 of the patient with the best fit plane 130 and the normal vector 132.

In this manner, processing circuitry 102 may determine a first axis of the patient coordinate system that is normal to scapula 118. Processing circuitry 102 may determine a second axis of the patient coordinate system as an axis that is transverse through scapula 118.

Figure 18:
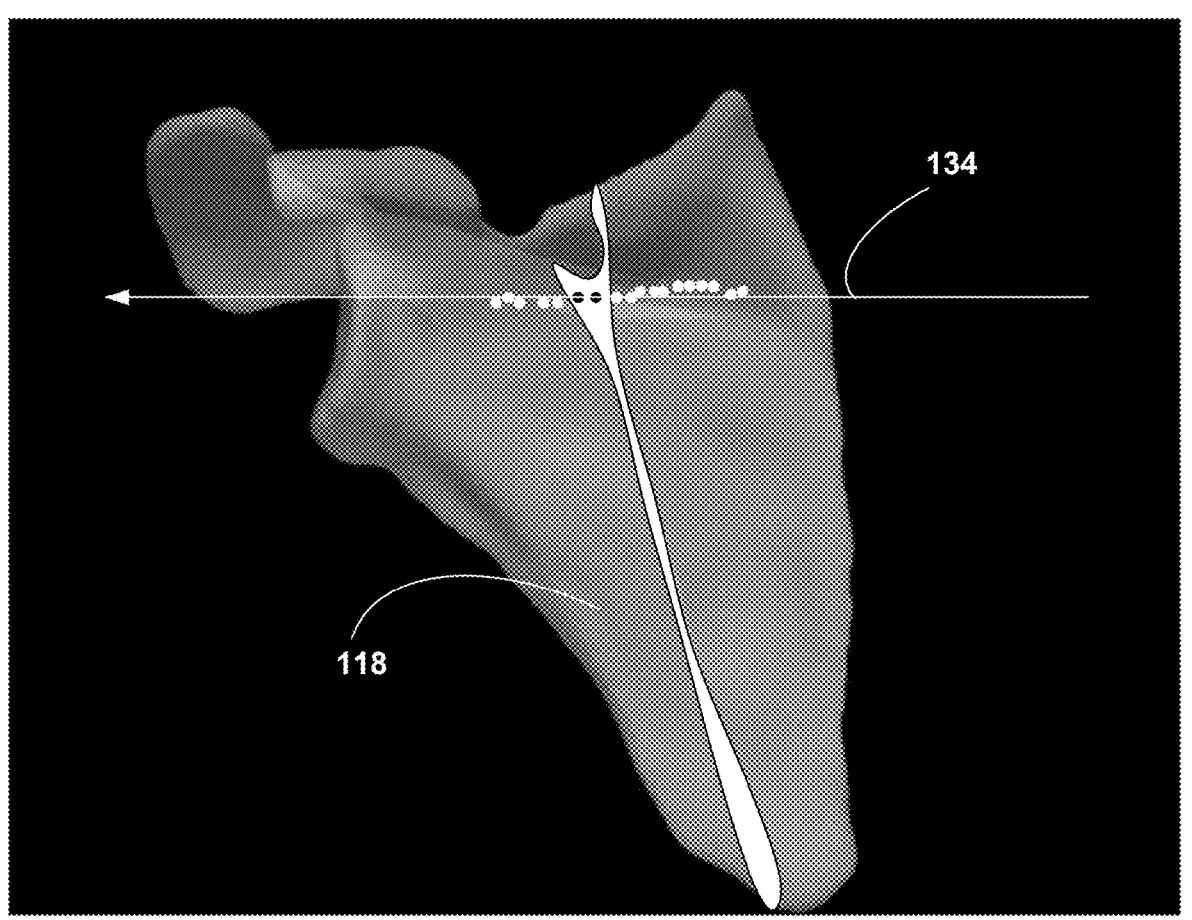
FIG. 18 is a conceptual diagram illustrating a transverse axis through a scapula for determining a coordinate system of a patient.

FIG. 18 is a conceptual diagram illustrating a transverse axis through a scapula for determining a coordinate system of a patient. For instance, FIG. 18 illustrates example to determine an axis, in addition to the one determined in FIGS. 4 and 5, for aligning shape model 106 to coordinate system of the image data of scans 108.

Figures 19A, 19B:
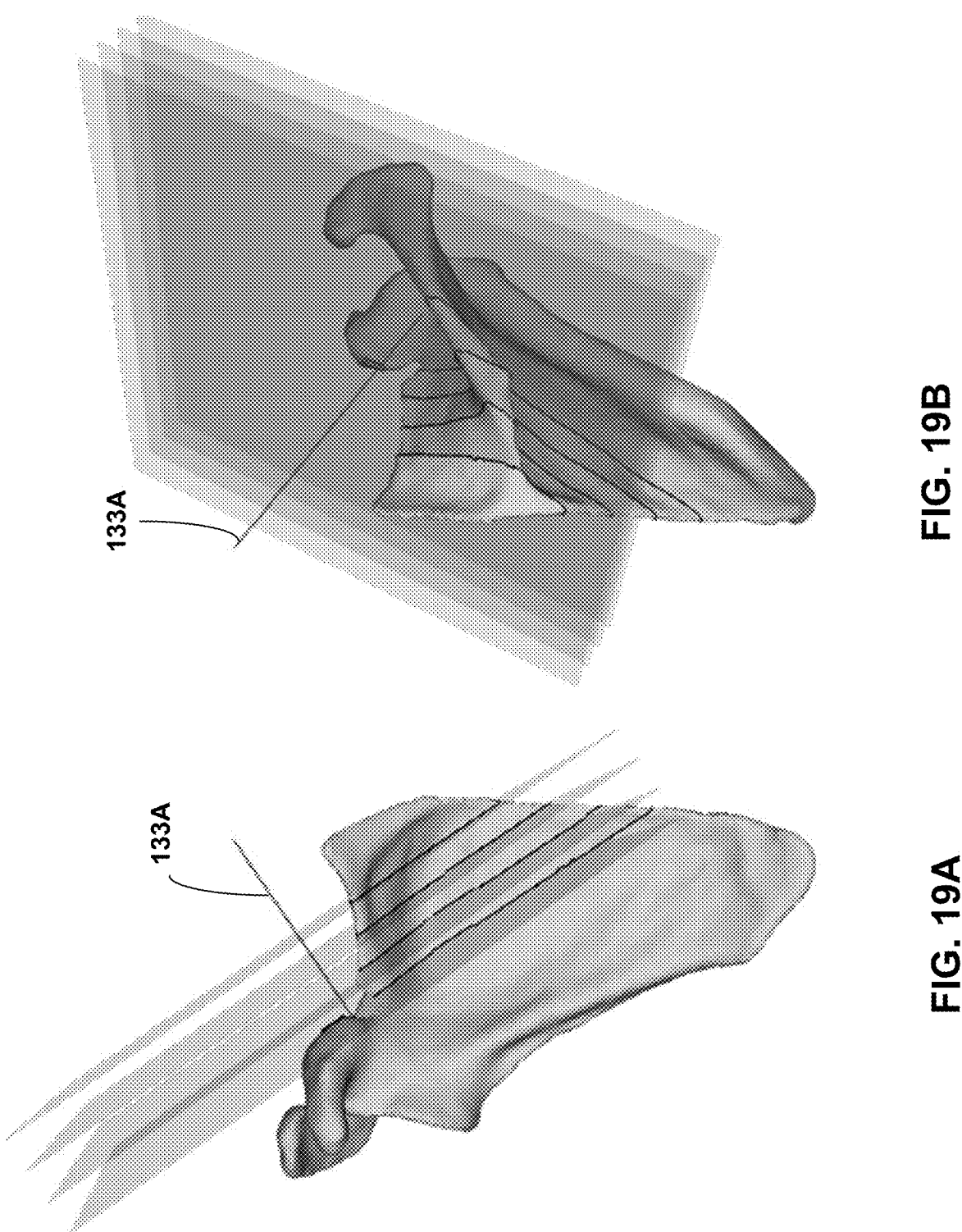
FIGS. 19A and 19B are conceptual diagrams illustrating an example of sagittal cuts through a scapula for determining the transverse axis of FIG. 18.

FIG. 18 illustrates transverse axis 134. Processing circuitry 102 may determine transverse axis 134 as a line that fits through the spongious region that lies between the supraspinatus fossa, the spine, and the scapula body. The example techniques to determine transverse axis 134 is described with respect to FIGS. 19A, 19B, FIGS. 20A-20C, and FIGS. 21A and 21B, and. Processing circuitry 102 may determine plurality of sagittal cuts through the scapula based on the image data of scan 108 as illustrated in FIGS. 19A and 19B. For instance, FIGS. 19A and 19B are different perspectives of sagittal cuts through scapula based on axis 133A. Processing circuitry 102 may utilize axis 133A based on an approximation of the spongious region that lies between supraspinatus fossa, the spine, and the scapula body, and may be pre-programmed with the estimated axis.

Figures 20A, 20B, 20C:
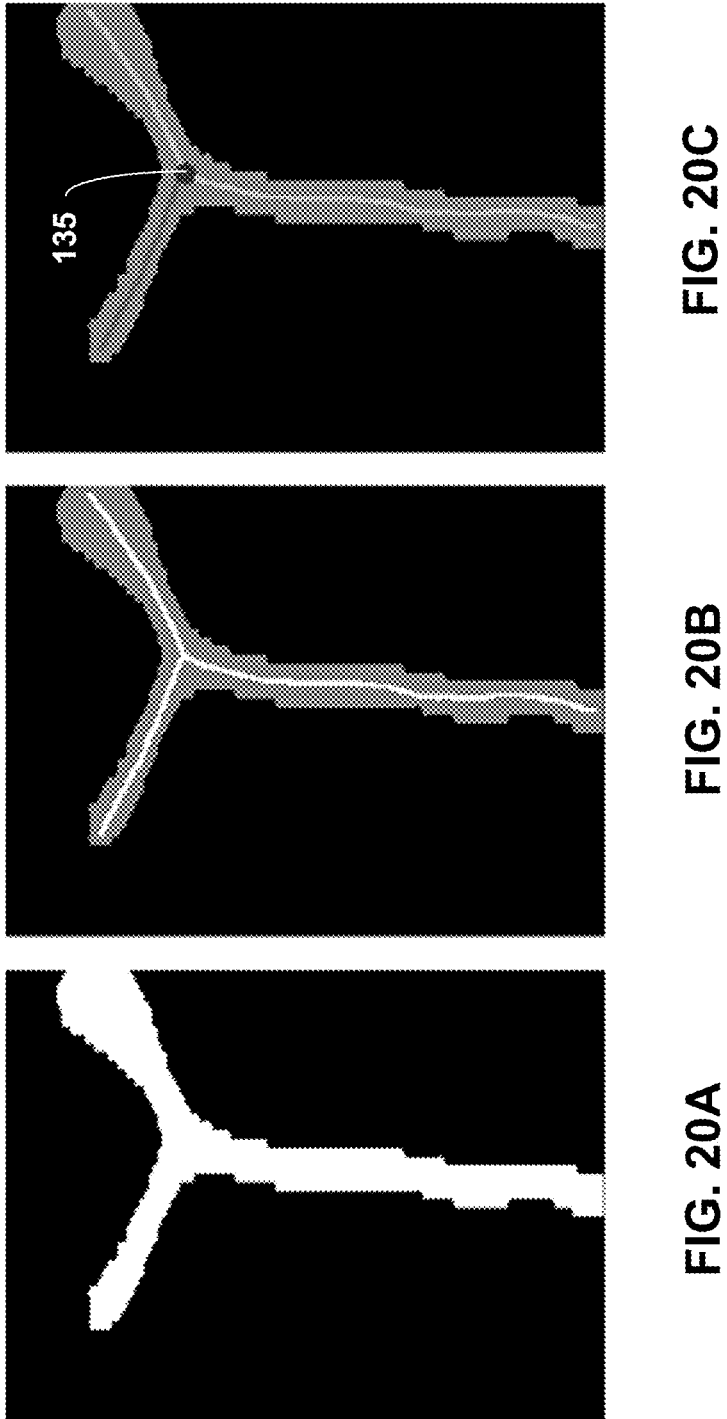
FIGS. 20A-20C are conceptual diagrams illustrating results of sagittal cuts through scapula for determining the transverse axis of FIG. 18.

FIGS. 20A-20C illustrate the result of one of the sagittal cuts of the FIGS. 19A and 19B. For instance, the sagittal cuts from a "Y" shape, as illustrated in FIG. 20A. Processing circuitry 102 may determine a skeleton line through the Y shape, as illustrated in FIG. 20B. For instance, processing circuitry 102 may determine dots that are equidistant to nearest border through the Y shape and interconnect the dots to form the line through Y shape as shown in FIG. 20B. Again, rather than skeleton, other points may be used like center points. Processing circuitry 102 may determine an intersection of the lines through the skeleton, as illustrated by intersection point 135. For instance, intersection point 135 may be common to all of the lines that together form the Y shape.

Processing circuitry 102 may repeat these operations for each of the Y shapes in each of the sagittal cuts, and determine respective intersection points, like intersection point 135. Processing circuitry 102 may determine a line that that intersects the plurality of the respective intersection points to determine an initial transverse axis 133B illustrated in FIGS. 21A and 21B.

Figures 21A, 21B:
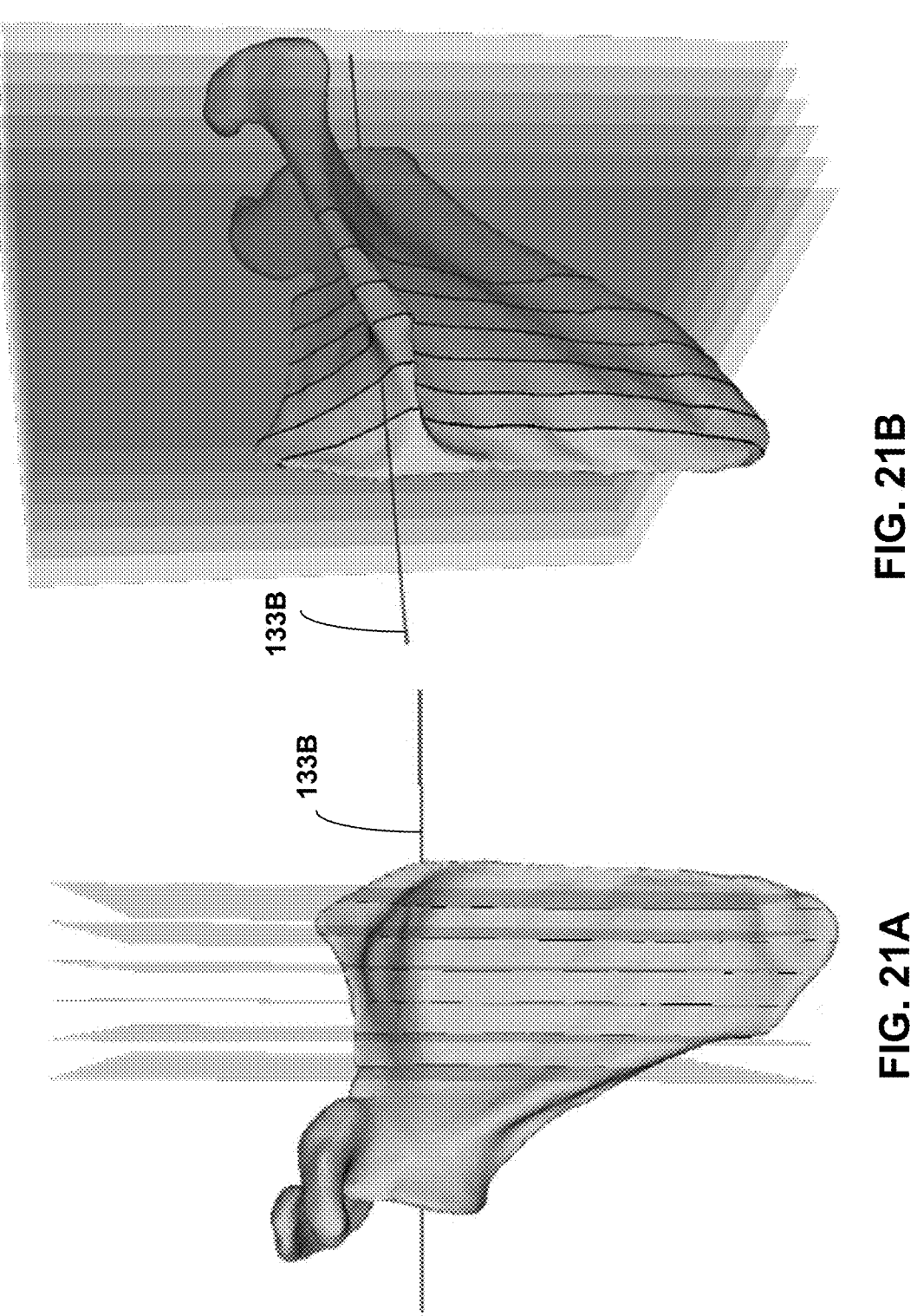
FIGS. 21A and 21B are conceptual diagrams illustrating another example of sagittal cuts through a scapula for determining the transverse axis of FIG. 18.

Processing circuitry 102 may determine sagittal cuts through the scapula using the initial transverse axis 133B. For instance, FIGS. 21A and 21B are different perspectives of sagittal cuts through scapula based on axis 133B. Processing circuitry 102 may repeat the operations described with respect to FIGS. 20A-20C to determine a plurality of intersection points for the sagittal cuts shown in FIGS. 21A and 21B. For example, similar to FIGS. 20A-20C, based on the sagittal cuts using axis 133B, each sagittal cut may form Y shapes, similar to FIG. 20A. Processing circuitry 102 may determine a skeleton line through the Y shapes, similar to FIG. 20B, and determine intersection points similar to FIG. 20C. Processing circuitry 102 may repeat these operations for each of the Y shapes in each of the sagittal cuts, and determine respective intersection points, similar to the description above for FIGS. 20A-20C. Processing circuitry 102 may determine a line that that intersects the plurality of the respective intersection points to determine transverse axis 134 illustrated in FIG. 18.

Figure 22:
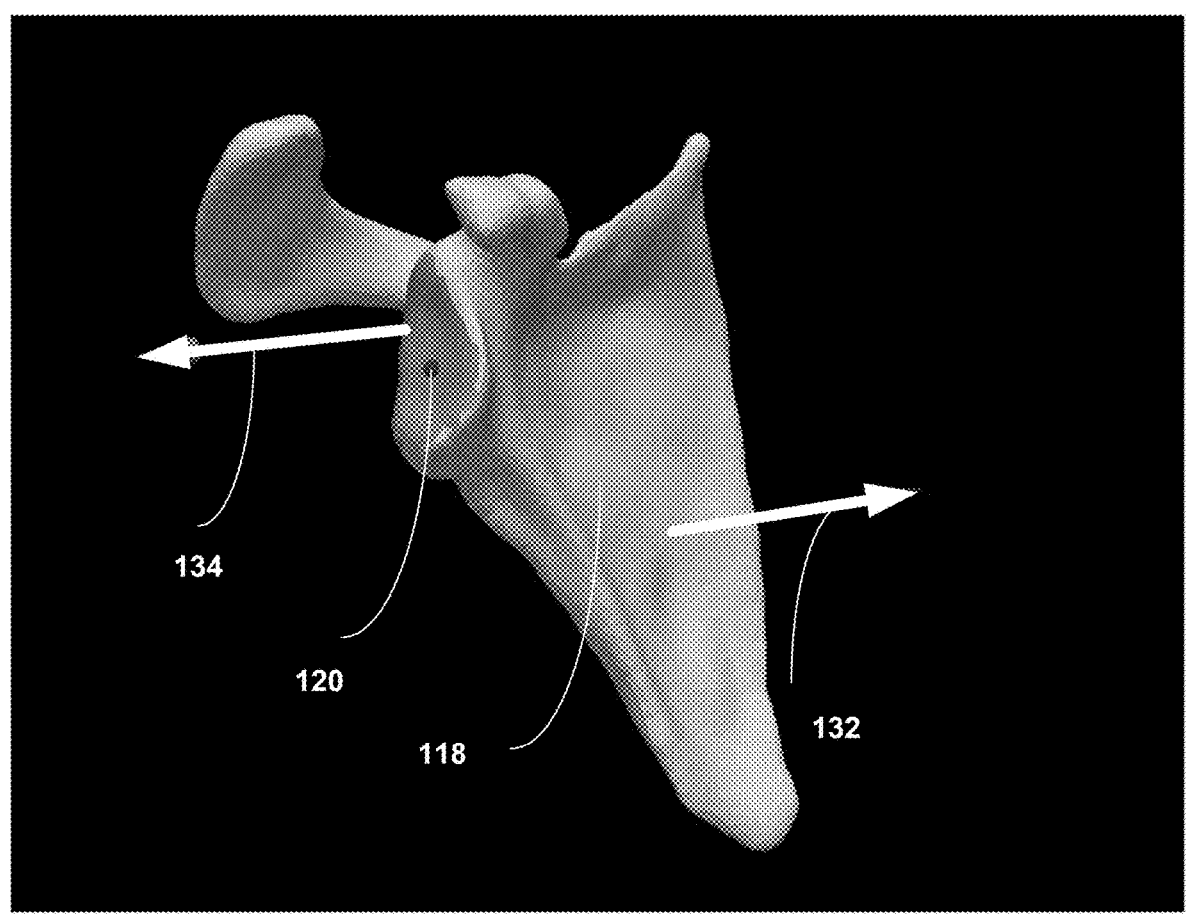
FIG. 22 is a conceptual diagram illustrating a transverse axis through a scapula and a normal line to a plane through the scapula for determining a coordinate system of a patient.

FIG. 22 is a conceptual diagram illustrating a transverse axis of FIG. 18 through a scapula and a normal line of FIGS. 16 and 17 to a plane through the scapula for determining a coordinate system of a patient. For example, FIG. 22 illustrates scapula 118 and glenoid center 120. FIG. 22 also illustrates vector 132 that is normal to plane 130 and illustrates transverse axis 134.

For example, as described above, an initial step for pre-morbid or morbid, pre-implant characterization is to determine a coordinate axis with which the segmented objects are aligned to shape model 106. With the example techniques described above, processing circuitry 102 may determine the x-axis (e.g., vector 132) and the z-axis (e.g., transverse axis 134). Processing circuitry 102 may further determine the y-axis using the below techniques. Once process circuitry 102 determines the coordinate system to represent and define location of anatomical objects determined from the segmentation of the image data of scans 108, processing circuitry 102 may be able to align the segmented object to the coordinate system of shape model 106.

Figure 23:
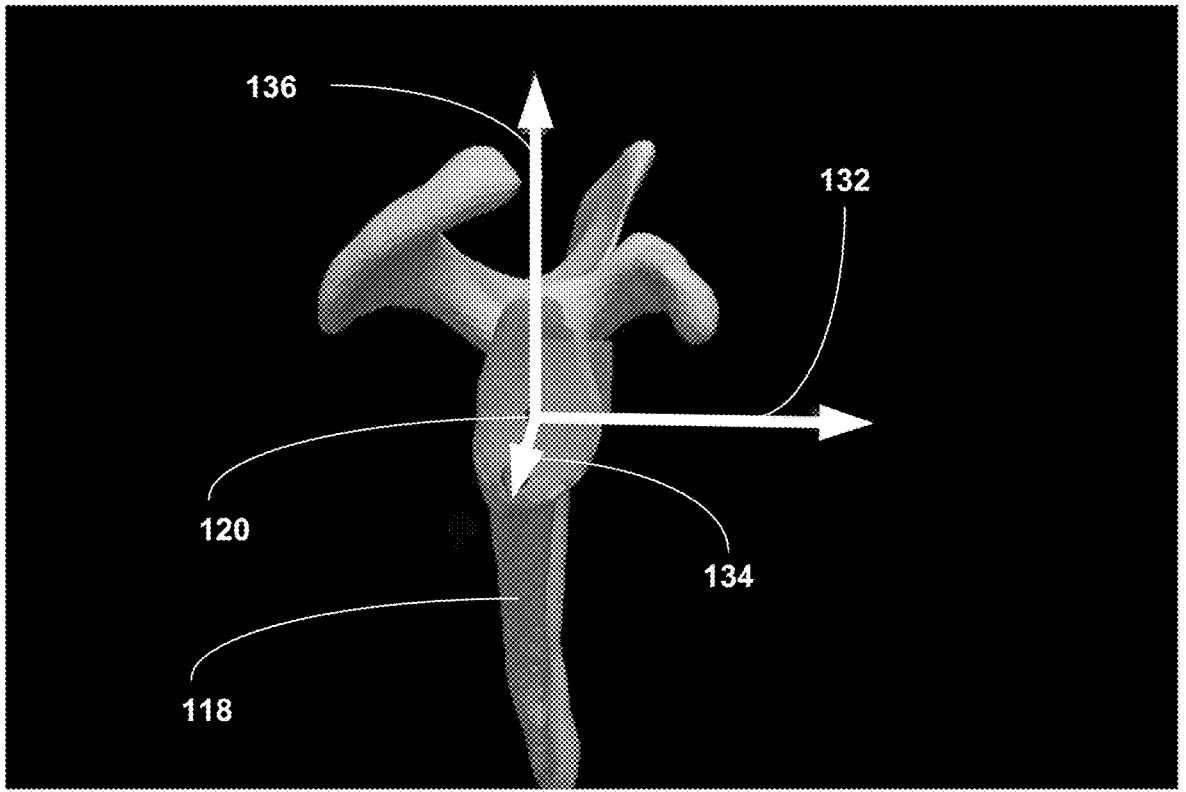
FIG. 23 is a conceptual diagram illustrating movement of a transverse axis through a scapula and a normal line to a plane through the scapula to a central location of a glenoid for determining a coordinate system of a patient.

FIG. 23 is a conceptual diagram illustrating movement (or extension) of a transverse axis through a scapula and a normal line to a plane through the scapula to a central location of a glenoid for determining a coordinate system of a patient. For instance, FIG. 8 illustrates the patient coordinate system centered around glenoid center 120. As illustrated, vector 132, as determined above, forms the x-axis of the patient coordinate system, transverse axis 134 forms the z-axis of the patient coordinate system, and axis 136 forms the y-axis of the patient coordinate system.

Processing circuitry 102 may determine a glenoid center based on a plurality of 2D and 3D operations. For example, processing circuitry 102 may determine a barycenter of the glenoid cavity and project the barycenter back to the glenoid cavity surface to determine glenoid center 120.

Processing circuitry 102 may then determine y-axis 136 based on x-axis 132, and z-axis 134. For example, processing circuitry 102 may determine $y'=z*x$, where * is the vector product. The $y'$ is perpendicular to the plane defined by the x-axis 132 and the z-axis 134, but x-axis 132 and z-axis 134 need not necessarily be perfectly orthogonal. Accordingly, processing circuitry 102 may replace z-axis 134 by $Z=x*y'$ or x-axis 132 by $X=y'*z$ to have an orthogonal system (x, y', Z) or (X, y', z). In some examples, processing circuitry 102 may utilize $Z=x*y'$ because the computation of x-axis 132 (e.g., the scapula normal) is more robust than the computation of z-axis 134 (e.g., transverse axis).

In this manner, processing circuitry 102 may determine the patient coordinate system. In some examples, such as those described above, processing circuitry 102 may determine the patient coordinate system without relying upon specific landmarks such as trigonum scapulae 122 and angulus inferior 124 that may not be present in segmentation of anatomical objects from the image data of scans 108 due to over or under segmentation. In particular, for this example technique, processing circuitry 102 may determine x, y, and z-axis without relying on specific anatomical objects, but rather, determine the x, y, and z-axis based on scapula 118 itself, which should be present in the image data of scans 108, whereas trigonum scapulae 122 and angulus inferior 124 may not be present in the image data of scans 108 due to under- or over-segmentation.

The various techniques described above for determining a patient coordinate system may, for example, be used for a patient who does not yet have an implant installed or for a patient who has a hemi implant installed, and hence does not have a scapula-side implant component. For patients with anatomical or reverse implants, this disclosure puts forth additional techniques for determining a patient coordinate system. These additional techniques were described above with respect to feature extraction unit 410 and FIGS. 6, 7A, and 7B. These additional techniques may be used either separately from or in conjunction with the techniques described above for determining a patient coordinate system.

In some cases for patient's with implants, most commonly anatomical implants or reverse implants, processing circuitry 102 may not be able to determine the x, y, and z-axis using the techniques described above with respect to the transverse axis and the scapula plane. Specifically, the transverse axis and the plane through the scapula may not be readily detectible in scans 108 due to the presence of the implant. For patients with implants, processing circuitry 102 may determine the x-, y-, and z-axis based on features of the implant, as determined by feature extraction unit 208 or feature extraction unit 410 described above with respect to FIGS. 6, 7A, and 7B.

After determining the patient coordinate system using either the transverse axis and the scapula plane or using the implant features, processing circuitry 102 may determine the transformation matrix to align the patient coordinate system to shape model 106. The alignment process is generally performed in the same manner regardless of the techniques used for determining the patient coordinate system. As described above, one example way to determine the transformation matrix is using the coordinate system where c=(x,y,z,o), and where x, y and z are the orthogonal basis 3D vectors and o is the origin (c is a 4×4 homogeneous matrix with the last raw is (0,0,0,1)). The new coordinate system to which the segmented object is to be transformed is C=(X, Y,Z,O). In this example, the transformation matrix is then: T=c^−1×C.

Figure 24:
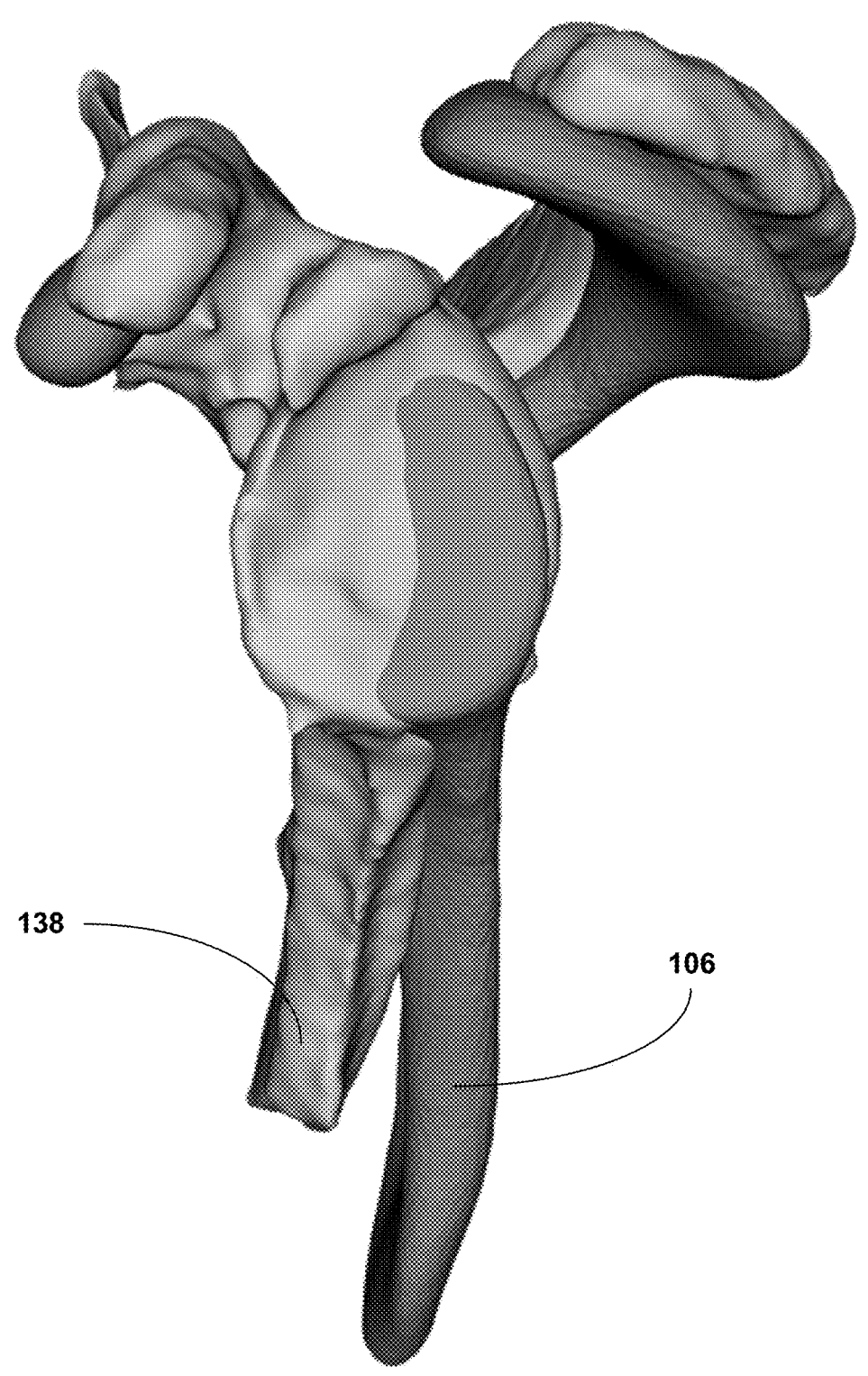
FIG. 24 is a conceptual diagram illustrating an example of an initial alignment of a segmentation object to a shape model.

Processing circuitry 102 may multiply the coordinates that define the segmentation object (e.g., where the coordinates are determined from the axes utilizing techniques described above) based on the image data from scans 108 with the transformation matrix to align the segmentation objects to shape model 106 (e.g., the SSM retrieved from memory 104). The result of this alignment may be an initial shape. For example, FIG. 24 illustrates initial aligned shape 138 that is aligned with shape model 106. Initial aligned shape 138 is shown as superimposed on shape model 106, in FIG. 24. Initial aligned shape 138 is generated based on the image data of scans 108 where certain portions of the anatomy may be missing (e.g., due to under-segmentation) or distorted (e.g., due to over-segmentation). For instance, initial aligned shape 138 may be generally positioned such that it has the same orientation on the x-, y-, and z-axis as shape model 106.

However, following transformation, initial aligned shape 138 may not be as closely aligned with shape model 106. In case the scapula is over-truncated inferiorly and/or medially (which may not be known but is the case in initial shape 138), there could be computational errors in determining the scapula body normal (e.g., vector 132) and the transverse axis 134. These computational errors may lead to misalignment between the shape model 106 and the patient anatomy (e.g., scapula 118), and therefore, initial aligned shape 138 may not be as closely aligned with shape model 106 as desirable. For example, as can be seen from FIG. 24, initial aligned shape 138 is rotated along z-axis (e.g., transverse axis) 134.

In one or more examples, because it may be unknown whether there is misalignment from over-truncated scapular 118, processing circuitry 102 may modify parameters of initial shape 138 to generate an aligned shape. The aligned shape is substantially proximal (e.g., in location, size, and orientation) to shape model 106. As one example, to modify parameters, processing circuitry 102 may iteratively adjust coordinates of initial aligned shape 138 so that the initial aligned shape model rotates along the z-axis (e.g., the points of initial aligned shape 138 rotate along the z-axis). At each adjustment, processing circuitry 102 may determine a distance between the initial aligned shape 138 and shape model 106 (e.g., points in the initial aligned shape and points represented in shape model 106).

For instance, processing circuitry 102 may determine the distances between points on initial aligned shape 138 (e.g., such as points of acromion and the coracoid) and corresponding points on shape model 106 (e.g., acromion and coracoid on shape model 106). The corresponding points refer to points in the initial aligned shape 138 and points in shape model 106 that identify the same patient anatomy. Processing circuitry 102 may keep rotating the initial aligned shape 138 until the distance between the initial aligned shape 138 and shape model 106 about the z-axis 134 satisfies a threshold (e.g., less than threshold including where distance is minimized). Then, processing circuitry 102 may rotate the initial aligned shape 138 along the y-axis 138 until the difference in points between initial aligned shape 138 and corresponding points in shape model 106 about the y-axis satisfies a threshold (e.g., less than threshold including where distance is minimized). Processing circuitry 102 may rotate the initial aligned shape model about the x-axis 132 until the difference in points between initial aligned shape 138 and corresponding points in shape model 106 along the x-axis 132 satisfies a threshold (e.g., less than threshold including where distance is minimized).

As one example, processing circuitry 102 may modify the parameters of the initial aligned shape 138 so that the initial aligned shape 138 rotates 5-degrees along an axis (e.g., a first instance of the initial aligned shape model) within a search range of [−45-degrees, 45-degrees] or [−27 degrees, 27 degrees]. Processing circuitry 102 may determine the distance between points of the first instance of the initial aligned shape 138 and corresponding points of shape model 106. Assuming the distance is not at a minimum or less than threshold, next, processing circuitry 102 may modify the parameters of the initial aligned shape 138 so that the initial aligned shape rotates 10-degrees along the axis (e.g., a second instance of the initial aligned shape 138) and determine the distance (e.g., between points of the second instance of the initial aligned shape 138 and corresponding points of shape model 106). Processing circuitry 102 may repeat these operations about each of the axes for each instance of the initial aligned shape 138. Processing circuitry 102 may keep repeating these operations until processing circuitry 102 determines an instance of the initial aligned shape 138 that resulted in a distance less than a threshold (such as the minimum distance). The instance of the initial aligned shape 138 that resulted in the distance being less than threshold (including example of minimum distance) among the various iterative instances is selected as aligned shape 140, illustrated in FIG. 25.

Figure 25:
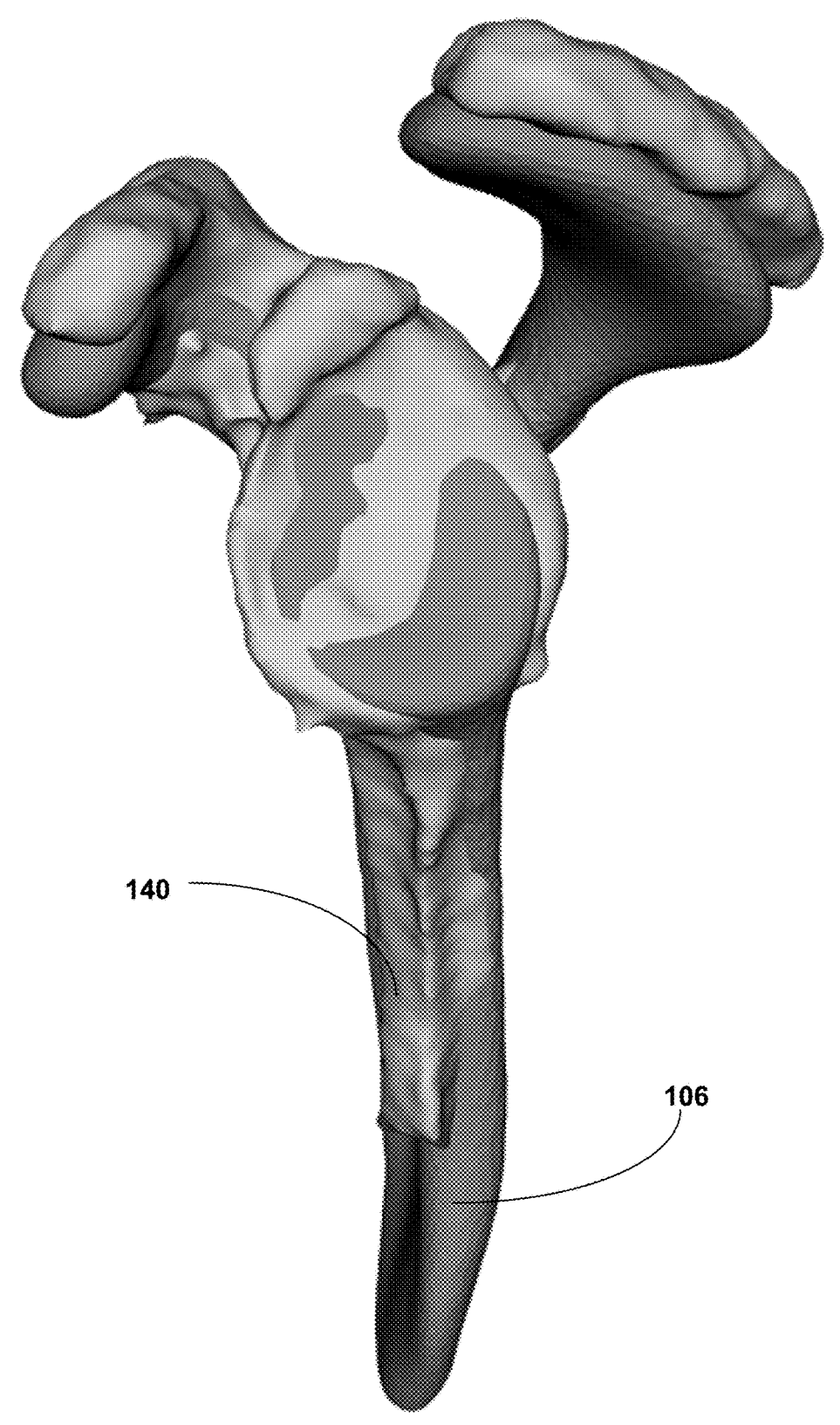
FIG. 25 is a conceptual diagram illustrating an example of an intermediate alignment of a segmentation object to a shape model.

The result of these operations may be the aligned shape (e.g., a model that has been rotated along the x, y, and z-axes). For example, FIG. 25 illustrates aligned shape 140 that is aligned to shape model 106. Aligned shape 140 is shown as superimposed on shape model 106, in FIG. 25. Aligned shape 140 (e.g., simply aligned shape 140) provides a better alignment to shape model 106 as compared to initial aligned shape 138. For instance, as shown in FIG. 25, aligned shape 140 is better aligned to shape model 106 than initial aligned shape 138 to shape model 106, as shown in FIG. 24.

For instance, initial aligned shape 138 and shape model 106 may be generally aligned. However, there may be some tilting or misorientation between the initial aligned shape 138 and shape model 106 due to the over or under segmentation of the image data of anatomical objects in scans 108. To address this, processing circuitry 102 may separately rotate initial aligned shape 138 about each axis (x, y, z) until the distance between initial aligned shape 138 and shape model 106 satisfies a threshold (e.g., minimized). Accordingly, by iteratively rotating initial aligned shape 138, processing circuitry 102 may generate aligned shape 140 (also called intermediate aligned shape 140). Because the distance between points on aligned shape 140 and corresponding points of shape model 106 may be minimized, aligned shape 140 (e.g., intermediate aligned shape 140) is substantially in the coordinate system of shape model 106.

Aligned shape 140 may be referred to as an intermediate aligned shape because in some examples, shape model 106 is deformed to the shape of aligned shape 140 to generate the pre-morbid or morbid, pre-implant characteristics of the patient anatomy. Processing circuitry 102 may utilize techniques described below to deform shape model 106 to register shape model 106 to aligned shape 140. However, in some examples, processing circuitry 102 may utilize some other techniques to deform shape model 106 to register to aligned shape 140. Also, for the example techniques to register shape model 106 to aligned shape 140, it may be possible that such techniques are preformed where aligned shape 140 is generated using techniques other than those described above.

As described above, processing circuitry 102 may be configured to register shape model 106 to aligned shape 140. Registering shape model 106 to aligned shape 140 may refer to iteratively deforming shape model 106 until a cost function value is below a threshold (e.g., minimized). The registering algorithm is a global loop that includes two inner iterative loops referred to as iterative closest point (ICP) loop and elastic registration (ER) loop. There may be other example ways in which to perform the registering algorithm, and the use of two loops within a global loop is just one example way in which to perform the registering algorithm. For instance, in some examples, it may be possible to bypass the ICP loop and only perform the ER loop. In some examples, it maybe possible to perform only the ICP loop and bypass the ER loop.

In the ICP loop for the first iteration of the global loop, the initial input is aligned shape 140 and shape model 106. For the ICP loop in the first iteration of the global loop, processing circuitry 102 iteratively modifies aligned shape 140 based on a comparison of aligned shape 140 to shape model 106 to generate a first order shape. For example, for each iteration through the ICP loop, processing circuitry 102 determines a cost value, and the modified aligned shape that results in the cost value less than a threshold (e.g., minimized) is the output of the ICP loop and is referred to a first order shape. An example of the ICP algorithm is described in more detail below.

The first order shape is an input into the ER loop for the first iteration of the global loop. Another input into the ER loop, for the first iteration of the global loop, is shape model 106. For the ER loop in the first iteration of the global loop, processing circuitry 102 may deform shape model 106 to generate a plurality of estimated shape models (e.g., one for each time through the ER loop). For each loop of the ER loop, processing circuitry 102 may determine a total cost value, and determine which iteration of the ER loop utilized the estimated shape model having the total cost value that satisfies the threshold (e.g., less than threshold including where minimized). The result of the ER loop (e.g., the estimated shape model having the total cost value that satisfies the threshold) is a first order registered shape model. This completes one iteration of the global loop. The total cost value, for the first iteration of the global loop, may be based on distances and orientation between the estimated shape models and the first order shape, constraints on medialization of anatomy, and parameter weighting.

For example, assume that S1 is the first order shape model that processing circuitry 102 is to determine using the ER loop in the first iteration of the global loop. For the ER loop, processing circuitry 102 may generate S11, S12, S13, and so forth, where each one of S11, S12, S13, and so forth is a deformed version of shape model 106 and S11, S12, S13, and so forth are each an example of an estimated shape model. For each of one of S11, S12, S13, and so forth, processing circuitry 102 may determine a total cost value (e.g., S11_total cost value, S12_total cost value, S13_total cost value, and so forth). Processing circuitry 102 may determine which of the total cost values is the less than a threshold (e.g., minimized). The estimated shape model (e.g., one of S11, S12, S13, and so forth) having the total cost value that is below a threshold (e.g., minimized) is S1 (e.g., the first order registered shape model). After this, the first iteration of the global loop is complete.

For the second iteration of the global loop, processing circuitry 102 performs the operations of the ICP loop. In the second iteration of the global loop, for the ICP loop, one input is the first order shape model, generated from the ER loop, and the other input is the first order shape, generated by the previous ICP loop. In the second iteration of the global loop, for the ICP loop, processing circuitry 102 iteratively modifies the first order shape based on a comparison of the first order shape to the first order shape model. For instance, for each iteration through the ICP loop, processing circuitry 102 determines a cost value, and the modified first order shape that results in the cost value less than a threshold (e.g., minimized) is the output of the ICP loop and is referred to a second order shape.

The second order shape is an input into the ER loop for the second iteration of the global loop. Another input into the ER loop, for the second iteration of the global loop, is shape model 106 and/or the first order shape model. Where shape model 106 is used, the values of $b_i$ may range within $[-b+b]$. Where the first order shape model is used, the values of $b_i$ may range within $[-b+b\_prev\ b+b\_prev]$, where b_prev is the value found in the previous iteration (e.g., used to determine the first order shape model).

For the ER loop in the second iteration of the global loop, processing circuitry 102 may deform shape model 106 and/or the first order shape model to generate a plurality of estimated shape models (e.g., one for each iteration of the ER loop). For each iteration of the ER loop, processing circuitry 102 may determine a total cost value, and determine which iteration of the ER loop utilized the estimated shape model having the total cost value that satisfies the threshold (e.g., minimized). The result of the ER loop, in the second iteration of the global loop, (e.g., the estimated shape model having the total cost value that satisfies the threshold) is a second order shape model. This completes a second iteration of the global loop. The total cost value, for the second iteration of the global loop, may be based on distances and orientation between the estimated shape models and the second order shape, constraints on medialization of anatomy, and parameter weighting.

For example, assume that S2 is the second order shape model that processing circuitry 102 is to determine using the ER loop in the second iteration of the global loop. For the ER loop, processing circuitry 102 may generate S21, S22, S23, and so forth, where each one of S21, S22, S23, and so forth is a deformed version of shape model 106 and/or the first shape model and S21, S22, S23, and so forth are each an example of an estimated shape model. For each of one of S21, S22, S23, and so forth, processing circuitry 102 may determine a total cost value (e.g., S21_total cost value, S22_total cost value, S23_total cost value, and so forth). Processing circuitry 102 may determine which of the total cost values is the less than a threshold (e.g., minimized). The estimated shape model (e.g., one of S21, S22, S23, and so forth) having the total cost value that is below a threshold (e.g., minimized) is S2 (e.g., the second order registered shape model). After this, the second iteration of the global loop is complete.

In the above example, processing circuitry 102 generated S11, S12, S13, and so forth (e.g., first set of estimated shape models) for the first iteration of the global loop and generated S21, S22, S23, and so forth (e.g., second set of estimated shape models) for the second iteration of the global loop. In some examples, the number of estimated shape models in the first and second set of estimated shape models may be the same. In some examples, the number of estimated shape models in the first and second set of estimated shape models may be different (e.g., 6 estimated shape models in the first set of estimated shape models and 14 estimated shape models in the second set of estimated shape models). One reason for having different numbers of estimated shape models in different iterations of the global loop is that by increasing the number of estimated shape models in subsequent iterations of the global loop, it may be possible to more accurately determine a global minimum as compared to if the same or fewer number of estimated shape models is used. That is, processing circuitry 102 may gradually increase the number of unknowns (e.g., modes and scale factors) used to generate the estimated shape models through multiple ER loops.

This process keeps repeating until the total cost value is below a threshold (e.g., minimized). The registered shape model (e.g., Ni order registered shape model) that provides the total cost value below a threshold (e.g., minimized) provides a pre-morbid or morbid, pre-implant characterization of the patient anatomy. Some additional processing may be needed to bring back the pre-morbid or morbid, pre-implant characterization into the patient coordinate system.

As described above, for determining the pre-morbid or morbid, pre-implant characterization, there is a global loop that includes an ICP loop and an ER loop. The following describes an example of the ICP loop. In the ICP loop, there is a source point clout and a target point cloud. The target point cloud remains fixed and processing circuitry 102 or projection unit 212 modifies (e.g., transforms) the source point cloud such that the transformed point cloud matches the target point cloud. A difference between the transformed point cloud and the target point cloud indicates how well of a match the transformed point cloud is to the source cloud. In one or more examples, processing circuitry 102 or projection unit 212 keeps transforming the source point cloud until the difference is below a threshold. For instance, processing circuitry 102 or projection unit 212 keeps transforming the source point cloud until the difference is minimized.

In one or more examples, in the first iteration of the global loop, for the ICP loop, the target point cloud is shape model 106 and the source point cloud is aligned shape 140. Processing circuitry 102 or projection unit 212 may determine distances between points on aligned shape 140 and corresponding points on shape model 106. The points on aligned shape 140 that are used may be points that are known not be pathological (e.g., medial glenoid vault, the acromion, and the coracoid, as a few non-limiting examples). Other examples include various other points on the scapula that are present in the image data of scans 108. Processing circuitry 102 or projection unit 212 may find points for the same anatomy on shape model 106.

Figure 26:
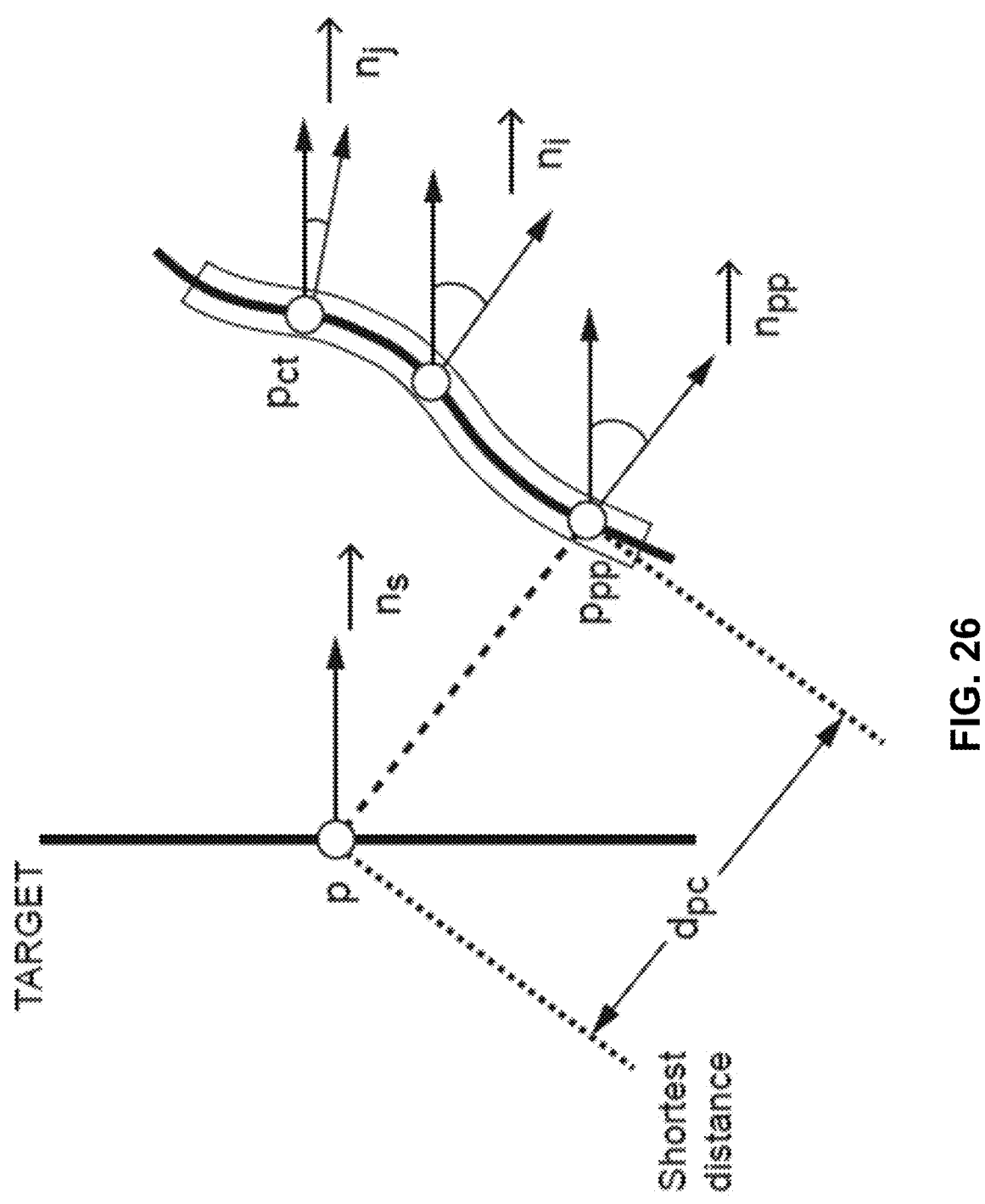
FIG. 26 is a conceptual diagram illustrating an example for determining difference values for an ICP algorithm.

FIG. 26 is a conceptual diagram illustrating an example for determining difference values for ICP algorithm. For example, processing circuitry 102 or projection unit 212 may determine a point (p) on target point cloud (e.g., shape model 106). Processing circuitry 102 or projection unit 212 may then determine closest point to point p on aligned shape 140, which in the example of FIG. 26 is point $p_{pp}$. Processing circuitry 102 or projection unit 212 may determine a set number of points (e.g., 10 points) that are proximate to point $p_{pp}$ on aligned shape 140 such as $p_{ct}$, illustrated in FIG. 26.

For point p on shape model 106 and each of these points (e.g., closest point and proximate points on aligned shape 140), processing circuitry 102 or projection unit 212 may determine a normal vector. For example, vector ns is the normal vector for point p, vector npp is the normal vector for point $p_{pp}$, and vector nj is the normal vector for point $p_{ct}$. One way to determine the normal vectors is based on vectors orthogonal to a tangential plane to the point. Another way to compute a point's normal is to calculate the normal of each triangle that shares that point and then attribute the mean normal. In order to overcome local noise, normals are smoothed by computing the mean normal of points within a specific vicinity.

Processing circuitry 102 or projection unit 212 may determine an orientation and distance difference between point p on shape model 106 and points on aligned shape 140 based on the following equation:

$$\text{Difference} = norm(p_s - p_t)^2 + w * norm(n_s - n_t)^2.$$

In the above equation, $p_s$ is a source point (e.g., point p on shape model 106), pt is point on aligned shape 140 (e.g., closest point and proximate points such as point $p_{pp}$ or $p_{ct}$), ns is the normal vector of point ps (e.g., ns as shown in FIG. 26), nt is the normal vector of point on aligned shape 140 (e.g., npp and nj), and w is a pre-programmed weighting factor. Typically, w equals 1 to give equal weights between distance and orientation. In some examples, high/low curvature regions may require higher/lower values of 'w'. The value of 'w' may be defined empirically.

Processing circuitry 102 or projection unit 212 may determine which of the difference values resulted in the smallest different value. For example, assume that a first difference value is based on p, ns, $p_{pp}$, and $n_{pp}$ and a second difference value is based on p, ns, $p_{ct}$, and $n_j$. In this example, the second difference value may be smaller than the first difference value. Processing circuitry 102 or projection unit 212 may determine $p_{ct}$ on aligned shape 140 as a corresponding point to point p on shape model 106.

Although FIG. 26 illustrates one point p on shape model 106, there may be plurality (e.g., N number) of points on shape model 106, and processing circuitry 102 or projection unit 212 may perform operations similar to those described above to identify N corresponding points on aligned shape 140 for each of the N points on shape model 106. Accordingly, there may be N difference values. Processing circuitry 102 or projection unit 212 may sum together the N difference values and divide the result by N. If the resulting value is greater than a threshold (e.g., including examples where the resulting value is not minimized), processing circuitry 102 or projection unit 212 may continue with the ICP loop.

With the N points on shape model 106 and the N points on aligned shape, processing circuitry 102 or projection unit 212 may determine a rotation matrix, R, and a translation vector, t. Based on the rotation matrix and the translation vector, processing circuitry 102 or projection unit 212 may rotate and translate the points on aligned shape 140 (e.g., −R multiplied by (points on aligned shape) plus translation vector). The result is a first intermediate first order shape. One example way of generating the rotation matrix R and the translation vector t is described in Berthold K. P. Horn (1987), "Closed-form solution of absolute orientation using unit quaternions," https://pdfs.semanticscholar.org/3120/a0e44d325c477397afcf94ea7f285a29684a.pdf.

This may conclude one instance of the ICP loop. Processing circuitry 102 or projection unit 212 may then repeat these operations where processing circuit 102 or projection unit 212 uses the first intermediate first order shape, in place of aligned shape 140, and shape model 106. Processing circuitry 102 or projection unit 212 may determine N difference values for each of the N points on shape model 106 and the N points on the intermediate first order shape. Processing circuitry 102 or projection unit 212 may sum together the N difference values and divide by N. If the resulting value is greater a threshold (or not minimized), processing circuitry 102 or projection unit 212 may determine the rotation matrix and the translation vector and determine a second intermediate first order shape. This may conclude a second iteration through the ICP loop.

Processing circuitry 102 or projection unit 212 may keep repeating these operations until processing circuitry 102 or projection unit 212 determines a value resulting from the sum of N difference values between the N points on shape model 106 and the N points on the Xth intermediate first order shape being divided by N where the value satisfies a threshold (such as when the value is minimized). In this case, the ICP loop is concluded and processing circuitry 102 or projection unit 212 determines that the Xth intermediate first order shape is the first order shape.

The first order shape becomes an input into the elastic registration (ER) loop. Another input in the ER loop is shape model 106. In the ER loop, processing circuitry 102 or projection unit 212 may determine a plurality of estimated shape models based on shape model 106. For instance, processing circuitry 102 or projection unit 212 may determine a new shape model ($s_i$) based on the following equation:

$$s_i = s' + \sum_i b_i \sqrt{\lambda_i} \times v_i.$$

In the above equation, s' is shape model 106 (e.g., point cloud of mean shape as one example, where point cloud defines coordinates of points within shape model 106, such as vertices of primitives that form shape model 106). In the equation, $\lambda_i$ is the eigenvalues and $v_i$ is the eigenvectors of the covariance matrix respectively (also called modes of variations). The covariance matrix represents the variance in a dataset. The element in the i, j position is the co-variance between the i-th and j-th elements of a dataset array.

Processing circuitry 102 or projection unit 212 may determine the plurality of estimated shape models by selecting different values of $b_i$. In the above, $b_i$ is a scaling factor to scale the eigenvalues or eigenvectors. The eigenvalue ($\lambda_i$) the eigenvector ($v_i$) are known from the generation of shape model 106 (e.g., s'). For ease of illustration, assume that processing circuitry 102 or projection unit 212 determined 10 estimated shape models based on 10 selected (e.g., randomly or pre-programmed) values of $b_i$. There may be more or fewer than 10 estimated shape models.

In the ER loop, processing circuitry 102 or projection unit 212 may perform the following operations on the estimated shape models. As part of the ER loop, processing circuitry 102 or projection unit 212 may determine which of the estimated shape models produces a cost function value that is below a threshold (e.g., minimized). The cost function value may be based on three sub-cost function values, although more or fewer than the three sub-cost function values are possible. For example, assume that the first sub-cost function value is Cf1, the second sub-cost function value is Cf2, and the third sub-cost function value is Cf3. In some examples, the cost function value (Cf) is equal to Cf1+Cf2+Cf3. In some examples, weights may be applied, such that Cf=w1*Cf1+w2*Cf2+w3*Cf3, 0<wi<1 and 0≤Cfi≤1. The weights (wi) may be pre-programmed. To complete the ER loop, processing circuitry 102 or projection unit 212 may determine which of the estimated shape model generates a Cf value that satisfies a threshold (e.g., less than threshold including minimized).

A first sub-cost function value (Cf1) is based on distances and orientation between the estimated shape models (e.g., generated based on different values for $b_i$) and the first order shape generated by the ICP loop. For instance, for each of the estimated shape models, processing circuitry 102 or projection unit 212 may determine a Cf1 value. The equation for Cf1 may the same as the equation used for the ICP loop.

For example, Cf1=$\Sigma$norm($p_s-p_t$)$^2$+w*norm($n_s-n_t$)$^2$/N. However, in this case, $p_s$ and $n_s$ are for points and vectors of those points on each of the estimated shape models, and $p_t$ and $n_t$ are for points and vectors of those point on the first order shape. N refers to the number of points on the first order shape and on each of the estimated shape models.

Processing circuitry 102 or projection unit 212 may determine the value for Cf1 using the above example techniques described for the ICP loop. For example, for a first estimated shape model, processing circuitry 102 or projection unit 212 may determine a value of Cf1 (e.g., first Cf1), for a second estimated shape model, processing circuitry 102 or projection unit 212 may determine a value for Cf1 (e.g., second Cf1), and so forth. In this case, processing circuitry 102 or projection unit 212 may not perform any translation or rotation of any of the estimated shape models but utilize the calculation of Cf1 for each of the estimated shape models to select one of the estimated shape models.

The value of Cf1 is one of the sub-cost function values used to determine the cost function value of the ER loop. In some examples, it may be possible to determine the estimated shape model that minimizes the Cf1 value and end the ER loop. However, simply minimizing the difference (e.g., distance of points) between the output of the ICP loop and the estimated shapes generated from shape model 106 may not be sufficient to determine the pre-morbid or morbid, pre-implant characterization of the patient anatomy. For example, there may be logical constraints on the location of the shape generated by the ICP loop (e.g., the first order shape after the initial conclusion of the ICP loop) relative to the patient's body and minimizing the difference (e.g., distances) between the first order shape and the estimated shapes may possibly violate such logical constraints. For example, the sub-cost function value, Cf1, can be non-convex for some cases and therefore may lead to a local minimum that is incorrect. With additional sub-cost function values, processing circuitry 102 or projection unit 212 may correct for the non-convexity of the total cost function value, Cf.

For example, when predicting the pre-morbid or morbid, pre-implant characterization of the glenoid, the glenoid of the estimated shape models should not be more medialized than the current patient glenoid. In this disclosure, medialized or medial means towards the center of the patient's body. When the patient suffers injury or disease at the glenoid, the bone erosion may cause the pathological glenoid to be more medial (e.g., shift closer to the middle of the patient's body) than prior to the injury or aliment. Therefore, a glenoid on an instance of one of the estimated shape models that is more medial than the current glenoid is more than likely not a proper estimate of the pre-morbid or morbid, pre-implant patient anatomy. Again, the injury or disease may have caused the glenoid to become more medial, and therefore, if one of the estimated shape models includes a glenoid that is more medial than the current position of the glenoid, the instance of the estimated shape model may not have the pre-morbid or morbid, pre-implant characteristics of the patient anatomy.

That is, assume that a first estimated shape model, generated from shape model 106, minimized the value of Cf1 based on distances and orientation between the first estimated shape model and the first order shape generated by the ICP loop. In this example, if the glenoid of the first estimated shape model is more medial than the current position of the glenoid, the first estimated shape model may not be the correct or best estimate of the pre-morbid or morbid, pre-implant shape of the pathological anatomy.

To ensure that medialized instances of the estimated shape models are not used to determine the pre-morbid or morbid, pre-implant characterization, processing circuitry 102 may determine the value of Cf2. The value of Cf2 indicates whether the estimated shape model is more or less medial than the patient anatomy. That is, a second example sub-cost function value is Cf2. The value of Cf2 is a measure of constraints on medialization of anatomy.

Figure 27A:
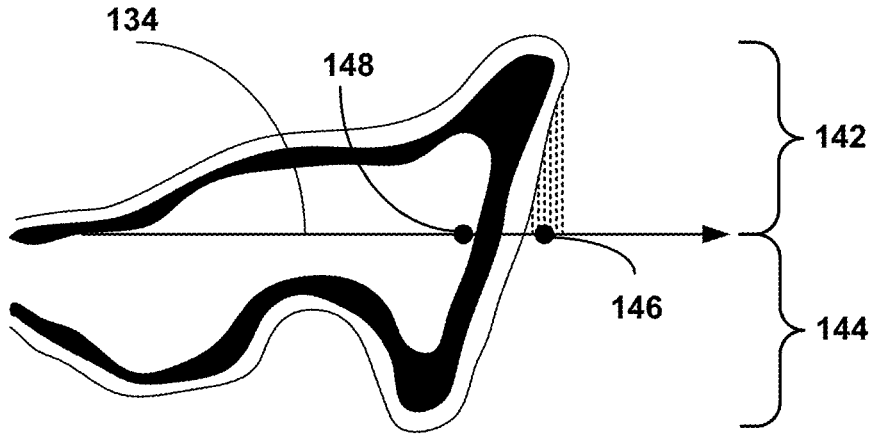
FIGS. 27A and 27B are conceptual diagrams illustrating portions of a glenoid for determining parameters of a cost function used to determine a pre-morbid shape of anatomy of a patient.
Figure 27B:
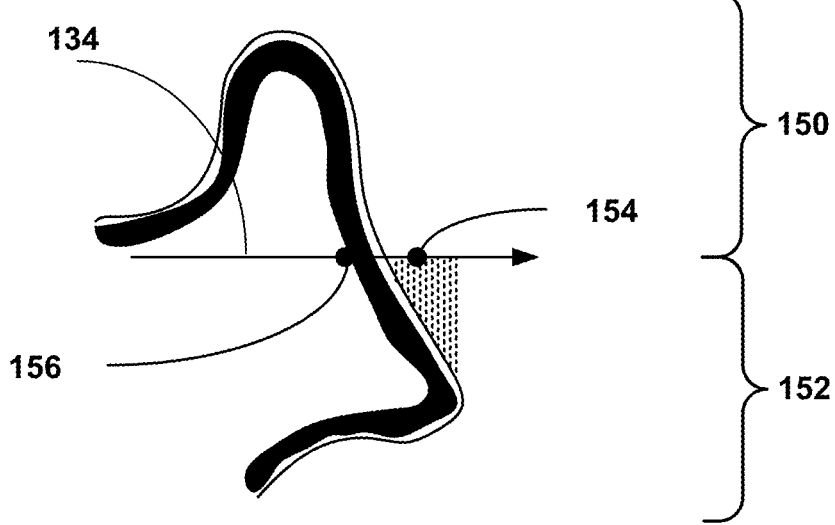

To determine the value of Cf2, processing circuitry 102 may determine a threshold point ($p_{th}$) laying on transverse axis 134 of the patient anatomy (e.g., pathological scapula). The point $p_{th}$ represents a threshold of the glenoid medialization that should be crossed by an instance of the intermediate shape model used to determine the pre-morbid characterizations. FIGS. 27A and 27B illustrate example ways in which to determine $p_{th}$. For example, processing circuitry 102 may divide image data from scans 108 of the glenoid into four quarters of interest (e.g., superior, posterior, inferior, and anterior).

FIGS. 27A and 27B are conceptual diagrams illustrating portions of a glenoid for determining parameters of a cost function used to determine a pre-morbid or morbid, pre-implant shape of anatomy of a patient. As described in more detail, with the illustrated portions of the glenoid in FIGS. 27A and 27B, processing circuitry 102 may determine a value of $p_{th}$. Processing circuitry 102 may also determine medialization values for each of the estimated shape models (e.g., generated from shape model 106 using values for $b_i$ and based on the eigenvalues and eigenvectors as described above). Based on the value of $p_{th}$ and the medialization values, processing circuitry 102 may determine a sub-cost value for Cf2.

FIG. 27A illustrates transverse axis 134 (e.g., as described above) that divides a glenoid surface into anterior side 142 and posterior side 144. FIG. 27B illustrates transverse axis 134 that divides a glenoid surface into superior side 150 and inferior side 152. For instance, referring back to FIG. 18, processing circuitry 102 determined transverse axis 134. Then, processing circuitry 102 may determine anterior side 142, posterior side 144, superior side 150, and inferior side 152 based on axial or sagittal cuts through scapula 118. The result may be the example illustrated in FIGS. 27A and 27B.

Processing circuitry 102 may project points on the glenoid surface for each of the portions (e.g., anterior and posterior sides of FIG. 27A and superior and inferior sides of FIG.

27B) to transverse axis 134 and determine a center of mass of the projected points of each portion. Point projection onto a line is the closest point on that line. The line and the vector defined by the point and its projection are perpendicular. This can be calculated by choosing a random point on the line which forms a hypotenuse with the point to be projected. Using trigonometry, the projection is the hypotenuse length multiplied by the cosine of the angle defined by the hypotenuse and the line. The center of mass is the mean point of the projected points on that line and can also be considered as the barycenter.

For example, point 146 in FIG. 27A is an example of the center of mass of projected points for anterior side 142. Point 148 in FIG. 27A is an example of the center of mass of projected points for posterior side 144. Point 154 in FIG. 27B is an example of the center of mass of projected points for superior side 150. Point 156 in FIG. 27B is an example of the center of mass of projected points for inferior side 152.

In one or more examples, processing circuitry 102 may determine a most lateral barycenter point (e.g., the point that is furthest away from the center of the patient's body) from points 146, 148, 154, and 156. Processing circuitry 102 may set the most lateral barycenter point as the threshold point $p_{th}$. Processing circuitry 102 may also determine the most lateral quarter as $Q_{th}$. In some examples, the most lateral barycenter point need not necessarily be in the most lateral quarter. For example, assume that the point 156 is the most lateral barycenter point (e.g., threshold point $p_{th}$). In this example, the most lateral quarter ($Q_{th}$) may be inferior side 152 if the most lateral barycenter point were in the most lateral quarter. However, it is possible that the most lateral barycenter point is not in the most lateral quarter.

Processing circuitry 102 may determine a corresponding quarter in the instance of the estimated shape models with the $Q_{th}$ quarter (e.g., most lateral quarter). Processing circuitry 102 may project the points of the quarter of the instance of the estimated shape models to transverse axis 134. For example, for each of the estimated shape models, processing circuitry 102 may determine points like points 146, 148, 154, and 156 for each of the estimated shape models. However, because of the different medialization of the estimated shape models (e.g., due to the different values of bi used to generate the estimated shape models), the respective projected points may be at different locations on the transverse axis 134.

For example, processing circuitry 102 may determine an anchor point on transverse axis 134. This anchor point is in the same location on transverse axis 134 for each of the estimated shape models. Processing circuitry 102 may determine distances of the projected points to the anchor point. In some examples, $p_{th}$ may be the anchor point.

Processing circuitry 102 may determine the distance of the projected points to $p_{th}$. Processing circuitry 102 may determine an average of the distances of the projected points as a value equal to $d_{med}$.

If the value of $d_{med}$ is zero or positive, it means that the instance of the estimated shape model is more medial than the current patient anatomy (e.g., glenoid and scapula), and therefore not a good predictor for the pre-morbid or morbid, pre-implant characteristics of the patient anatomy. If the value of $d_{med}$ is negative, it means that the instance of the estimated shape model is less medial than the current patient anatomy, and therefore may be a possible predictor for the pre-morbid or morbid, pre-implant characteristics of the patient anatomy.

In some examples, processing circuitry 102 may set Cf2 equal to a value based on $d_{med}$ (e.g., Cf2 is a function of $d_{med}$). For example, the function used to calculate Cf2 based on $d_{med}$ may be an increasing function for values of $d_{med}$ greater than zero and a decreasing function for values of $d_{med}$ less than zero. As one example, if $d_{med}$ is greater than or equal to 0, processing circuitry 102 may set Cf2 equal to $d_{med}$ and set Cf2 equal to 0 if $d_{med}$ is less than zero. In this way, if the instance of the estimated shape models is more medial than the current patient anatomy, the value of Cf2 is a positive number, and the overall cost value of the cost function will increase. Again, the cost function (Cf) is equal to Cf1 plus Cf2 plus Cf3 (and possibly updated with weights w1, w2, and w3), and if Cf2 is a positive number, the value of Cf will increase as compared to if the value of Cf2 is zero. Because processing circuitry 102 is determining cost value that satisfies a threshold (e.g., minimizing the cost function), having a positive value of Cf2 causes processing circuitry 102 to not use instances of the estimated shape models that are more medial than the current patient anatomy for determining the pre-morbid or morbid, pre-implant characteristics.

In some examples, the cost function value (Cf) may be based only on Cf1 and Cf2. For instance, for the ER loop, processing circuitry 102 or projection unit 212 may determine which estimated shape model results in minimizing Cf. However, it may be possible that in such cases that the estimated shape model is one with high variation (e.g., has a lower probability of representing pre-morbid or morbid, pre-implant characteristics in the general population). Accordingly, in some examples, for the ER loop, processing circuitry 102 may determine a parameter weighting value (e.g., Cf3). The parameter weighting value weights more likely estimated shape models as having a higher probability of being a representation of the pre-morbid or morbid, pre-implant anatomy and weights less like estimated shape models as having a lower probability of being a representation of the pre-morbid or morbid, pre-implant anatomy.

For example, in some examples, processing circuitry 102 may also determine a sub-cost function value, Cf3, that is used to penalize against more complex solutions within an increasing variance in the data errors. For instance, processing circuitry 102 may determine a gradient smoothing term using eigenvalues to penalize the participating modes of variation according to the following equation.

$$Cf3 = \sum_{i}^{N} \frac{\sum_{j}^{i} \lambda_j}{\sum_{j}^{N} \lambda_j} \times b_i^2$$

In the above equation, N is the number of modes used to build an instance of the estimated shape model. Cf3 may not be necessary in all examples. For example, in the equation for Cf3, if an instance of the estimated shape model has many modes, then there will be a larger number of values to sum together, as compared to if the instance of the estimated shape model had fewer modes. Therefore, the result of the sum (e.g., value of Cf3) will be greater for those estimated shape models having larger modes than those estimated shape models having fewer modes. Accordingly, a larger value of Cf3 will cause the cost function value, Cf, to be bigger than a smaller value of Cf3. Because processing circuitry 102 may be minimizing the value of Cf, estimated shape models having a larger value of Cf3 are less likely to be determined as the pre-morbid or morbid, pre-implant shape of the patient anatomy as compared to estimated shape models having a smaller value of Cf3.

In general, Cf3 is composed of two terms: a coarse or hard term and a fine or smooth one. Eigenvalues are the diagonal positive values of the decomposition matrix. Their order reflects the occurrence of the corresponding eigenvectors into the database. Means that first eigenvalues represent the most "important" or frequent variation in the database, while the last eigenvalues represent the least frequent ones (usually representing noise). In the coarse term of Cf3, processing circuitry 102 may drop those eigenvectors that participate to the least important K % of the database variance (i.e. bi=0 if lambda(i)>q where vi for i<=q represents (100−K) % of the database variance). In the fine term of Cf3, processing circuitry 102 may gradually disadvantage higher eigenvectors. As a result the algorithm avoids complex or noisy solutions. In general, the terminology "smooth" is used to indicate addition of aa regularization term to an optimization method.

Processing circuitry 102 may determine the estimated shape model for which w1*Cf1+w2*Cf2+w3*Cf3 is less than a threshold (e.g., minimized). This estimated shape model is a first order shape model for the first iteration through the global loop.

For example, for the first iteration through the global loop, for the ER loop, assume processing circuitry 102 determines the following estimated shape models based on shape model 106 and different values of $b_i$. For example, a first estimated shape model may be s11, where s11 is equal to $s'+\Sigma_i b11_i \sqrt{\lambda_i} \times v_i$, where s' is shape model 106, $\lambda_i$ is the eigenvalues used to determine shape model 106, and $v_i$ is the eigenvectors used to determine shape model 106. In this example, $b11_1$ is a first weighting parameter. Processing circuitry 102 may determine a second estimated shape model (e.g. s12), where s12 is equal to $s'+\Sigma_i b12_i \sqrt{\lambda_i} \times v_i$, where $b12_i$ is a second weighting parameter. In this manner, processing circuitry 102 may determine a plurality of estimated shape models (e.g., s11, s12, s13, and so forth).

For each of the estimated shape model, processing circuitry 102 may determine a value of Cf1, Cf2, and Cf3. Again, not all of Cf1, Cf2, and Cf3 are needed. For example, processing circuitry 102 may determine s11_Cf1 based on estimated shape model s11 and the first order shape generated by the ICP loop. Processing circuitry 102 may determine s12_Cf1 based on estimated shape model s12 and the first order shape generated by the ICP loop, and so forth. Processing circuitry 102 may determine s11_Cf2, s12_Cf3, and so forth as described above for the example techniques to determine Cf2. Similarly, processing circuitry 102 may determine s11_Cf3, s12_Cf3, and so forth as described above for the example techniques to determine Cf3.

Processing circuitry 102 may determine s11_Cf as: w1*s11_Cf1+w2*s11_Cf2+w3*s11_Cf3, determine s12_Cf as: w1*s12_Cf1+w2*s12_Cf2+w3*s13_Cf3, and so forth. The weights applied to the Cf1, Cf2, and Cf3 may be different for each of s11, s12, s13, and so forth, or the weights may be the same. Processing circuitry 102 may determine which one of s11_Cf, s12_Cf, s13_Cf, and so forth is the minimum (or possibly less than a threshold). Assume that s12_Cf is the minimum. In this example, processing circuitry 102 may determine estimated shape model s12 as the result of the ER loop, which for the first iteration of the global loop is the first order shape model.

This may conclude the first iteration of the global loop. For example, in the first iteration of the global loop, the ICP loop generated a first order shape and the ER loop generated a first order shape model. Then, for the second iteration of the global loop, the input to the ICP loop is the first order shape model generated from the previous ER loop and the first order shape generated from the previous ICP loop. In the ICP loop for the second iteration of the global loop, processing circuitry 102, based on the first order shape model and the first order shape, generates a second order shape. The second order shape is an input to the ER loop in the second iteration of the global loop. Also, in the ER loop, in the second iteration of the global loop, processing circuitry 102 may determine estimated shape models (e.g., s21, s22, s23, and so forth) based on shape model 106 and/or based on the first order shape model (e.g., s12 in this example). The output of the ER loop may be a second order shape model, and this may conclude the second iteration of the global loop.

This process repeats until processing circuitry 102 determines an instance of the estimated shape model that minimizes the Cf value. For instance, assume that after the first iteration of the global loop, processing circuitry 102 outputted estimated shape model s12 having cost value of s12_Cf. After the second iteration of the global loop, processing circuitry 102 outputted estimated shape model s23 having cost value of s23_Cf. After the third iteration of the global loop, processing circuitry 102 outputted estimated shape model s36 having cost value of s36_Cf. In this example, processing circuitry 102 may determine which one of s12_Cf, s23_Cf, or s36_Cf is the minimum value, and determine the estimated shape associated with the minimum Cf value as the pre-morbid or morbid, pre-implant anatomy of the patient. For example, assume that s23_Cf was the minimum. In this example, processing circuitry 102 may determine that estimated shape model s23 is represents the pre-morbid or morbid, pre-implant characteristics of the patient.

In the above examples, processing circuitry 102 may loop through the global loop until the value of Cf is minimized. However, in some examples, processing circuitry 102 may be configured to loop through the global loop for a set number of iterations. Processing circuitry 102 may then determine which one of the estimated shape models resulted in the minimum value of Cf. In some examples, processing circuitry 102 may loop through the global loop until the value of Cf is below a threshold.

As described above, processing circuitry 102 may determine a minimum for the cost function value, Cf. Minimizing the value of Cf or determining the minimum Cf value from a plurality of Cf values are two example ways in which to satisfy the cost function. There may be other ways in which to satisfy the cost function. As one example, satisfying the cost function may mean that the cost value of the cost function is less than a threshold. Also, it may be possible to reconfigure the cost function so that satisfying the cost function means maximizing the cost function. For instance, one of the factors in the cost function may be a distance between points of the estimated shape models and corresponding points in the output from the ICP loop. In some examples, processing circuitry 102 may minimize the distance between the estimated shape models and output from ICP loop and may generate a number that is inversely correlated to distance (e.g., the closer the distance, the larger the number processing circuitry 102 generates). In this example, to satisfy the cost function, processing circuitry 102 may maximize the cost value that that is inversely correlated to the distance. Therefore, although the examples are described with respect to minimizing as part of the global loop and the ICP loop, in some examples, to satisfy (e.g., optimize) the cost function, processing circuitry 102 may maximize the value of Cf. Such techniques are contemplated by this disclosure. For example, a cost value satisfying a threshold value means determining cost value is less than threshold value where cost value being less than threshold value is indicative of pre-morbid or morbid, pre-implant shape or greater than threshold value where cost value being greater than threshold value is indicative of pre-morbid or morbid, pre-implant shape.

FIG. 28 is a flowchart illustrating an example method of operation of a computing device in accordance with one or more example techniques described in this disclosure. The techniques of FIG. 28 will be described with respect to device 100 of FIG. 1 but are not limited to any particular type of computing device. Computing device 100 obtains image data of a joint of a patient that includes an implant, wherein the image data comprises a 3D model of the joint with the implant (2802). Computing device 100 identifies a first object in the 3D model that corresponds to a first component of the implant (2804). Computing device 100 determines a first vector based on the first object (2806). Computing device 100 identifies a second object in the 3D model that corresponds to a second component of the implant (2808). Computing device 100 determines a second vector based on the second object (2810). Computing device 100 determines a third vector that is normal to a plane defined by the first vector and the second vector (2812). Computing device 100 determines a patient coordinate system based on the first vector, the second vector, and the third vector (2814). Computing device 100 identifies an anatomical object in the 3D model (2816). Computing device 100 generates an initial aligned shape that initially aligns the anatomical object from the image data to a shape model based on the determined patient coordinate system (2818). Computing device 100 generates information indicative of a morbid, pre-implant shape of the anatomical object based on the initial aligned shape (2820).

FIG. 29 is a flowchart illustrating an example method of operation of a computing device in accordance with one or more example techniques described in this disclosure. The techniques of FIG. 29 will be described with respect to device 100 of FIG. 1 but are not limited to any particular type of computing device. Computing device 100 determining a shape model for a morbid anatomical object (2902). Computing device 100 obtains image data of a joint of a patient that includes an implant, the image data including a 3D model of the joint with the implant (2904). Computing device 100 identifies voxels that correspond to a bone in the 3D model of the joint with the implant (2906). Computing device 100 determines an initial shape estimate for the bone based on the voxels identified as corresponding to the bone (2908). Computing device 100 aligns the initial shape estimate to the shape model to form an aligned initial shape estimate (2910). Computing device 100 deforms the shape model based on the aligned initial shape estimate to generate a pre-implant, morbid approximation of the bone (2912).

Figure 30:
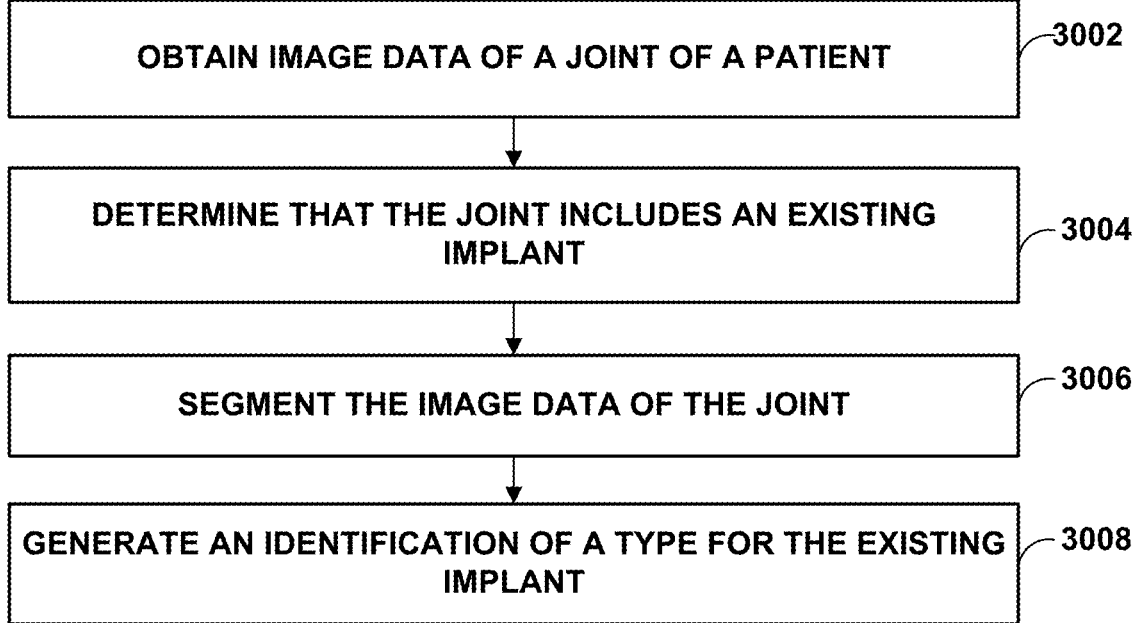
FIG. 30 is a flowchart illustrating an example method of operation of a computing device in accordance with one or more example techniques described in this disclosure.

FIG. 30 is a flowchart illustrating an example method of operation of a computing device in accordance with one or more example techniques described in this disclosure. The techniques of FIG. 30 will be described with respect to device 100 of FIG. 1 but are not limited to any particular type of computing device. Computing device 100 obtains image data of a joint of a patient (3002). Computing device 100 determines that the joint includes an existing implant (3004). Computing device 100 segments the image data of the joint (3006). Computing device 100 generates an identification of a type for the existing implant (3008).

FIG. 31 is a flowchart illustrating an example method of operation of a computing device in accordance with one or more example techniques described in this disclosure. The techniques of FIG. 31 will be described with respect to device 100 of FIG. 1 but are not limited to any particular type of computing device.

Computing device 100 obtains image data of a joint of a patient with an existing implant (3102). Computing device 100 may obtain the image data, for example, using any technique described above for obtaining image data. Computing device 100 identifies, in the image data of the joint of the patient with the existing implant, an image of the existing implant (3104). To identify the image of the existing implant, computing device 100 may, for example, segment the image data of the joint of the patient with the existing implant to determine a segmented image of the existing implant.

In some examples, the image data of the joint of the patient may be a 3D model of the joint; the image of the existing implant may be a 3D model of the existing implant; and the images for the plurality of implant products may be 3D images. In some examples, the image data of the joint of the patient may be a 2D image of the joint; the image of the existing implant may be a 2D image of the existing implant; and the images for the plurality of implant products may be 2D images. In some examples, the image data of the joint of the patient may be a 3D model of the joint; the image of the existing implant may be a 3D model of the existing implant; and the images for the plurality of implant products may be 2D images. The image data of the joint of the patient with the existing implant may also, for example, be an x-ray image.

Computing device 100 accesses, in a memory device, a database that associates a plurality of implant products with images for the plurality of implant products, with each implant product of the plurality of implant products being associated with at least one image (3106). The memory device may be either local or remote. In the database, each respective implant product may be associated with information such as an implant type for the respective implant product, a manufacturer for the respective implant product, a model type for the respective implant, a set of tools recommended or required for removing the implant, a set of surgical recommendations for removal of the implant, specifications such as dimensions for the implant products, or any other such information.

Computing device 100 identifies, based on a comparison of the image of the existing implant to the images for the plurality of implant products, at least one implant product that corresponds to the existing implant (3108). Computing device 100 may determine a digitally reconstructed radiograph of the existing implant from the 3D model of the existing implant and to identify the at least one implant product that corresponds to the existing implant, computing device 100 may compare the digitally reconstructed radiograph of the existing implant to the images for the plurality of implant products.

To identify, based on the comparison of the image of the existing implant to the images for the plurality of implant products, the at least one implant product that corresponds to the existing implant, computing device 100 may be configured to compare a shape of the existing implant in the image data to shapes for the plurality of implant products. Different implants typically have different shapes. For example, the stems of different implant products may be symmetric or non-symmetric, include a collar or not include a collar, have a straight design or an anatomic design, have any one of numerous different cross-sectional shapes, be flanged or roundback, or have any other number of distinctive shape characteristics. The humeral platforms of different implant products may have different neck shaft angles, thickness, polyethylene thickness, polyethylene angulation, or any other number of distinctive shape characteristics. The glenosphere component of an implant products may also have any number of distinctive shape characteristics, such as whether or not the glenosphere component is lateralized or not.

Based on the identified at least one implant products, computing device 100 may be configured to output, via a display for example, an indication of the manufacturer for the at least one implant product that corresponds to the existing implant or an indication of the product identification for the at least one implant product that corresponds to the existing implant. In some examples, computing device 100 may also output an indication of a set required or recommended tools used for removing the respective implant product for the at least one implant product that corresponds to the existing implant and/or a set of instructions for removing the respective implant product for the at least one implant product that corresponds to the existing implant.

In some examples, the database may also store, for each respective implant product, information such as an indication of a country where the respective implant product was installed or approved to be installed, a date or date range on which the respective implant was approved for installation, a date or date range on which the respective implant was discontinued, a date or date range on which the respective implant was approved for installation in a specific country, a date or date range on which the respective implant was discontinued in a specific country, or other such information. Computing device 100 may receive user inputs that may also be used to identify the at least one implant product that corresponds to the existing implant. For example, if it is known that a patient had an implant installed in a certain country on a certain date, then computing device 100 may be configured to eliminate, as candidate implant products, any implant product that was not available in that certain country or until after that certain date.

FIG. 32 is a flowchart illustrating an example method of operation of a computing device in accordance with one or more example techniques described in this disclosure. The techniques of FIG. 32 will be described with respect to device 100 of FIG. 1 but are not limited to any particular type of computing device.

Computing device 100 obtains image data of a joint of a patient with an existing implant (3202). Computing device 100 may obtain the image data, for example, using any technique described above for obtaining image data. Computing device 100 identifies portions of the image corresponding to cement affixing a portion of the existing implant to bone (3204). Computing device 100 may identify the portions of the image that correspond to cement based on the segmenting techniques described above. In some cases, after performing an initial segmentation, computing device 100 may perform local processing, for example around the stem and baseplate of an implant, to more precisely determine the amount and shape or pattern of cement that is present. As implant components are generally smooth and have a known shape, computing device 100 may be able to perform pixel-by-pixel analysis around portions of an implant component to determine the shape and pattern of the cement affixing the implant component to bone.

Based on the portions of the image corresponding to cement, computing device 100 determines a cement intensity value for the joint of the patient with the existing implant (3206). The cement intensity value may, for example, be or correspond to an estimate, determined from the image data, of the affixing strength of the cement. The cement intensity may, for example, be determined based on one or more of a volume of cement, a volume of cement relative to surface area of implant or bone, a thickness of cement, a density of cement region of interest (ROI), a surface seating of an implant relative to cement, or other such factors. Computing device 100 may also determine the cement intensity based on a pattern of the cement. As one example, even if an overall volume or average thickness of cement is the same for two different implants, the cement intensity may be different based on whether or not there is more cement near the base of a stem or near the end of the stem. As another example, even if an overall volume or average thickness of cement is the same for two different implants, the cement intensity may be different based on whether or not the edges of the cement are smooth or rough.

Computing device 100 generates an output based on the determined cement intensity (3208). The output may, for example, be one or more of an estimation of a difficulty associated with removing the existing implant or surgical recommendations for removing the existing implant. Computing device 100 may additionally or alternatively also output surgical recommendations based on factors such as a volume of cement, a volume of cement relative to surface area of implant or bone, a thickness of cement, a density of cement ROI, a surface seating of an implant relative to cement, a pattern for the cement, or other such factors.

Computing device 100 may access a database that stores, for a plurality of a cement intensities, an associated measure of the difficulty needed to remove an implant component held by the cement with that intensity. Based on a regression analysis of the plurality of cement intensities, computing device 100 may determine an estimation of a difficulty needed to remove the existing implant based on the cement intensity for the joint of the patient with the existing implant. The measure of difficulty needed to remove the implant may, for example, be one or more of a number of hits needed to remove the implant, a measured force needed to remove the implant, surgeon feedback (e.g., a scale of 1 to 10), a duration of time needed to perform a removal phases, or any such feedback. In this regard, the databased may store information for already performed surgeries or information derived from already performed surgeries. The estimation of difficulty, as output to a user of device 100, may take virtually any form, including a numerical value (e.g., a scale of 1 to 10), a classification (e.g., easy, medium, hard), an estimated amount of time needed to perform a removal phases, or any other such type.

In some implementations the cement intensities may be associated with specific types of implants or specific makes and models of implants. Thus, once an implant type or implant make or model is determined, computing device 100 may determine the estimation of the difficulty needed to remove the existing implant based on the type or model for the existing implant. For example, based on a regression analysis of the plurality of cement intensities for the determined implant type or model, computing device 100 may determine the estimation of the difficulty.

While the techniques been disclosed with respect to a limited number of examples, those skilled in the art, having the benefit of this disclosure, will appreciate numerous modifications and variations there from. For instance, it is contemplated that any reasonable combination of the described examples may be performed. It is intended that the appended claims cover such modifications and variations as fall within the true spirit and scope of the invention.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Operations described in this disclosure may be performed by one or more processors, which may be implemented as fixed-function processing circuits, programmable circuits, or combinations thereof, such as one or more digital signal processors (DSPs), general purpose microprocessors, application specific integrated circuits (ASICs), field programmable gate arrays (FPGAs), or other equivalent integrated or discrete logic circuitry. Fixed-function circuits refer to circuits that provide particular functionality and are preset on the operations that can be performed. Programmable circuits refer to circuits that can programmed to perform various tasks and provide flexible functionality in the operations that can be performed. For instance, programmable circuits may execute instructions specified by software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. Accordingly, the terms "processor" and "processing circuitry," as used herein may refer to any of the foregoing structures or any other structure suitable for implementation of the techniques described herein.

Various examples have been described. These and other examples are within the scope of the following claims.

The invention claimed is:

1. A method comprising:
obtaining, by a computing system, a 3D model of a joint of a patient;
determining, by the computing system, that the joint includes an existing implant;
segmenting, by the computing system, the 3D model;
identifying, by the computing system in the segmented 3D model, voxels that correspond to the existing implant based on an intensity of voxels in the 3D model;
determining, by the computing system, a number of unconnected objects in the voxels that correspond to the existing implant;
determining, by the computing system, a type for the existing implant based on the number of the unconnected objects, wherein the type for the existing implant comprises one of a reverse shoulder implant type, an anatomical shoulder implant type, or a hemispherical shoulder implant type; and
generating, by the computing system, surgical guidance based on the type for the existing implant.

2. The method of claim 1, wherein determining that the joint includes the existing implant comprises determining, by the computing system, that the joint includes the existing implant based on an analysis of the 3D model.

3. The method of claim 1, wherein determining that the joint includes the existing implant comprises determining, by the computing system, that the joint includes the existing implant based on a user input.

4. The method of claim 1, wherein determining the type for the existing implant based on the number of the unconnected objects comprises:
determining that the voxels that correspond to the existing implant form three unconnected objects; and
determining that the type for the existing implant comprises an undefined type in response to determining that the voxels that correspond to the existing implant form the three unconnected objects.

5. The method of claim 1, wherein determining the type for the existing implant based on the number of the unconnected objects comprises:
determining that the voxels that correspond to the existing implant form one connected object;
in response to determining that the voxels that correspond to the existing implant form the one connected object, identifying, based on locations of the voxels that correspond to the existing implant, second locations of voxels;
searching, in the second locations of voxels, for metallic glenoid markers; and in response to not detecting the metallic glenoid markers, determining that the type for the existing implant comprises the hemispherical shoulder implant type.

6. The method of claim 5, further comprising:
generating an output indicating that the type for the existing implant comprises the hemispherical shoulder implant type.

7. The method of claim 1, wherein determining the type for the existing implant based on the number of the unconnected objects comprises:
determining that the voxels that correspond to the existing implant form one connected object;
in response to determining that the voxels that correspond to the existing implant form the one connected object, identifying, based on a location of the voxels that correspond to the existing implant, a second location of voxels;
searching, in the second location of voxels, for metallic glenoid markers; and
in response to detecting the metallic glenoid markers, determining that the type for the existing implant comprises the anatomical shoulder implant type.

8. The method of claim 7, further comprising:
generating an output indicating that the type for the existing implant comprises the anatomical shoulder implant type.

9. The method of claim 1, wherein determining the type for the existing implant based on the number of the unconnected objects comprises:
determining that the voxels that correspond to the existing implant form two unconnected objects; and
in response to determining that the voxels that correspond to the existing implant form the two unconnected objects, determining that the type for the existing implant comprises the reverse shoulder type.

10. The method of claim 9, further comprising:
generating an output indicating that the type for the existing implant comprises the reverse shoulder type.

11. The method of claim 1, wherein identifying, by the computing system in the segmented 3D model, the voxels that correspond to the existing implant based on the intensity of the voxels in the 3D model comprises:
determining radiodensity values for the voxels in the 3D model; and
identifying a subset of voxels in the 3D model that have radiodensity values exceeding a threshold value.

12. A device comprising:
a memory; and
one or more processors coupled to the memory, implemented in circuitry, and configured to:
obtain a 3D model of a joint of a patient;
determine that the joint includes an existing implant;
segment the 3D model;
identify, in the segmented 3D model, voxels that correspond to the existing implant based on an intensity of voxels in the 3D model;
determine a number of unconnected objects in the voxels that correspond to the existing implant;
determine a type for the existing implant based on the number of the unconnected objects, wherein the type for the existing implant comprises one of a reverse shoulder implant type, an anatomical shoulder implant type, or a hemispherical shoulder implant type; and
generate surgical guidance based on the type for the existing implant.

13. The device of claim 12, wherein the one or more processors are configured to, as part of determining that the joint includes the existing implant, determine that the joint includes the existing implant based on an analysis of the 3D model.

14. The device of claim 12, wherein the one or more processors are configured to, as part of determining that the joint includes the existing implant, determine that the joint includes the existing implant based on a user input.

15. The device of claim 12, wherein the one or more processors are configured to, as part of determining the type for the existing implant based on the number of the unconnected objects:

determine that the voxels that correspond to the existing implant form three unconnected objects; and determine that the type for the existing implant comprises an undefined type in response to determining that the voxels that correspond to the existing implant form the three unconnected objects.

16. The device of claim 12, wherein the one or more processors are configured to, as part of determining the type for the existing implant based on the number of the unconnected objects:

determine that the voxels that correspond to the existing implant form one connected object;

in response to determining that the voxels that correspond to the existing implant form the one connected object, identify, based on locations of the voxels that correspond to the existing implant, second locations of voxels;

search, in the second locations of voxels, for metallic glenoid markers; and in response to not detecting the metallic glenoid markers, determine that the type for the existing implant comprises the hemispherical shoulder implant type.

17. The device of claim 16, wherein the one or more processors are further configured to generate an output indicating that the type for the existing implant comprises the hemispherical shoulder implant type.

18. The device of claim 12, wherein the one or more processors are configured to, as part of determining the type for the existing implant based on the number of the unconnected objects:

determine that voxels that correspond to the existing implant form one connected object;

in response to determining that the voxels that correspond to the existing implant form the one connected object, identify, based on a location of the voxels that correspond to the existing implant, a second location of voxels;

search, in the second location of voxels, for metallic glenoid markers; and in response to detecting the metallic glenoid markers, determine that the type for the existing implant comprises the anatomical shoulder implant type.

19. The device of claim 12, wherein the one or more processors are configured to, as part determining the type for the existing implant based on the number of the unconnected objects:

determine that the voxels that correspond to the existing implant form two unconnected objects; and in response to determining that the voxels that correspond to the existing implant form the two unconnected objects, determine that the type for the existing implant comprises the reverse shoulder type.

20. The device of claim 12, wherein to identify the voxels that correspond to the existing implant based on the intensity of the voxels in the 3D model, the one or more processors are configured to:

determine radiodensity values for the voxels in the 3D model; and identify a subset of voxels in the 3D model that have radiodensity values exceeding a threshold value.

* * * * *